(12) United States Patent
Chen et al.

(10) Patent No.: US 12,378,197 B2
(45) Date of Patent: *Aug. 5, 2025

(54) ORGANIC ELECTROLUMINESCENT MATERIALS AND DEVICES

(71) Applicant: Universal Display Corporation, Ewing, NJ (US)

(72) Inventors: Hsiao-Fan Chen, Taipei (TW); Peter Wolohan, Princeton Junction, NJ (US); Nicholas J. Thompson, Hamilton, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 757 days.

This patent is subject to a terminal disclaimer.

(21) Appl. No.: 16/441,058

(22) Filed: Jun. 14, 2019

(65) Prior Publication Data

US 2020/0017508 A1   Jan. 16, 2020

Related U.S. Application Data

(60) Provisional application No. 62/697,459, filed on Jul. 13, 2018.

(51) Int. Cl.
| | | |
|---|---|---|
| C07D 209/82 | (2006.01) |
| C07C 211/54 | (2006.01) |
| C07C 255/51 | (2006.01) |
| C07D 241/46 | (2006.01) |
| C07D 251/24 | (2006.01) |
| C07D 265/38 | (2006.01) |
| C07D 279/22 | (2006.01) |
| C07D 295/033 | (2006.01) |
| C07D 487/04 | (2006.01) |
| C07D 491/048 | (2006.01) |
| C07D 495/04 | (2006.01) |
| H10K 50/12 | (2023.01) |
| H10K 50/16 | (2023.01) |
| H10K 50/18 | (2023.01) |
| H10K 85/30 | (2023.01) |
| H10K 85/60 | (2023.01) |
| H10K 101/20 | (2023.01) |

(52) U.S. Cl.
CPC .......... *C07D 209/82* (2013.01); *C07C 211/54* (2013.01); *C07C 255/51* (2013.01); *C07D 241/46* (2013.01); *C07D 251/24* (2013.01); *C07D 265/38* (2013.01); *C07D 279/22* (2013.01); *C07D 295/033* (2013.01); *C07D 487/04* (2013.01); *C07D 491/048* (2013.01); *C07D 495/04* (2013.01); *H10K 85/341* (2023.02); *H10K 85/631* (2023.02); *H10K 85/654* (2023.02); *H10K 85/656* (2023.02); *H10K 85/6572* (2023.02); *H10K 50/12* (2023.02); *H10K 50/16* (2023.02); *H10K 50/18* (2023.02); *H10K 2101/20* (2023.02)

(58) Field of Classification Search
CPC ............. H01L 51/0059; H01L 51/0067; H01L 51/0069; H10K 85/654; H10K 85/656; H10K 85/631; H10K 85/341
See application file for complete search history.

(56) References Cited

U.S. PATENT DOCUMENTS

| | | | |
|---|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |

(Continued)

FOREIGN PATENT DOCUMENTS

| | | |
|---|---|---|
| CN | 107880056 | 4/2018 |
| EP | 0650955 | 5/1995 |

(Continued)

OTHER PUBLICATIONS

Wang et al., machine translation of CN 107880056 (2016) pp. 1-47. (Year: 2016).*
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).

(Continued)

*Primary Examiner* — Dylan C Kershner
(74) *Attorney, Agent, or Firm* — DUANE MORRIS LLP

(57) ABSTRACT

A compound having a structure of Formula I,

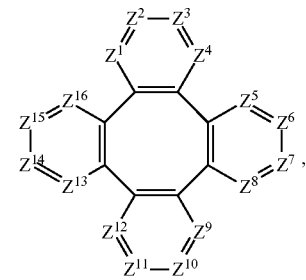

is provided. In Formula I, $Z^1$ to $Z^{16}$ are each CR or N; three consecutive ones of $Z^1$ to $Z^{16}$ within the same ring cannot be N; each R is independently a hydrogen or a substituent selected from a variety of substituents; at least one R includes and electron donor substituent; at least one R includes an electron acceptor substituent; and any two Rs on the same ring can be joined or fused together to form a ring. Organic light emitting devices, consumer products, formulations, and chemical structures containing the compounds are also disclosed.

20 Claims, 3 Drawing Sheets

(56) References Cited

U.S. PATENT DOCUMENTS

| | | | |
|---|---|---|---|
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A * | 8/2000 | Baldo | H10K 50/11 428/917 |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 10,109,799 B2* | 10/2018 | Kwong | C07D 471/04 |
| 10,155,773 B2 | 12/2018 | Kim et al. | |
| 10,566,546 B2* | 2/2020 | Kwong | H10K 85/657 |
| 10,910,577 B2* | 2/2021 | Thompson | H10K 85/12 |
| 11,174,259 B2* | 11/2021 | Wolohan | C07D 519/00 |
| 11,322,691 B2* | 5/2022 | Wolohan | H10K 85/341 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0091862 A1* | 5/2003 | Tokito | H01L 51/0085 428/690 |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Garashi et al. | |
| 2004/0174116 A1 | 9/2004 | Lu et al. | |
| 2005/0025993 A1 | 2/2005 | Thompson et al. | |
| 2005/0112407 A1* | 5/2005 | Ogasawara | C07C 211/61 313/506 |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0240285 A1* | 10/2006 | Uchida | C09K 11/06 428/917 |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Wakuma et al. | |
| 2009/0030202 A1 | 1/2009 | Wakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2010/0004467 A1* | 1/2010 | Fallis | C07D 333/10 549/80 |
| 2010/0038599 A1* | 2/2010 | Holliday | H10K 85/141 252/500 |
| 2010/0187984 A1* | 7/2010 | Lin | C07D 491/04 313/504 |
| 2014/0077172 A1* | 3/2014 | So | H10K 50/121 438/46 |
| 2015/0243893 A1* | 8/2015 | Joseph | C07D 495/04 257/40 |
| 2016/0013422 A1* | 1/2016 | Kwong | C07D 209/94 548/417 |
| 2016/0093812 A1* | 3/2016 | Stoessel | C09K 11/06 257/40 |
| 2017/0077409 A1* | 3/2017 | Kwong | H01L 51/0055 |
| 2018/0108844 A1 | 4/2018 | Lee et al. | |
| 2018/0287087 A1* | 10/2018 | Thompson | H10K 85/6576 |
| 2018/0370957 A1* | 12/2018 | Gao | H01L 51/008 |
| 2018/0370978 A1* | 12/2018 | Wolohan | C07D 487/04 |
| 2019/0036031 A1* | 1/2019 | Wolohan | C07D 209/86 |
| 2019/0123286 A1* | 4/2019 | Xia | C09K 11/025 |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |

(56) References Cited

FOREIGN PATENT DOCUMENTS

| WO | 2009066779 | 5/2009 |
|----|------------|--------|
| WO | 2009086028 | 7/2009 |
| WO | 2009100991 | 8/2009 |

OTHER PUBLICATIONS

Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter, " Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2, N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "p. 185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris|4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N/\CAN/\Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Ostergard et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSLYKE, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).

(56) References Cited

OTHER PUBLICATIONS

Wong, Wai-Yeung, "Multifunctional Iridium Complexes Based on Carbazole Modules as Highly Efficient Electrophosphors," Angew. Chem. Int. Ed., 45:7800-7803 (2006).

Hau, Chun-Kit et al., "Enantioselective Brønsted base catalyzed [4+2] cycloaddition using novel amino-substituted letraphenylene derivatives" Tetrahedron, 66, 2010, pp. 9860-9874.

* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 62/697,459, filed Jul. 13, 2018, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

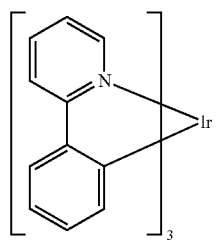

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative) Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an aspect of the present disclosure, a compound having a structure of Formula I,

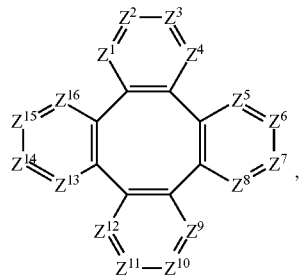

is provided. In the structure of Formula I:
$Z^1$ to $Z^{16}$ are each CR or N;
three consecutive ones of $Z^1$ to $Z'^6$ within the same ring cannot be N;
each R is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
at least one R comprises an electron donor substituent selected from the group consisting of an aryloxy group, an amino group, or a 5-membered aromatic ring containing one heteroatom;
at least one R comprises an electron acceptor substituent selected from the group consisting of a halogen, a nitrile group, a 5-membered aromatic ring containing at least two heteroatoms, and a 6-membered heteroaromatic ring; and
any two Rs on the same ring can be joined or fused together to form a ring.

An OLED comprising the compound of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
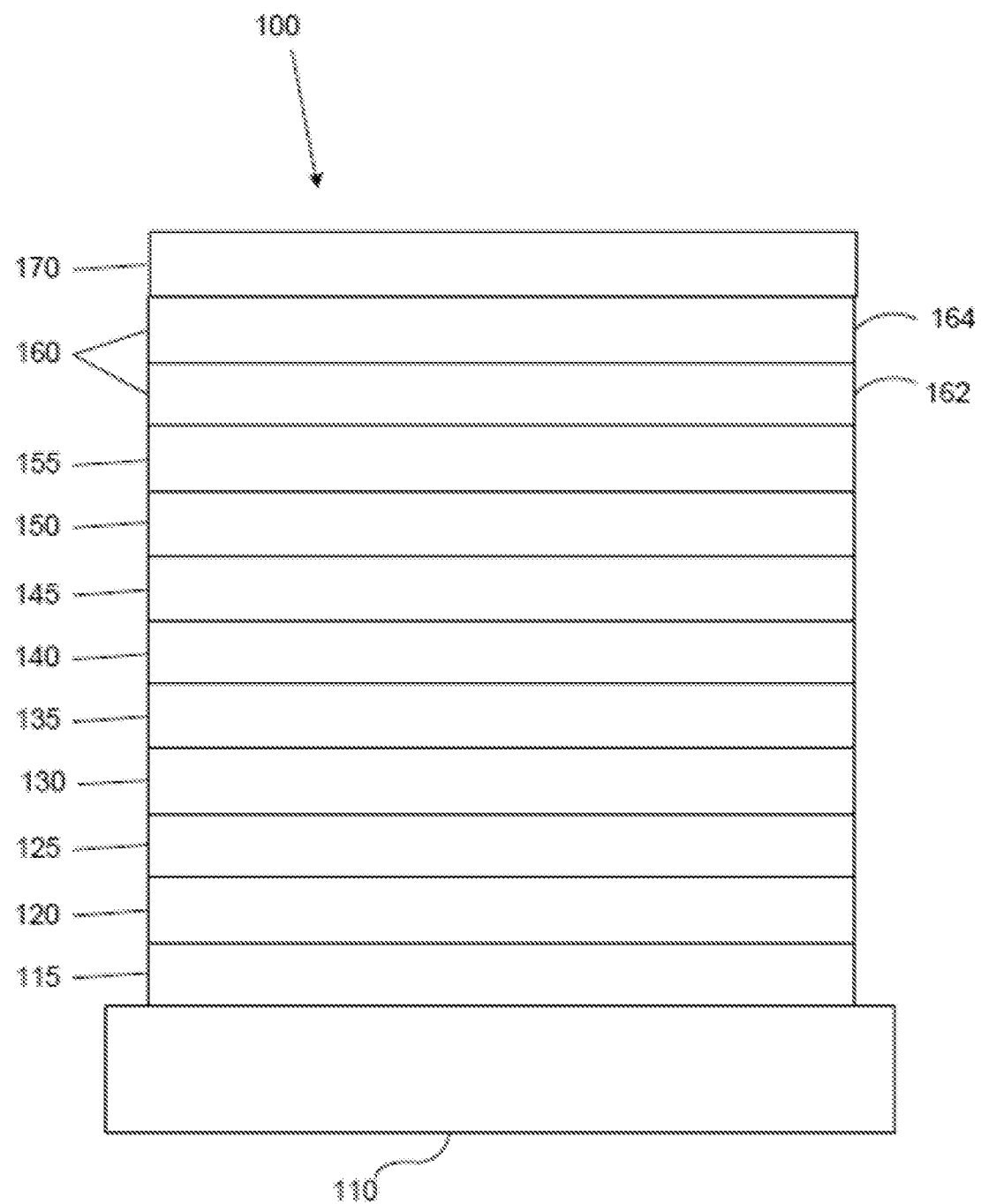
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
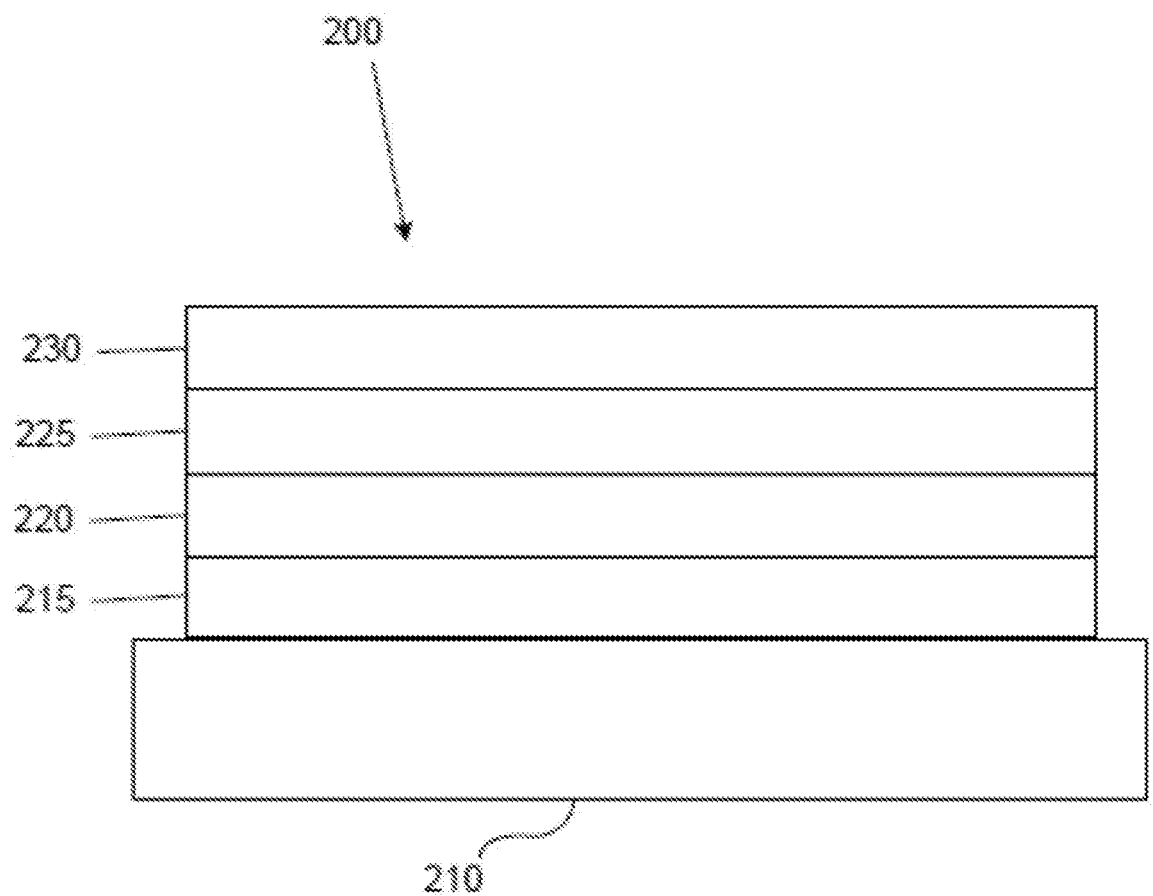
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —O$R_s$ radical.

The terms "sulfanyl" or "thio-ether" are used interchangeably and refer to a —S$R_s$ radical.

The term "sulfinyl" refers to a —S(O)—$R_s$ radical.

The term "sulfonyl" refers to a —SO$_2$—$R_s$ radical.

The term "phosphino" refers to a —P($R_s$)$_3$ radical, wherein each R can be same or different.

The term "silyl" refers to a —Si($R_s$)$_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms.

Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution) Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., Tetrahedron 2015, 71, 1425-30 and Atzrodt et al., *Angew. Chem. Int. Ed. (Reviews)* 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

According to an aspect of the present disclosure, a compound having a structure of Formula I,

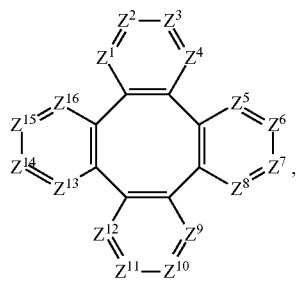

is provided. In the structure of Formula I:
$Z^1$ to $Z^{16}$ are each CR or N;
three consecutive ones of $Z^1$ to $Z^{16}$ within the same ring cannot be N;
each R is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
at least one R comprises an electron donor substituent selected from the group consisting of aryloxy group, an amino group, or a 5-membered aromatic ring containing one heteroatom;
at least one R comprises an electron acceptor substituent selected from the group consisting of a halogen, a nitrile group, a 5-membered aromatic ring containing at least two heteroatoms, and a 6-membered heteroaromatic ring; and any two Rs on the same ring can be joined or fused together to form a ring. Because each R is independently selected from the group defined above, the scope of Formula I as defined includes all permutations of Rs, including, but not limited to, the embodiments (a) where all of the Rs present in the compound are the same, (b) where all of the Rs in the compound are different, (c) where some of the Rs are the same with the remainder being different, and (d) where there are one or more groups of different Rs where the Rs within each group are the same, and the remainder being different.

In some embodiments, each R that includes an aryloxy group, an amino group, or a 5-membered aromatic ring containing one heteroatom, does not include a halogen, a nitrile group, a 5-membered aromatic ring containing at least two heteroatoms, or a 6-membered heteroaromatic ring.

When all Rs are not the same, (i) some Rs can be the same and some can be different or (ii) all Rs can be different. There can also be multiple groups if Rs that are the same (e.g., two Rs are carbazole and two Rs are methoxide). In addition, it should be noted that Zs on different rings (e.g., $Z^1$ and $Z^{16}$, $Z^4$ and $Z^5$, $Z^8$ and $Z^9$, and $Z^{12}$ and $Z^{13}$) can't be joined to form a ring.

In some embodiments, at least one R comprises at least one electron donor group selected from the group consisting of carbazole, diphenylamino, phenoxazine, phenothiazine, dibenzoazasiline, pyrrolidine, piperidine, phenoxide, and methoxide.

In some embodiments, at least one R comprises at least one electron acceptor group selected from the group consisting of cyano, pyrazole, imidazole, triazole, pyridine, pyrimidine, triazine, aza-carbazole, aza-dibenzofuran, and aza-dibenzothiophene group. In some embodiments, each of the at least one electron donor group is on a different ring from each of the at least one electron acceptor group.

In some embodiments, each one of $Z^1$ through $Z^{16}$ is CR.
In some embodiments, at least one of $Z^1$ through $Z^{16}$ is N.
In some embodiments, exactly one of $Z^1$ through $Z^{16}$ is N.

In some embodiments, at least one R comprises a chemical group selected from the group consisting of

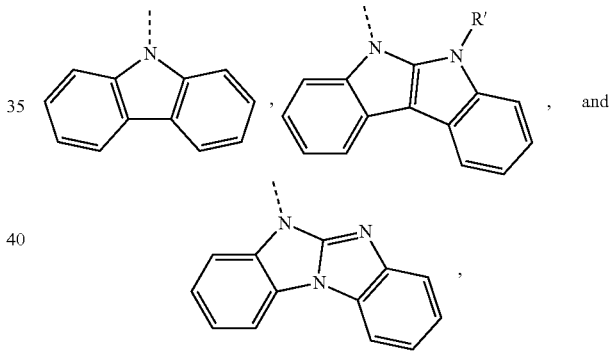

wherein R' is selected from the group consisting of alkyl, cycloalkyl, heteroalkyl, aryl, and heteroaryl.

In some embodiments, at least two Rs comprise donor substituents, and one R comprises an acceptor substituent, where the donor substituents are on different rings of the tetraphenylene, on two rings next to each other, or on two rings that are opposite from each other. In some embodiments, the two donor Rs are the same, and in some embodiments, the two donor Rs are different. In some embodiments, at least two Rs comprise acceptor substituents, and one R comprises a donor substituent, where the acceptor substituents are on different rings of the tetraphenylene, on two rings next to each other, or on two that are opposite from each other. In some embodiments, the two acceptor Rs are the same, and in some embodiments, the two acceptor Rs are different.

In some embodiments, the compound is selected from the group consisting of Compound 1 to Compound 3,064,600 defined as follows:

| Compound Z | Structure of Compound Z | Ar¹, Ar², Ar³, Ar⁴ | Z |
|---|---|---|---|
| Compound 1 to Compound 540,000 having the structure | (structure) | wherein Ar¹ = D$i$, Ar² = A$j$, Ar³ = A$k$, and Ar⁴ = A$l$, wherein $i$ is an integer from 1 to 20, $j$ is an integer from 1 to 30, $k$ is an integer from 1 to 30, and $l$ is an integer from 1 to 30, | wherein $Z = i + 20(j-1) + 600(k-1) + 18{,}000(l-1)$, |
| Compound 540,001 to Compound 1,436,000 having the structure | (structure) | wherein Ar¹ = A$i$, Ar² = D$j$, Ar³ = D$k$, and Ar⁴ = D$l$, wherein $i$ is an integer from 1 to 14, $j$ is an integer from 1 to 40, $k$ is an integer from 1 to 40, and $l$ is an integer from 1 to 40, | wherein $Z = i + 14(j-1) + 560(k-1) + 22{,}400(l-1) + 540{,}000$, |
| Compound 1,436,001 to Compound 1,468,000 having the structure | (structure) | wherein Ar¹ = A$i$, Ar² = D$j$, Ar³ = D$k$, and Ar⁴ = D$l$, wherein $i$ is an integer from 29 to 30, $j$ is an integer from 1 to 40, $k$ is an integer from 1 to 20, and $l$ is an integer from 1 to 20, | wherein $Z = (i-28) + 2(j-1) + 80(k-1) + 1{,}600(l-1) + 1{,}4360{,}000$, |
| Compound 1,468,001 to Compound 1,484,000 having the structure | (structure) | wherein Ar¹ = A$i$, Ar² = D$j$, Ar³ = D$k$, and Ar⁴ = D$l$, wherein $i$ is an integer from 29 to 30, $j$ is an integer from 21 to 40, $k$ is an integer from 1 to 20, and $l$ is an integer from 21 to 40, | wherein $Z = (i-28) + 2(j-21) + 40(k-1) + 800(l-21) + 1{,}468{,}000$, |
| Compound 1,484,001 to Compound 2,204,000 having the structure | (structure) | wherein Ar¹ = D$i$, Ar² = D$j$, Ar³ = A$k$, and Ar⁴ = A$l$, wherein $i$ is an integer from 1 to 20, $j$ is an integer from 1 to 40, $k$ is an integer from 1 to 30, and $l$ is an integer from 1 to 30, | wherein $Z = i + 20(j-1) + 800(k-1) + 24{,}000(l-1) + 1{,}484{,}000$, |
| Compound 2,204,001 to Compound 2,924,000 having the structure | (structure) | wherein Ar¹ = D$i$, Ar² = A$j$, Ar³ = D$k$, and Ar⁴ = A$l$, wherein $i$ is an integer from 1 to 20, $j$ is an integer from 1 to 30, $k$ is an integer from 1 to 40, and $l$ is an integer from 1 to 30, | wherein $Z = i + 20(j-1) + 600(k-1) + 24{,}000(l-1) + 2{,}204{,}000$, |

| Compound Z | Structure of Compound Z | Ar¹, Ar², Ar³, Ar⁴ | Z |
|---|---|---|---|
| Compound 2,924,001 to Compound 2,946,400 having the structure | | wherein Ar¹ = D$i$, Ar² = A$j$, and Ar³ = D$k$, wherein $i$ is an integer from 1 to 40, $j$ is an integer from 1 to 14, and $k$ is an integer from 1 to 40, | wherein $Z = i + 14(j-1) + 560(k-1) + 2{,}924{,}000$, |
| Compound 2,946,401 to Compound 2,948,000 having the structure | | wherein Ar¹ = D$i$, Ar² = A$j$, and Ar³ = D$k$, wherein $i$ is an integer from 1 to 40, $j$ is an integer from 29 to 30, and $k$ is an integer from 1 to 20, | wherein $Z = i + 40(j-29) + 80(k-1) + 2{,}946{,}400$, |
| Compound 2,948,001 to Compound 2,948,800 having the structure | | wherein Ar¹ = D$i$, Ar² = A$j$, and Ar³ = D$k$, wherein $i$ is an integer from 21 to 40, $j$ is an integer from 29 to 30, and $k$ is an integer from 21 to 40, | wherein $Z = (i-20) + 2(j-29) + 40(k-21) + 2{,}948{,}000$, |
| Compound 2,948,801 to Compound 2,966,800 having the structure | | wherein Ar¹ = A$i$, Ar² = D$j$, and Ar³ = A$k$, wherein $i$ is an integer from 1 to 30, $j$ is an integer from 1 to 20, and $k$ is an integer from 1 to 30, | wherein $Z = i + 30(j-1) + 600(k-1) + 2{,}948{,}800$, |
| Compound 2,966,801 to Compound 3,014,800 having the structure | | wherein Ar¹ = D$i$, Ar² = D$j$, and Ar³ = A$k$, wherein $i$ is an integer from 1 to 40, $j$ is an integer from 1 to 40, and $k$ is an integer from 1 to 30, | wherein $Z = i + 40(j-1) + 1{,}600(k-1) + 2{,}966{,}800$, |
| Compound 3,014,801 to Compound 3,062,800 having the structure | | wherein Ar¹ = A$i$, Ar² = D$j$, and Ar³ = D$k$, wherein $i$ is an integer from 1 to 30, $j$ is an integer from 1 to 40, and $k$ is an integer from 1 to 40, | wherein $Z = i + 30(j-1) + 1{,}200(k-1) + 3{,}014{,}800$, |

-continued

| Compound Z | Structure of Compound Z | Ar¹, Ar², Ar³, Ar⁴ | Z |
|---|---|---|---|
| Compound 3,062,801 to Compound 3,063,400 having the structure | 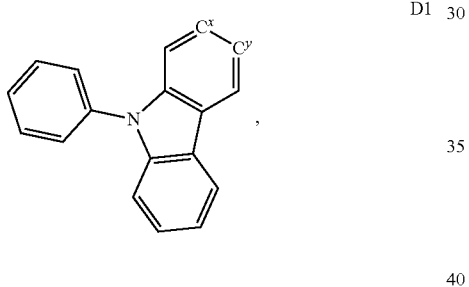 | wherein $Ar^1 = Di$ and $Ar^3 = Aj$, wherein i is an integer from 1 to 20 and j is an integer from 1 to 30, | wherein $Z = i + 20(j - 1) + 3,062,800$, |
| Compound 3,063,401 to Compound 3,064,600 having the structure | 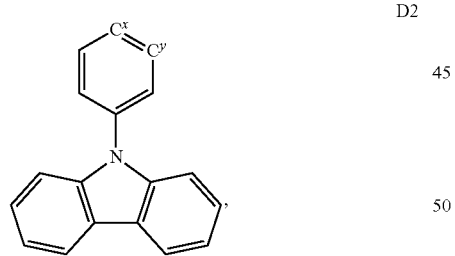 | wherein $Ar^1 = Di$ and $Ar^2 = Aj$, wherein i is an integer from 1 to 40 and j is an integer from 1 to 30, | wherein $Z = i + 40(j - 1) + 3,063,400$; | where D1 to D40 have the following structures:

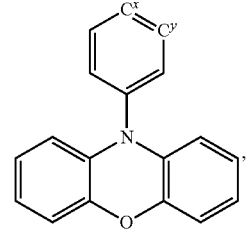

D1

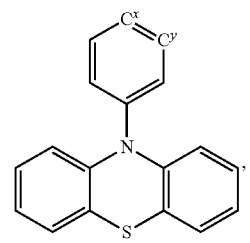

D2

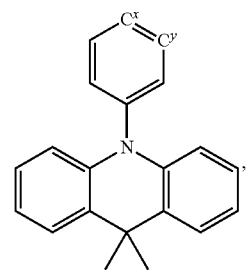

D3

-continued

D4

D5

D6

-continued
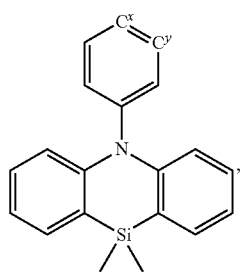 D7
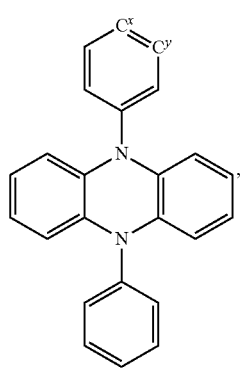 D8
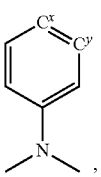 D9
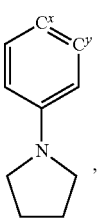 D10
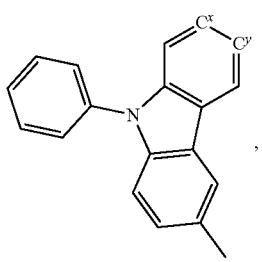 D11
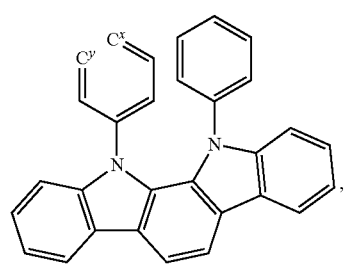 D12
-continued
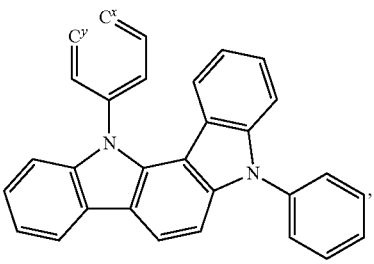 D13
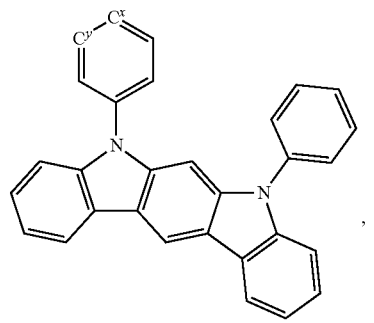 D14
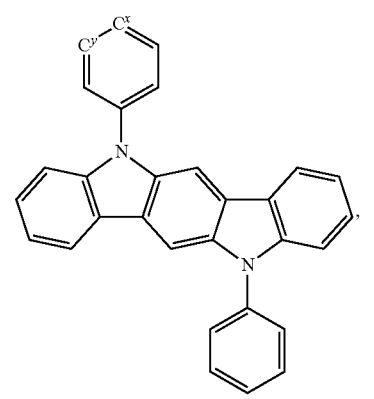 D15
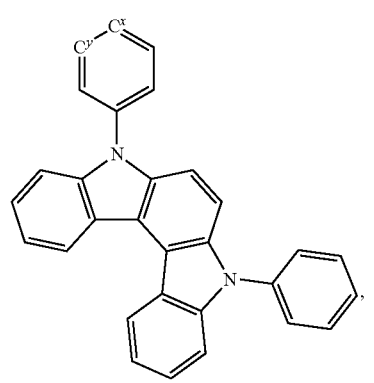 D16

D17 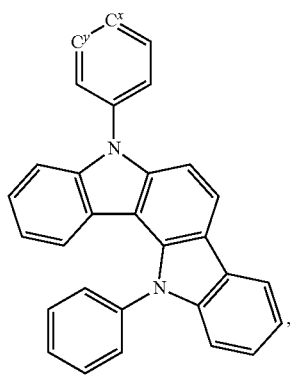
D18 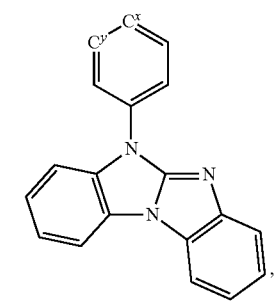
D19 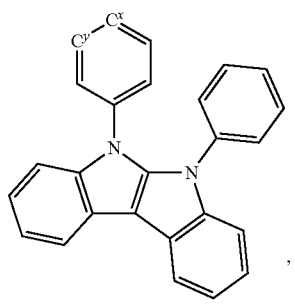
D20 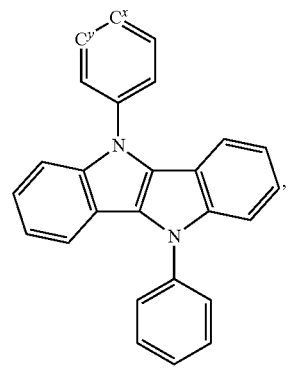
D21 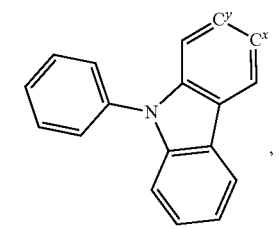
D22 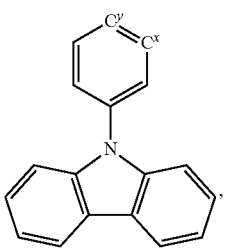
D23 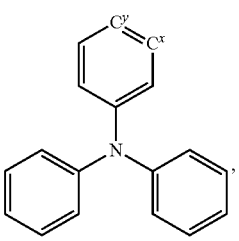
D24 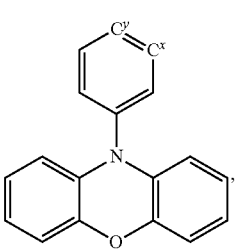
D25 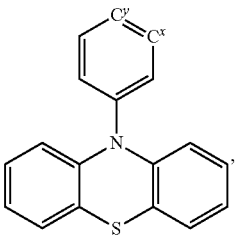
D26 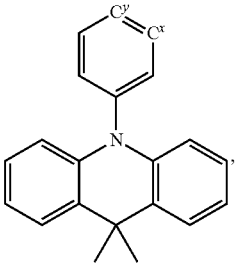
D27 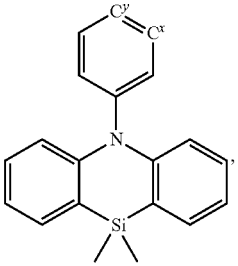

D28 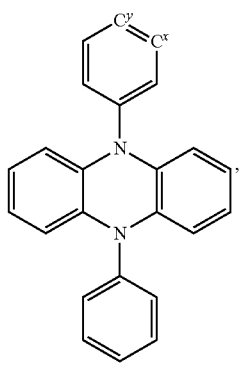
D29 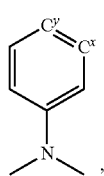
D30 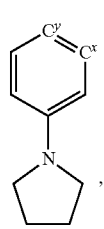
D31 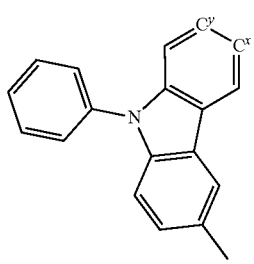
D32 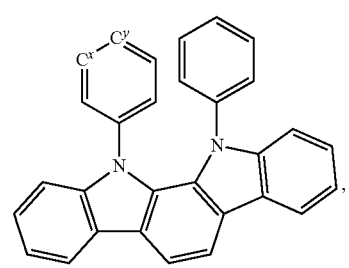
D33 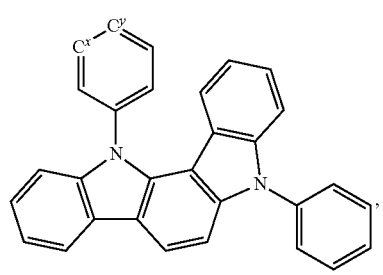
D34 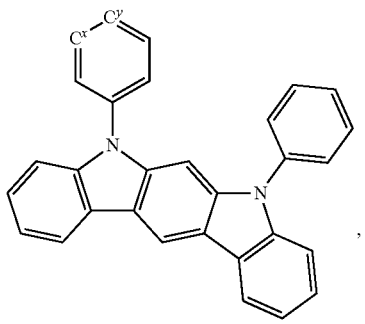
D35 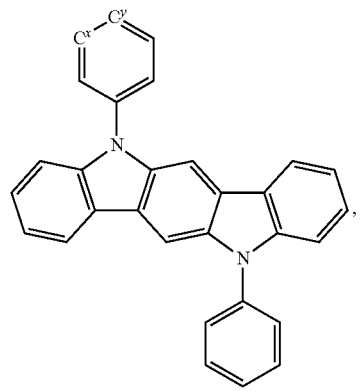
D36 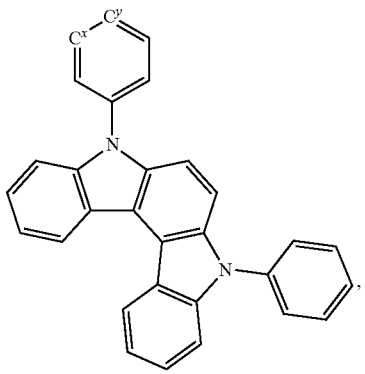
D37 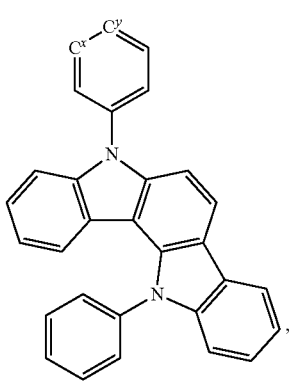

-continued
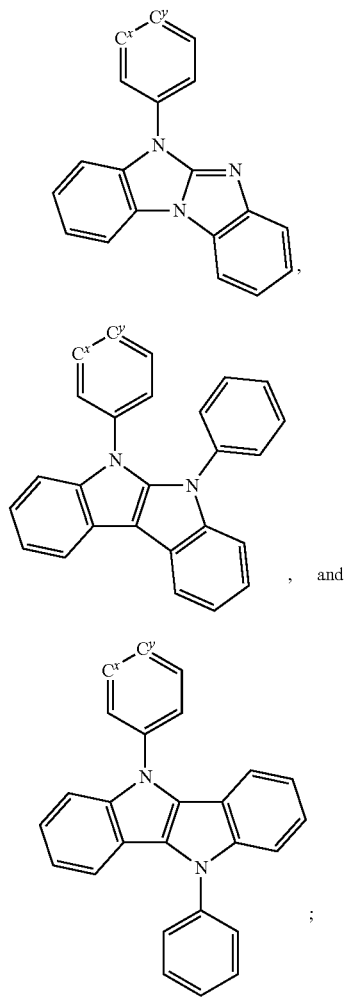
D38,
and
where A1 to A30 have the following structures:
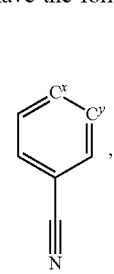
A1
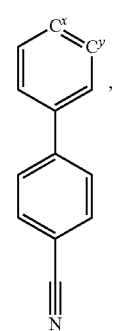
A2
-continued
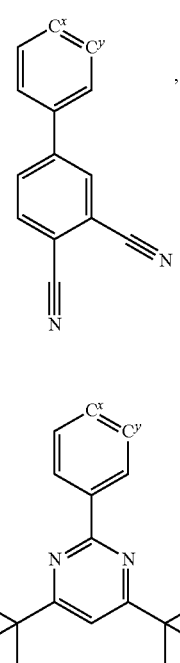
D39, D40
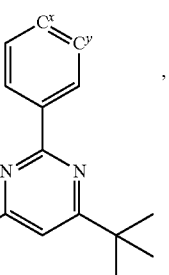
A3
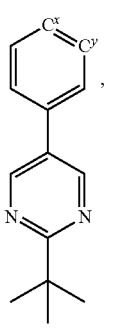
A4, A5
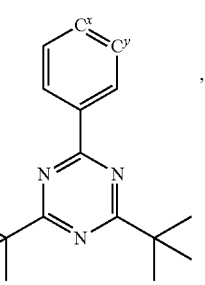
A6
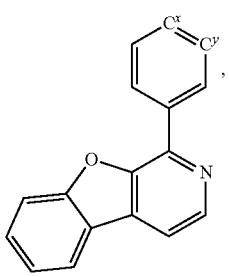
A7

-continued
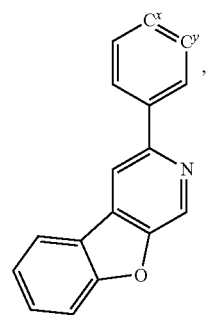
A8
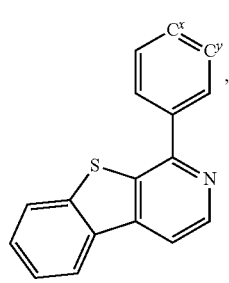
A9
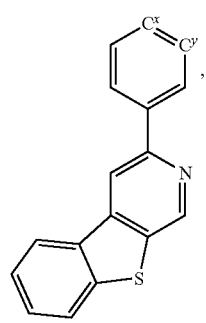
A10
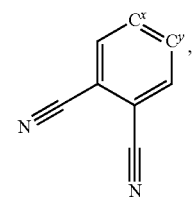
A11
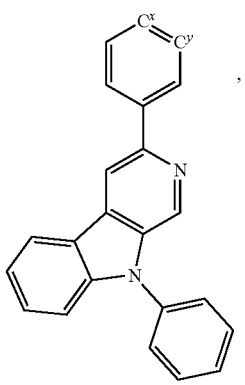
A12
-continued
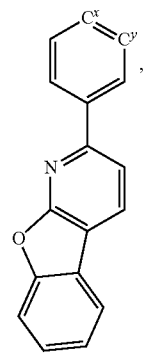
A13
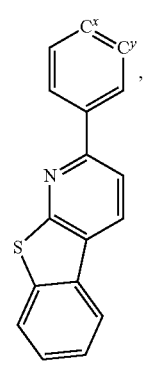
A14
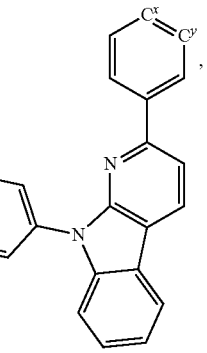
A15
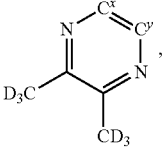
A16
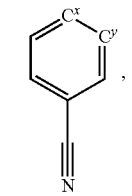
A17

A18
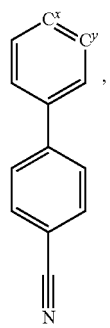
A19
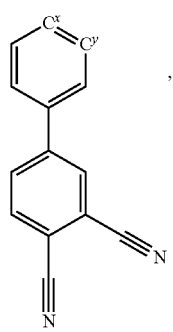
A20
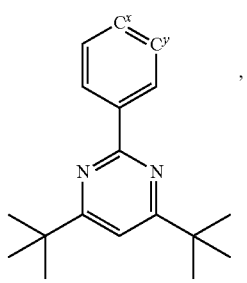
A21
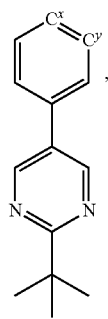
A22
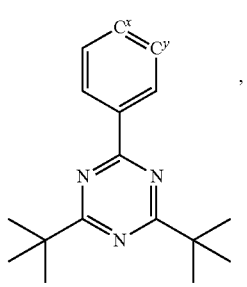
A23
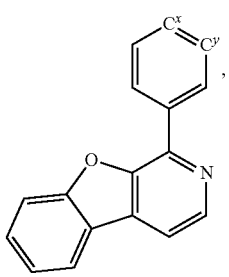
A24
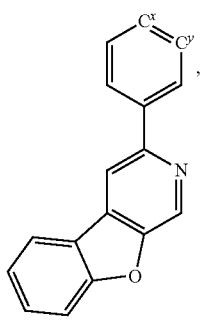
A25
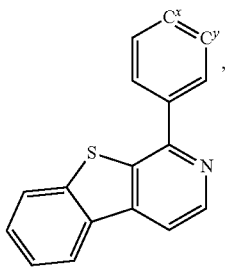
A26
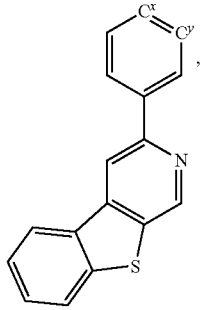
A27
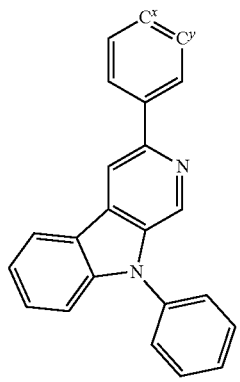

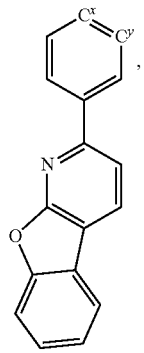
A28

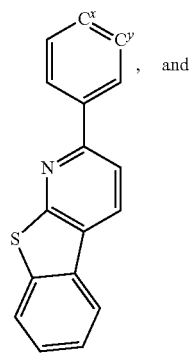
A29, and

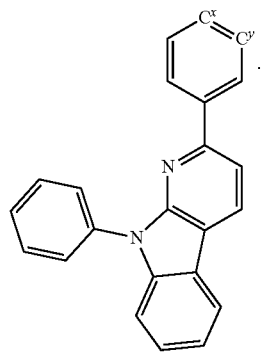
A30

The advantage of using tetraphenylene core for TADF is that multiple emissive states having close energies can be created. Such TADF emitter normally will have faster transient lifetime than a single charge transfer state type emitter. This can be achieved by having at least two donors and one acceptor or two acceptors and one donor in one molecule. These charge transfer states will mix together and lead to emitting states that can have larger radiative rates than a state made from energetically equal donor and acceptor units. The tetraphenylene core is rigid and allows for connection of multiple donor or acceptor units in close proximity. Further, the large spatial separation between the donor and acceptor units based on this core allow for the triplet energy to be high enough to be in the blue emitting region.

In some aspects described herein, an organic light emitting device (OLED) that includes an anode; a cathode; and an organic layer, disposed between the anode and cathode is disclosed. In some embodiments, the organic layer includes a compound of Formula I as described herein.

In some embodiments, the organic layer is a blocking layer and the compound is a blocking material in the organic layer. In some embodiments, the organic layer is a transporting layer and the compound is a transporting material in the organic layer.

In some embodiments, the organic layer is an emissive layer and the compound is an emitter. In some such embodiments, the OLED emits a luminescent radiation at room temperature when a voltage is applied across the first organic light emitting device; and the luminescent radiation comprises a delayed fluorescent process. In some emissive layer embodiments, the emissive layer further comprises a first phosphorescent emitting material. In some emissive layer embodiments, the emissive layer further comprises a second phosphorescent emitting material.

In some emissive layer embodiments, the OLED emits a white light at room temperature when a voltage is applied across the organic light emitting device. In some white light emitting embodiments, the compound emits a blue light having a peak wavelength between about 400 nm to about 500 nm. In some white light emitting embodiments, the compound emits a yellow light having a peak wavelength between about 530 nm to about 580 nm. In some emissive layer embodiments, the organic layer further comprises a sensitizer, and the sensitizer is a phosphorescent emitting material.

In some embodiments, the organic layer further comprises a phosphorescent emitting material comprising a metal atom selected from the group consisting of Os, Ir, Pd, Pt, Cu, and Au. In some embodiments, the phosphorescent emitting material further comprises at least one ligand selected from the group consisting of

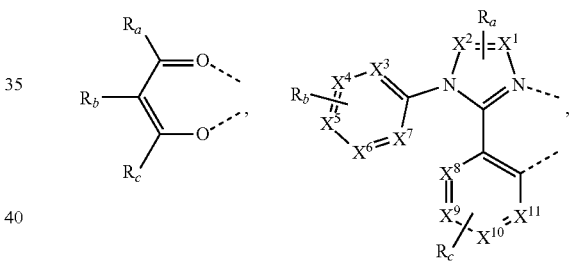

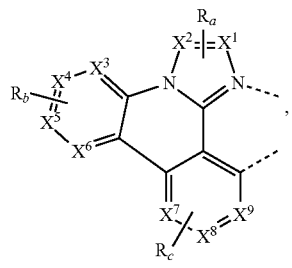

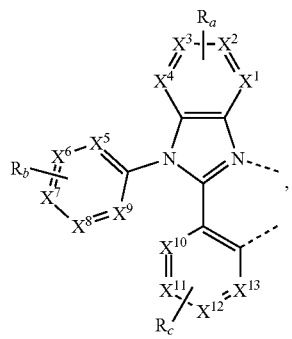

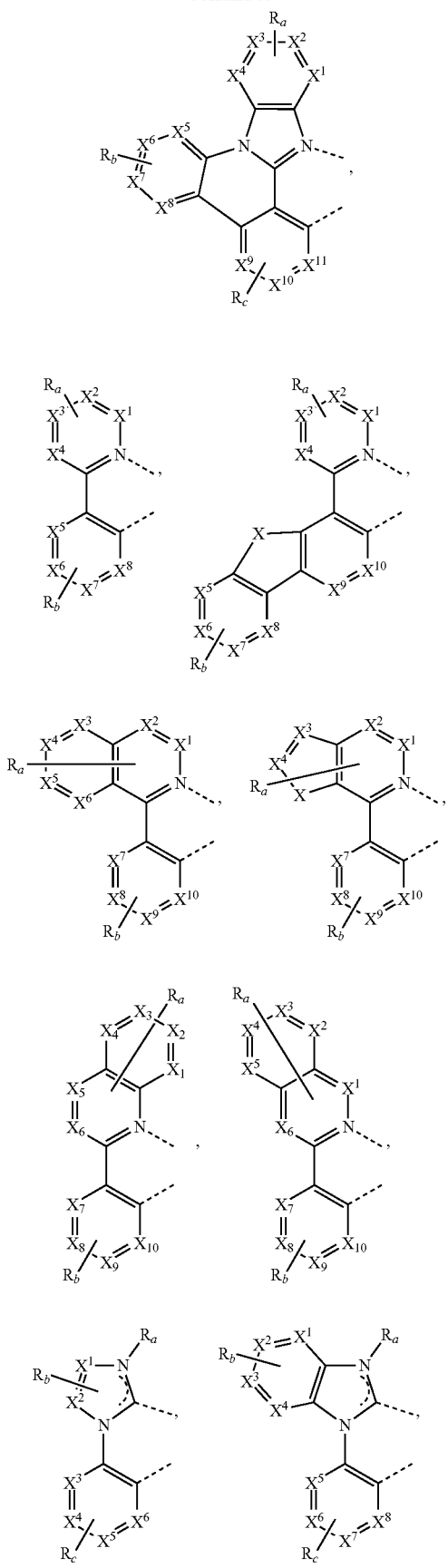
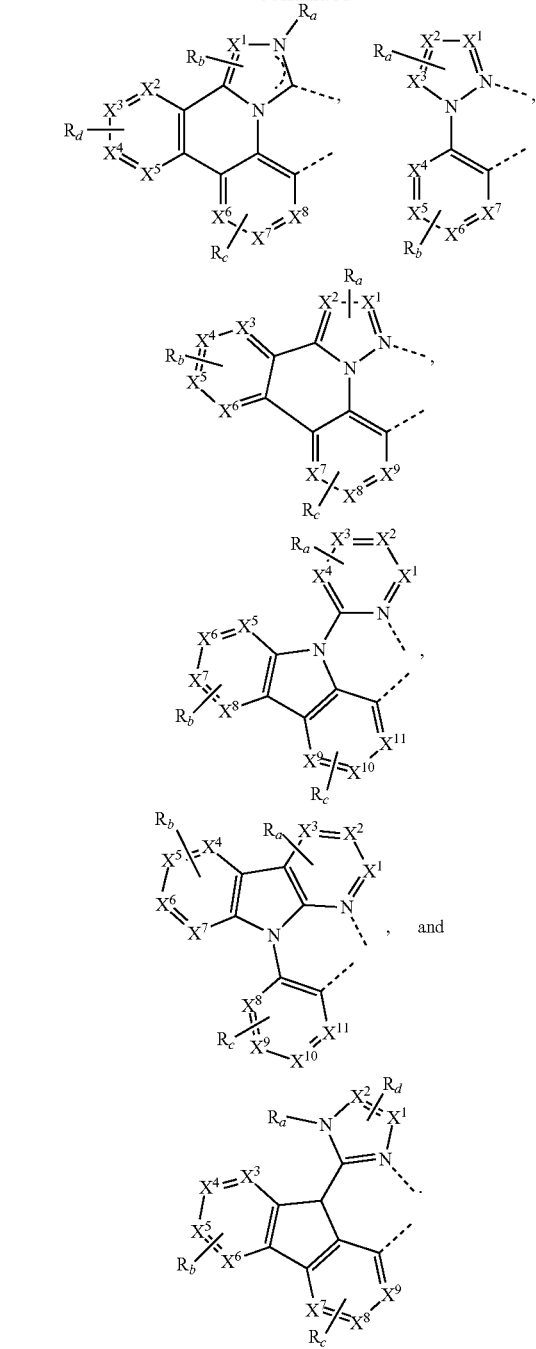

In the ligand structures above:
each $X^1$ to $X^{13}$ are independently selected from the group consisting of carbon and nitrogen;
X is selected from the group consisting of BR', NR', PR', O, S, Se, C=O, S=O, $SO_2$, CR'R", SiR'R", and GeR'R";
R' and R" can be fused or joined to form a ring;
each $R_a$, $R_b$, $R_c$, and $R_d$ represents from a mono substitution to a maximum possible number of substitutions, or no substitution;
R', R", $R_a$, $R_b$, $R_c$, and $R_d$ are each independently selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two adjacent substituents of $R_a$, $R_b$, $R_c$, and $R_d$ can be fused or joined to form a ring or form a multidentate ligand.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, an emissive region in an organic light emitting device that includes a compound of Formula I as disclosed herein is provided. In some embodiments, the compound is an emissive dopant or a non-emissive dopant.

In some emissive region embodiments, the emissive region further comprises a host, wherein the host contains at least one group selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene. In some emissive region embodiments, the emissive region further comprises a host, wherein the host is selected from the group consisting of:

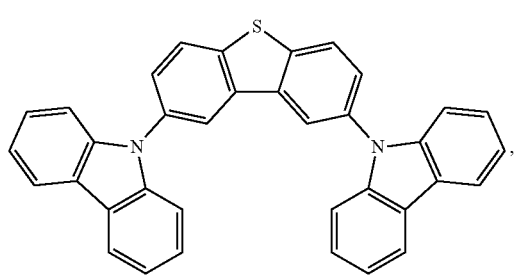

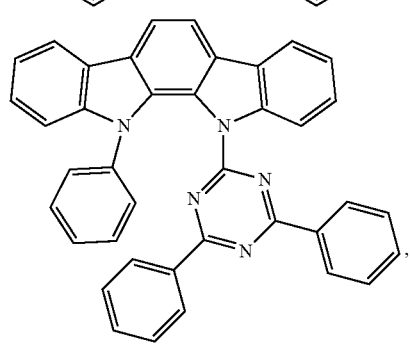

-continued

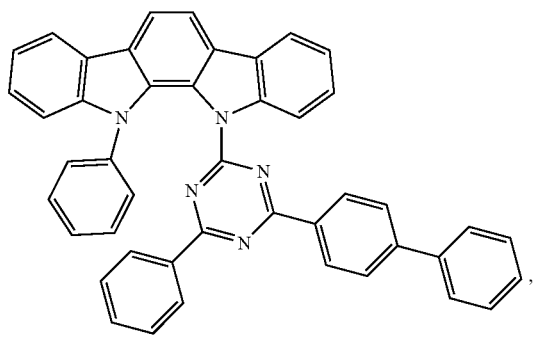

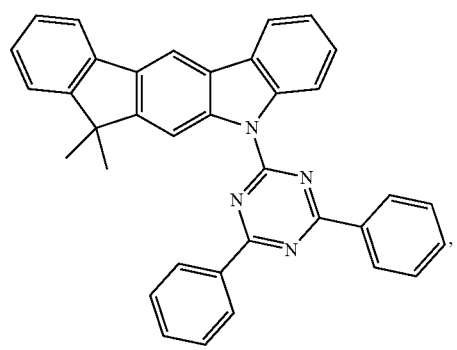

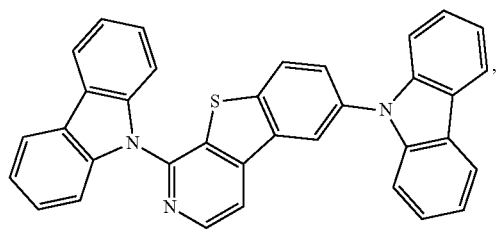

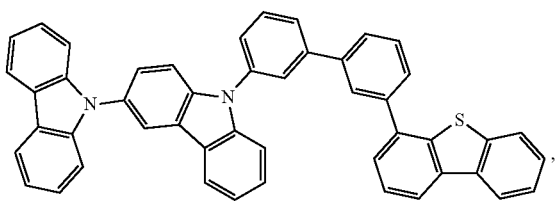

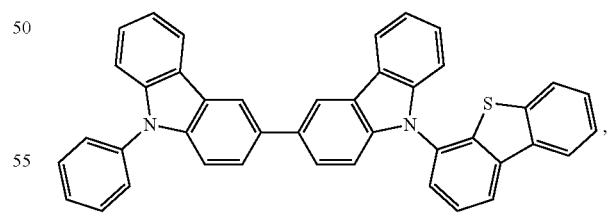

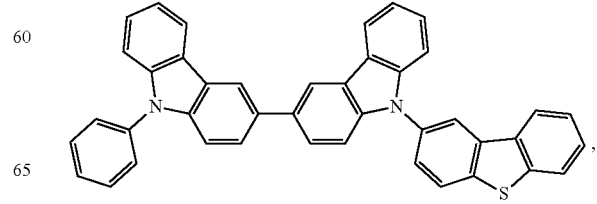

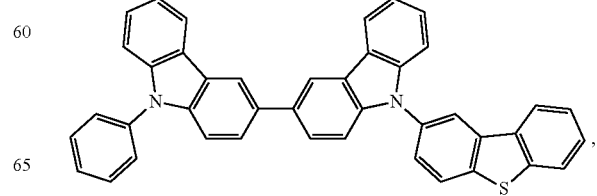

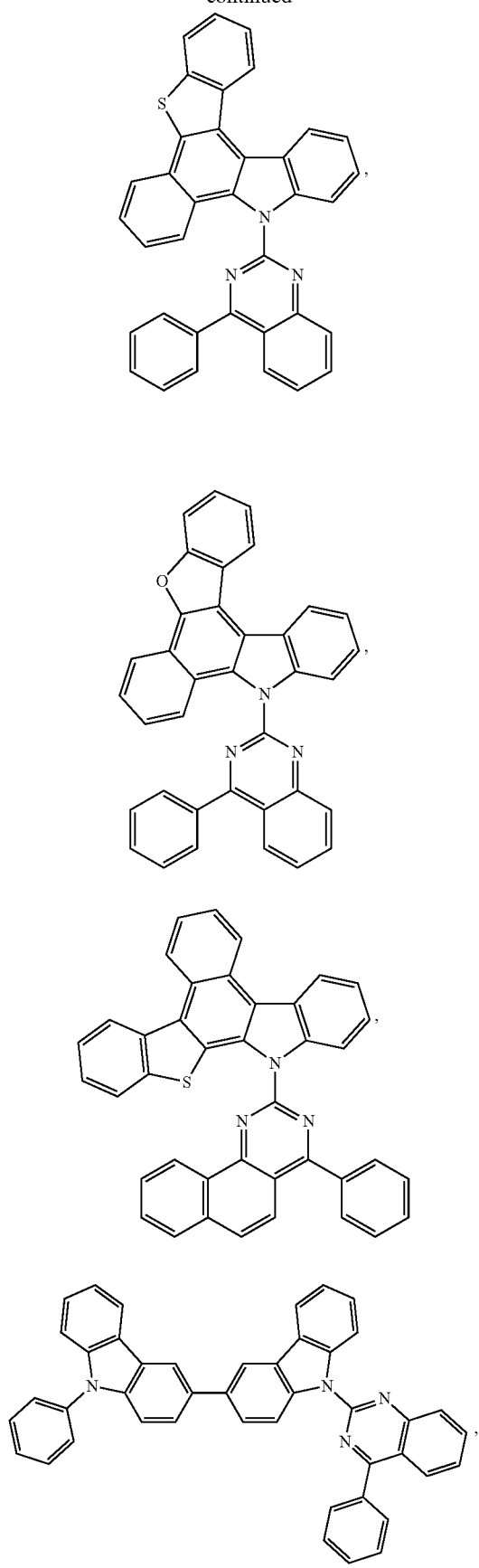

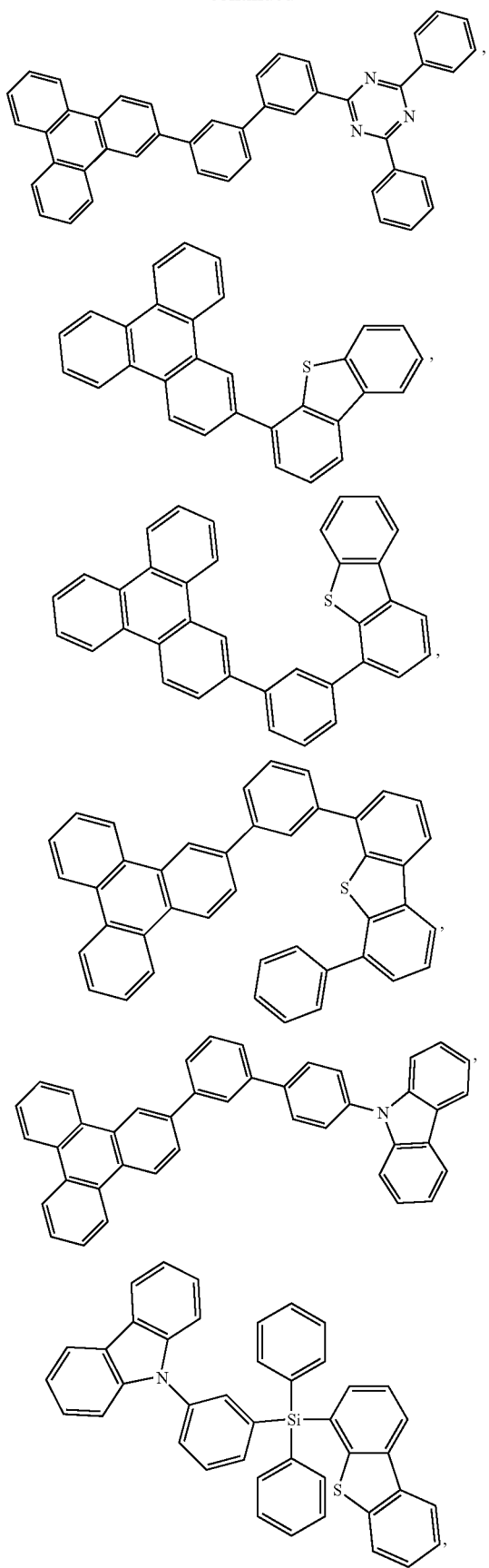
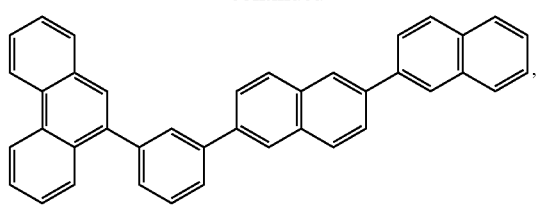
and combinations thereof.
In some emissive region embodiments, the emissive region further comprises a phosphorescent emissive dopant; wherein the emissive dopant is a transition metal complex having at least one ligand or part of the ligand if the ligand is more than bidentate selected from the group consisting of:
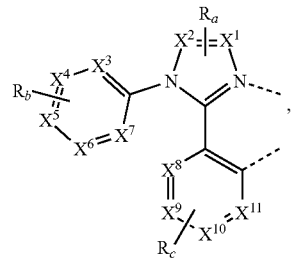
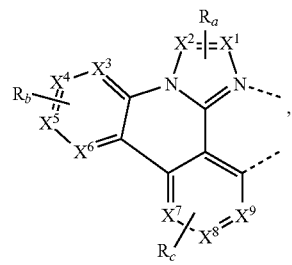
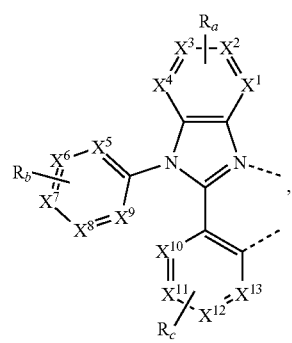
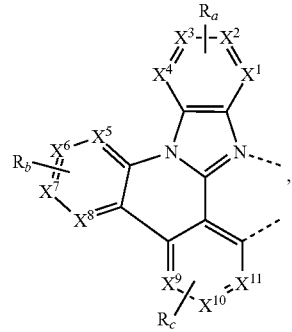

-continued

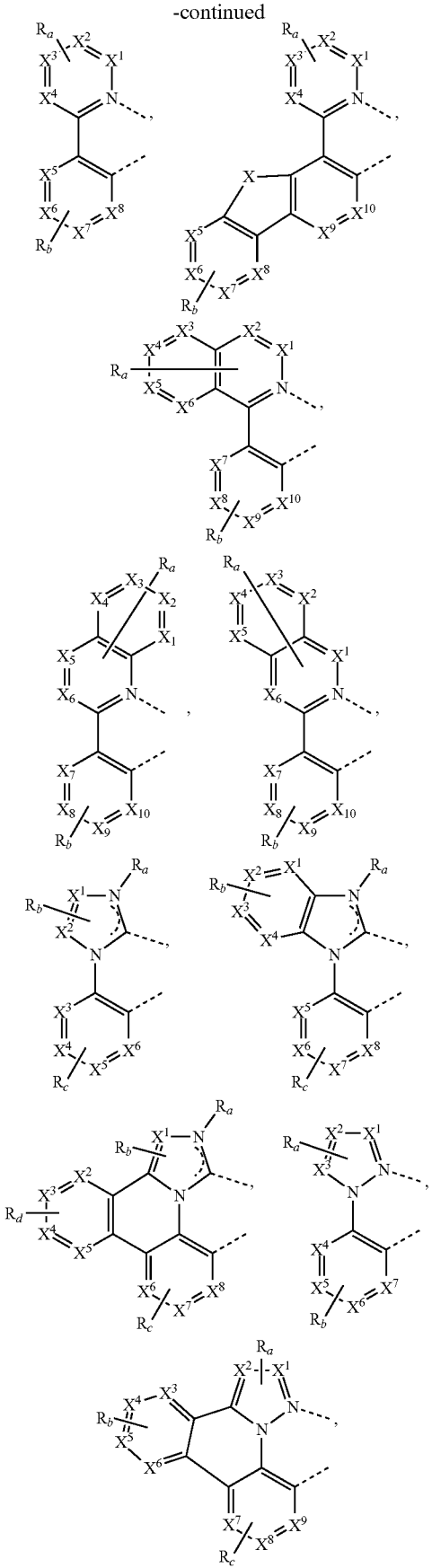

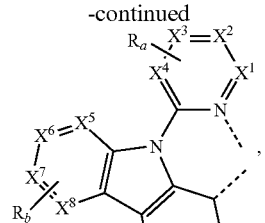

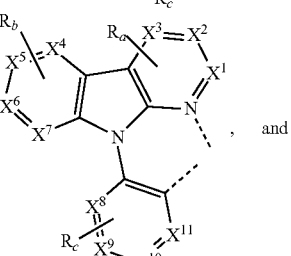

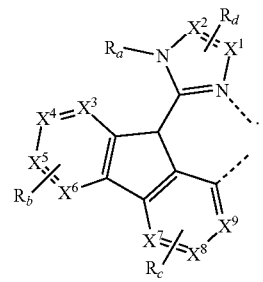

In the transition metal complex ligands above:
  each $X^1$ to $X^{13}$ are independently selected from the group consisting of carbon and nitrogen;
  X is selected from the group consisting of BR', NR', PR', O, S, Se, C=O, S=O, $SO_2$, CR'R", SiR'R", and GeR'R";
  R' and R" are optionally fused or joined to form a ring;
  R' and R" are each independently selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof;
  each $R_a$, $R_b$, $R_c$, and $R_d$ may represent from mono substitution to the possible maximum number of substitution, or no substitution;
  $R_a$, $R_b$, $R_c$, and $R_d$ are each independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof; and
  any two substituents of $R_a$, $R_b$, $R_c$, and $R_d$ are optionally fused or joined to form a ring or form a multidentate ligand.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. patent application Publication No. 2019/0081248, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others).

When there are more than one ligand coordinated to a metal, the ligands can all be the same in some embodiments. In some other embodiments, at least one ligand is different from the other ligand(s). In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiment, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

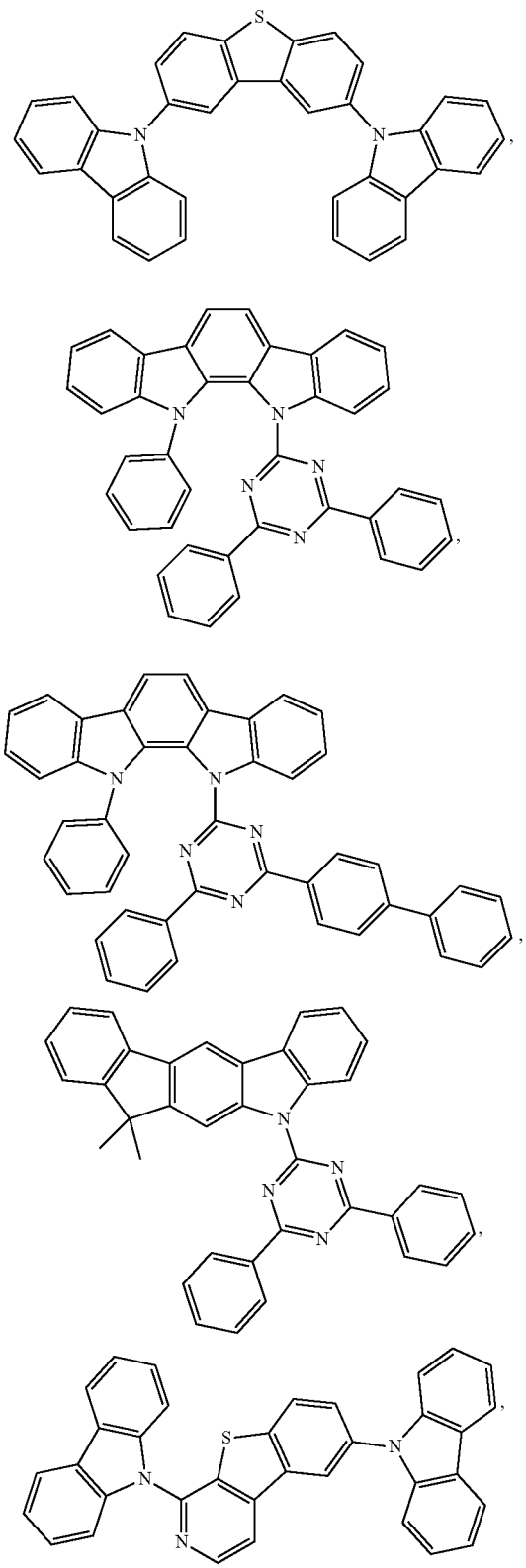

45
-continued
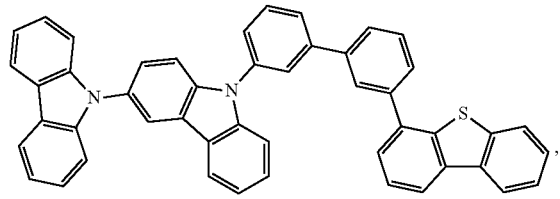
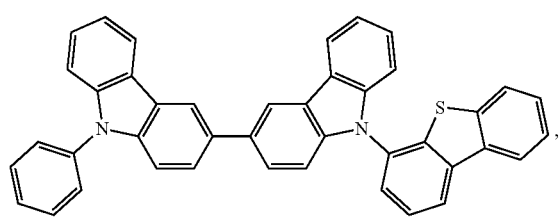
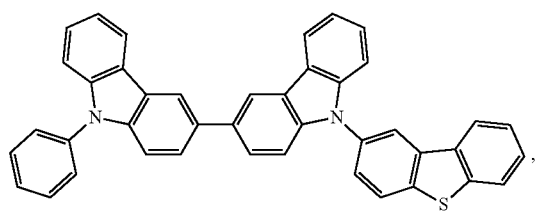
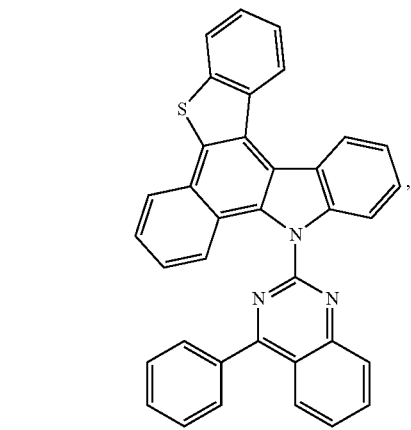
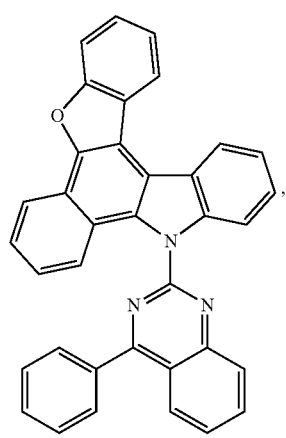
46
-continued
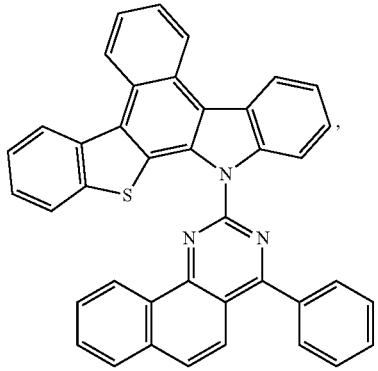
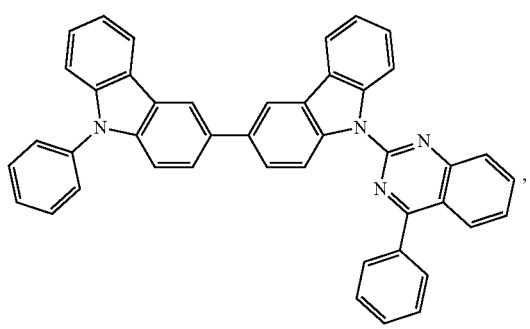
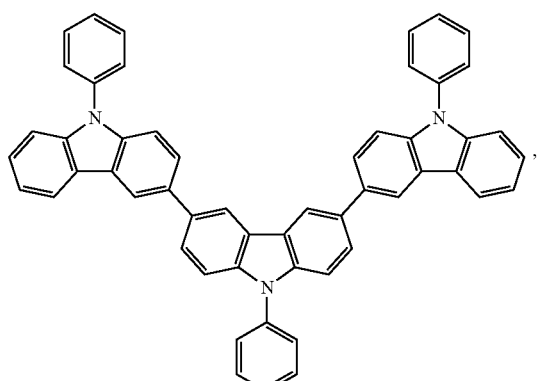
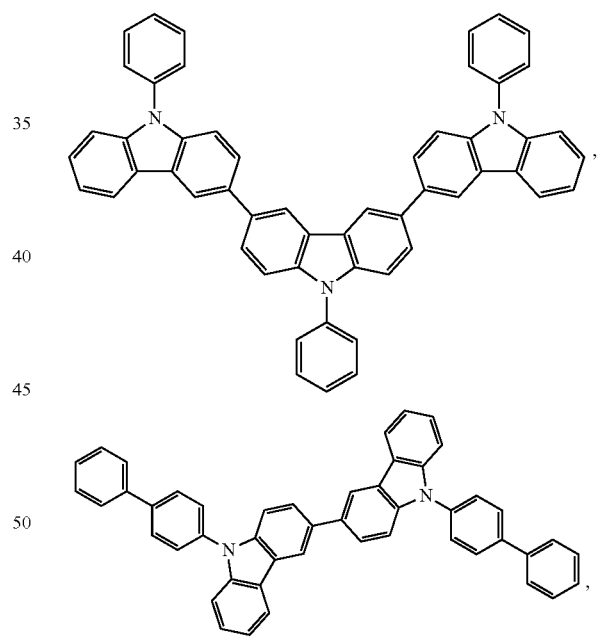
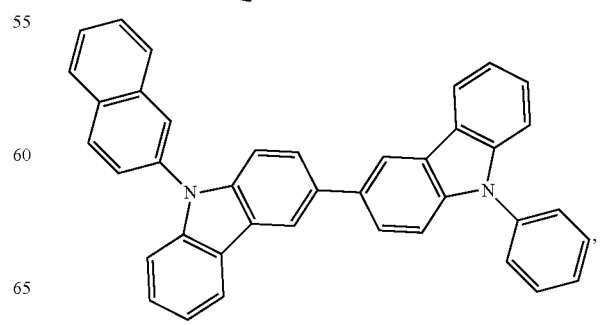

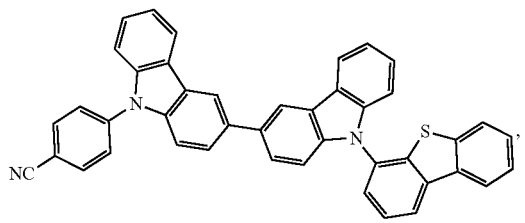

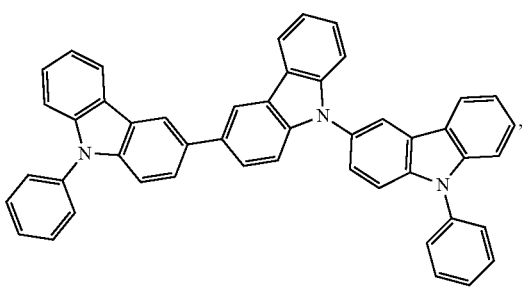

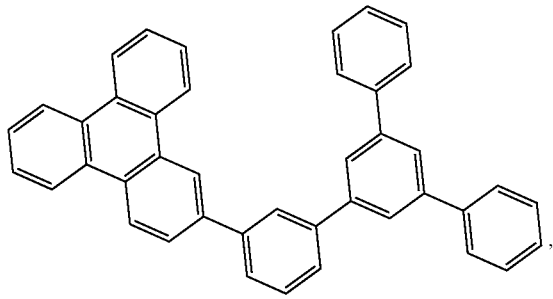

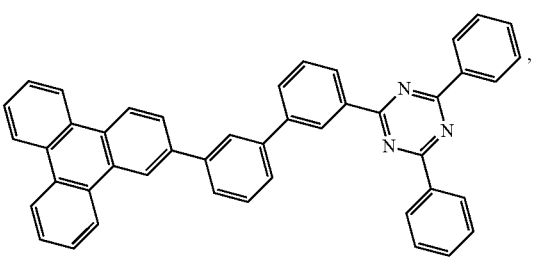

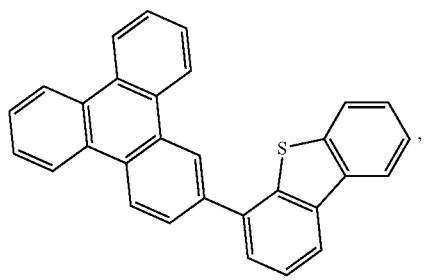

and combinations thereof.

Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds (e.g., via hydrogen bonding).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

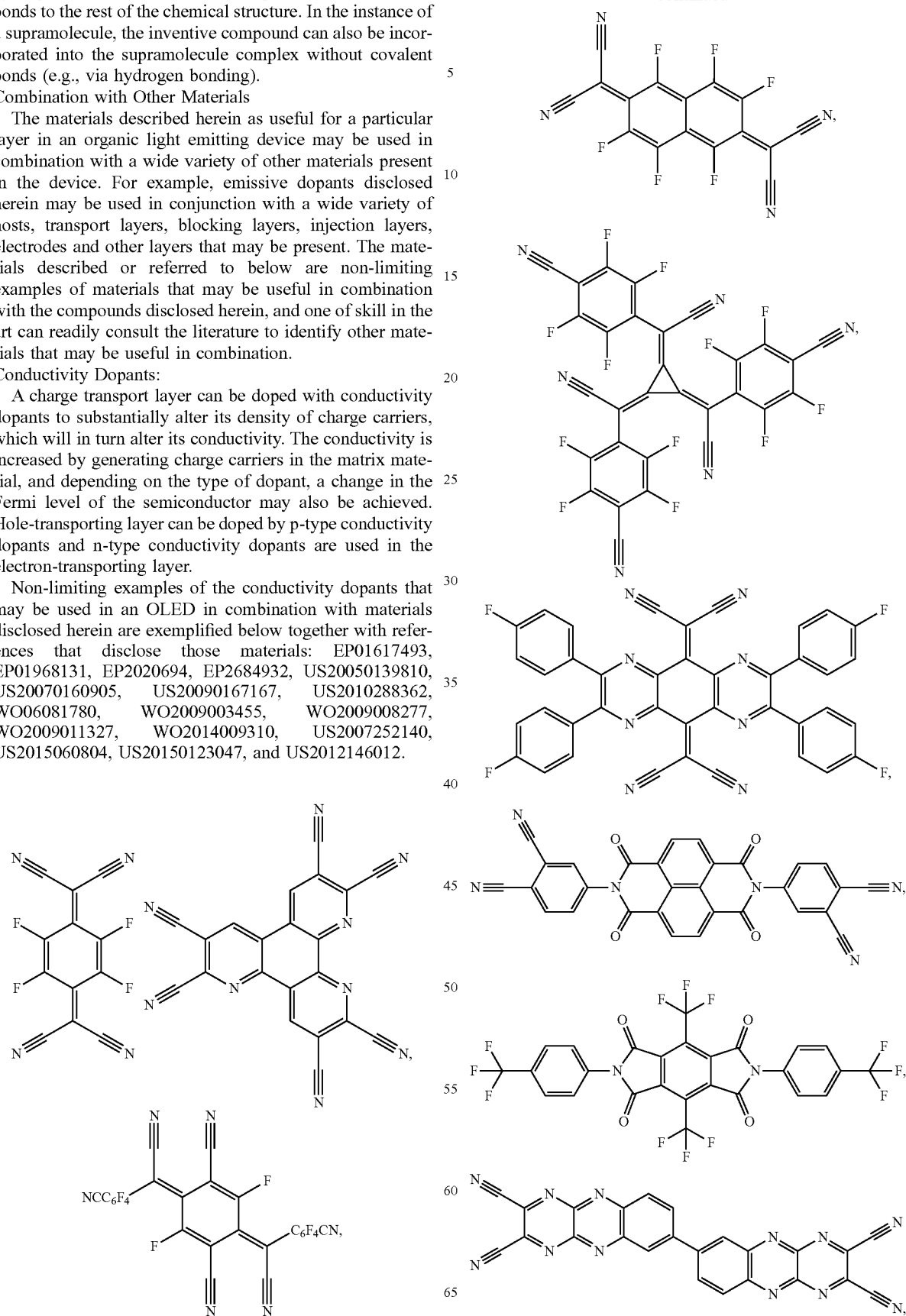

-continued

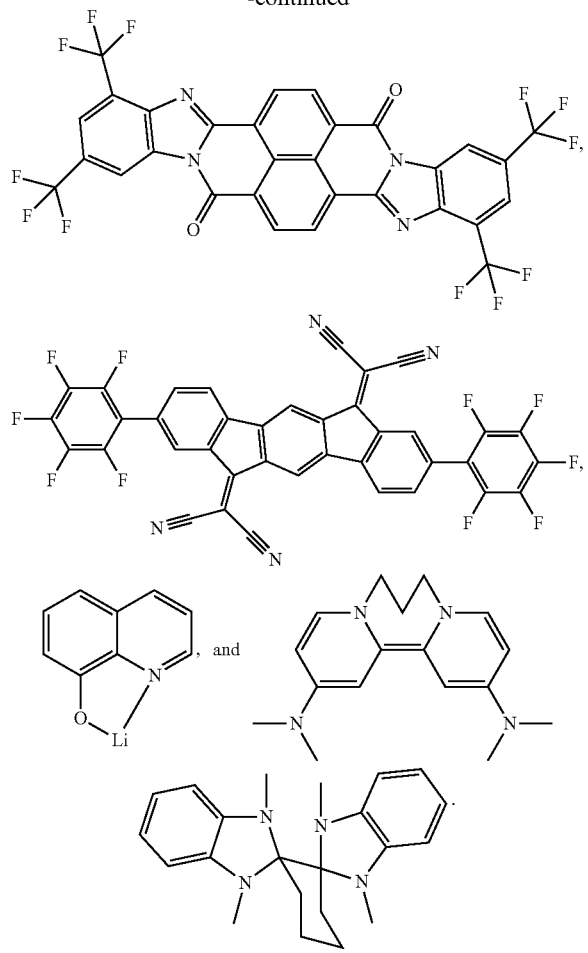

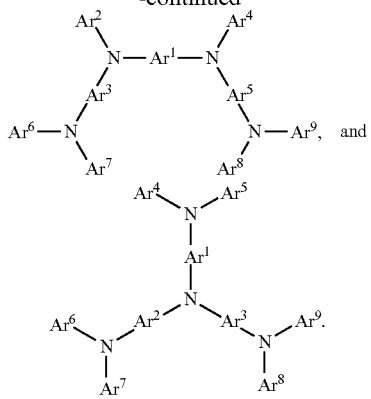

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

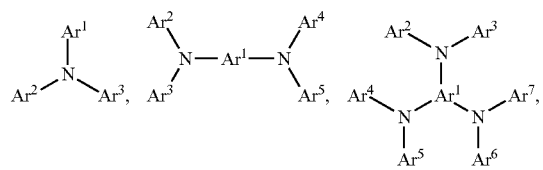

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

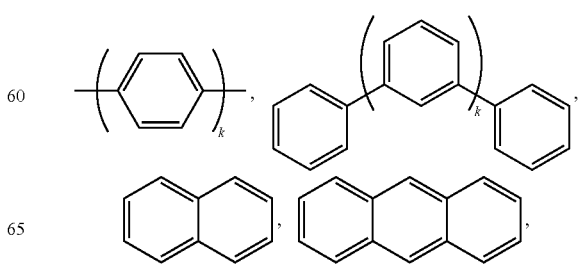

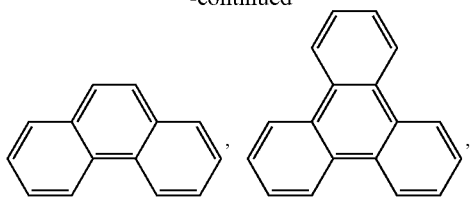

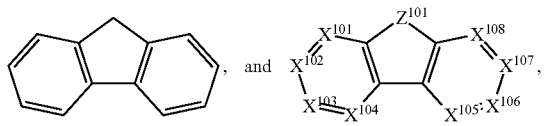

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

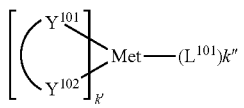

wherein Met is a metal, which can have an atomic weight greater than 40; $(Y^{101}-Y^{102})$ is a bidentate ligand, $Y^{111}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

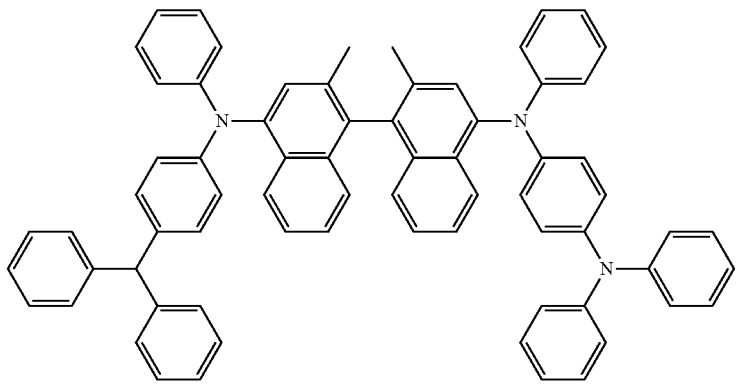

-continued
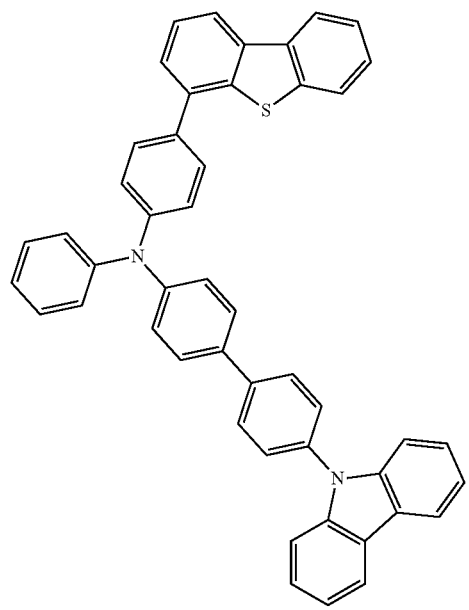
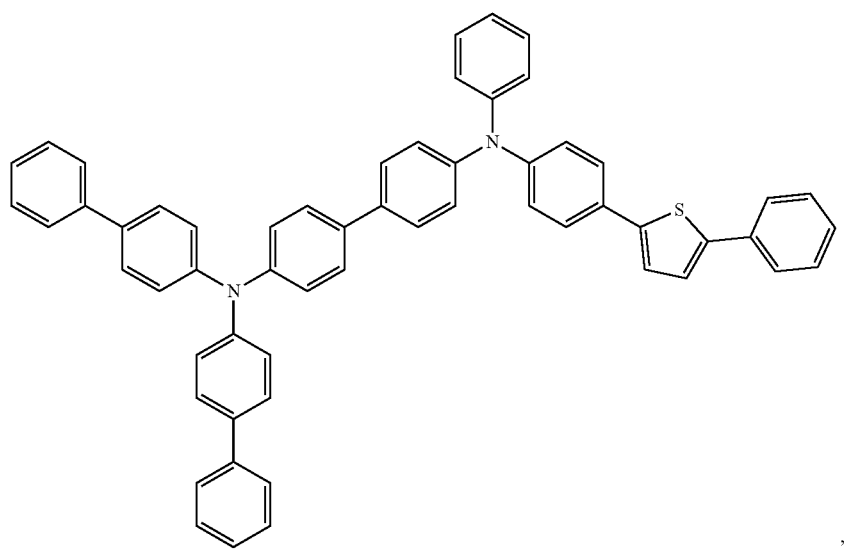
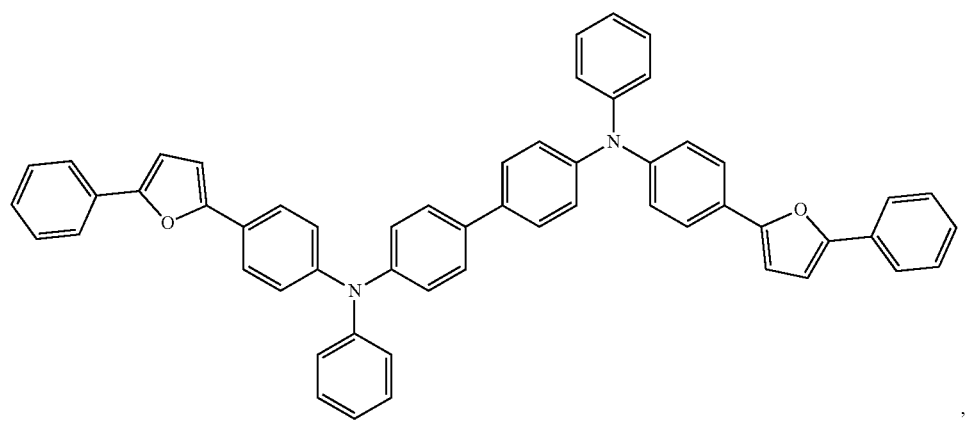

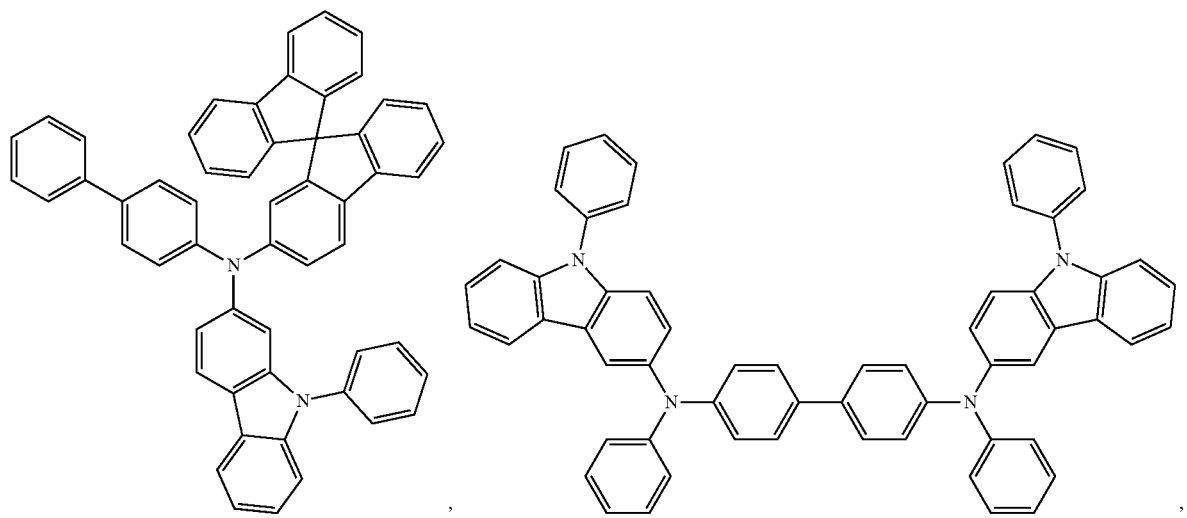
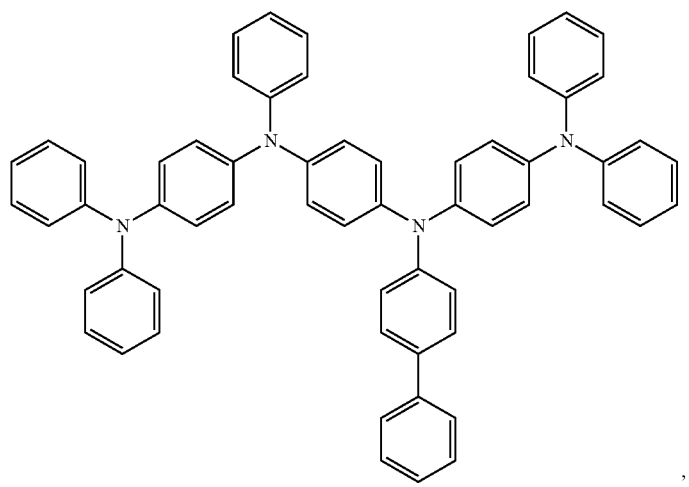
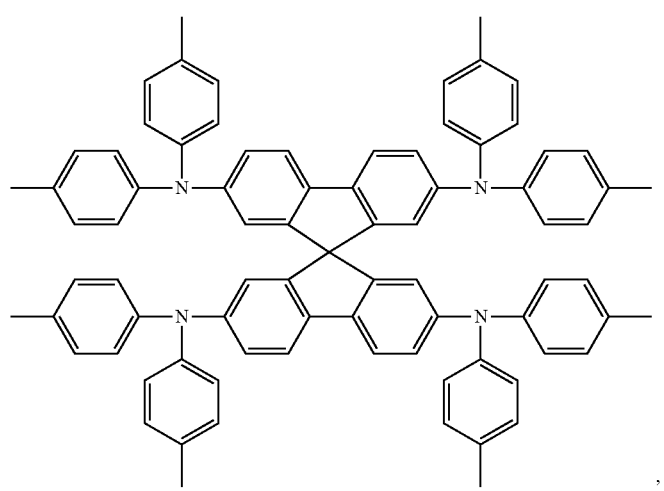

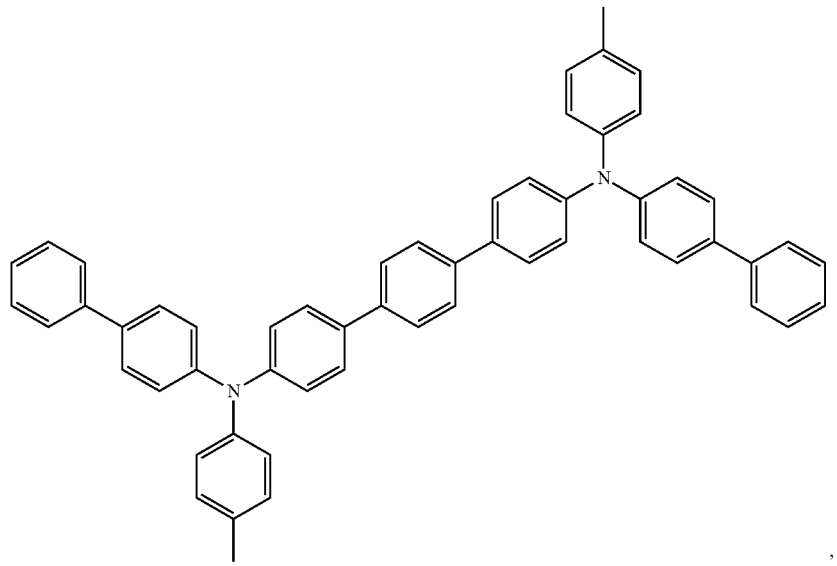
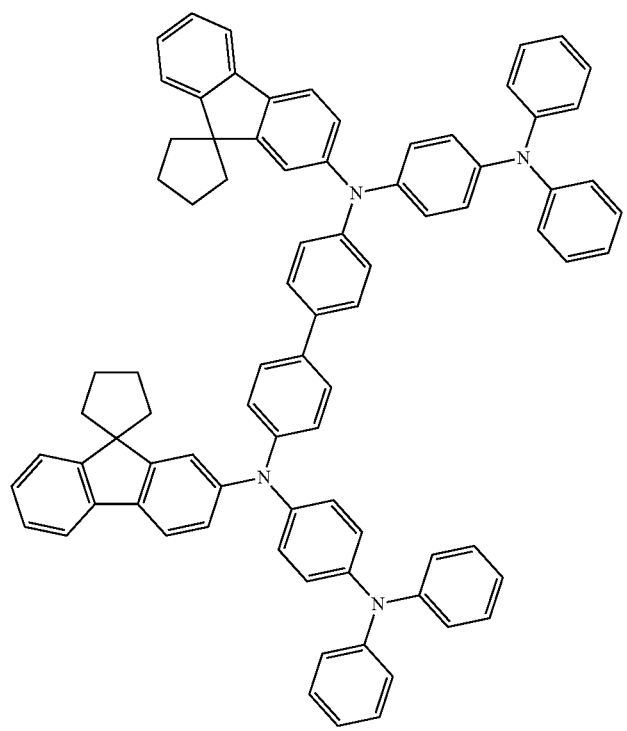
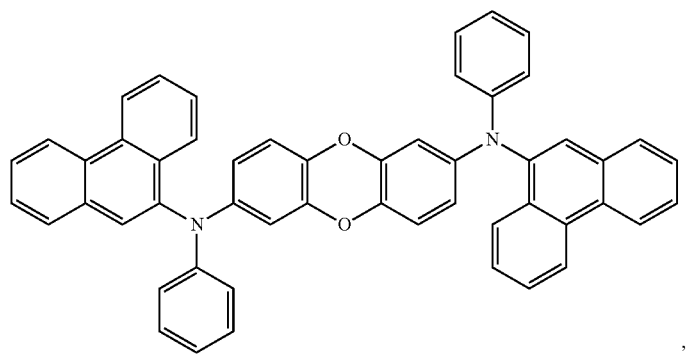

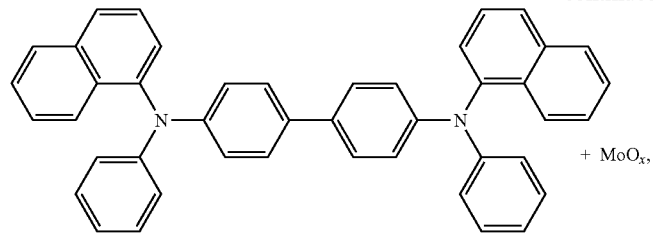
+ MoOx,
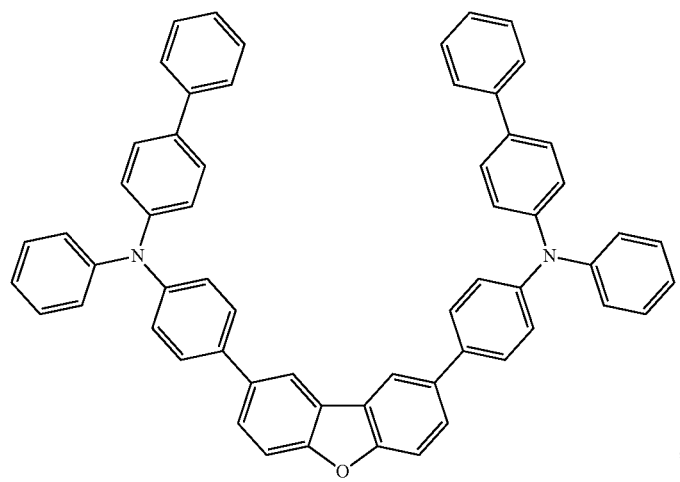
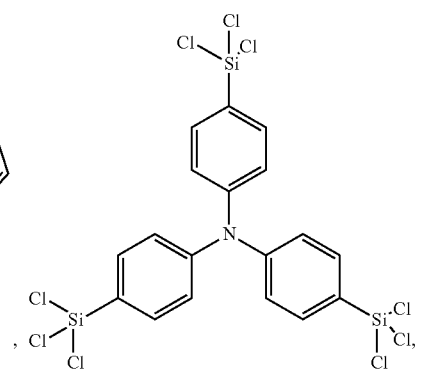
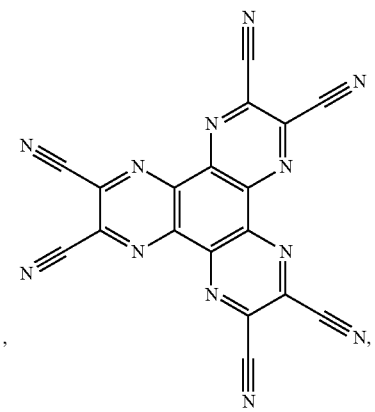
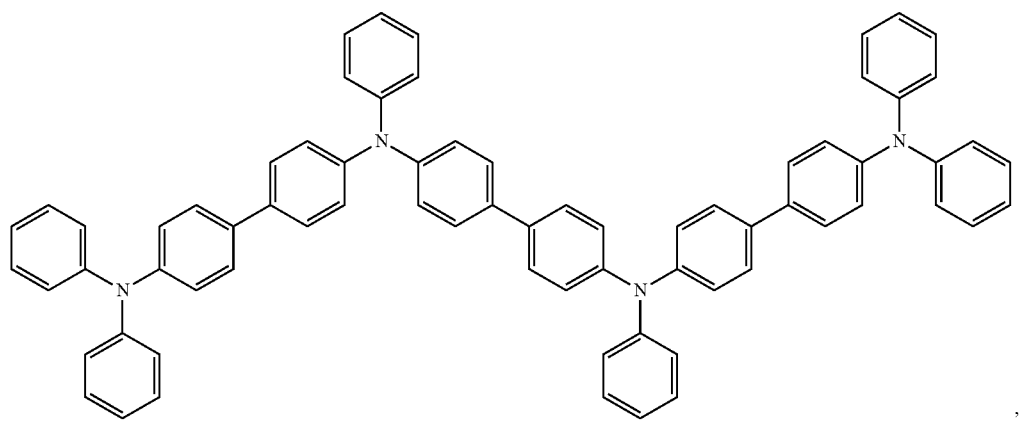

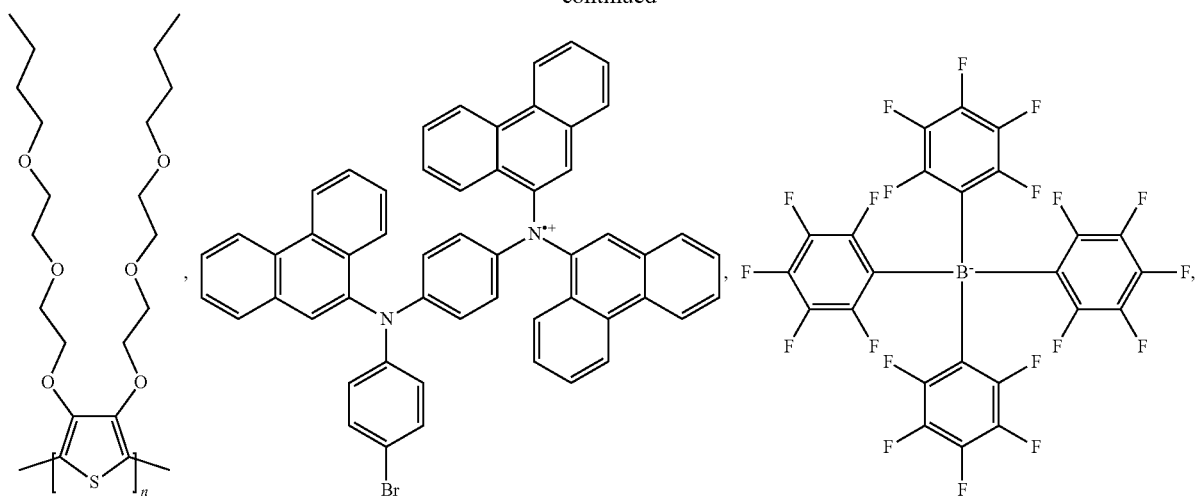
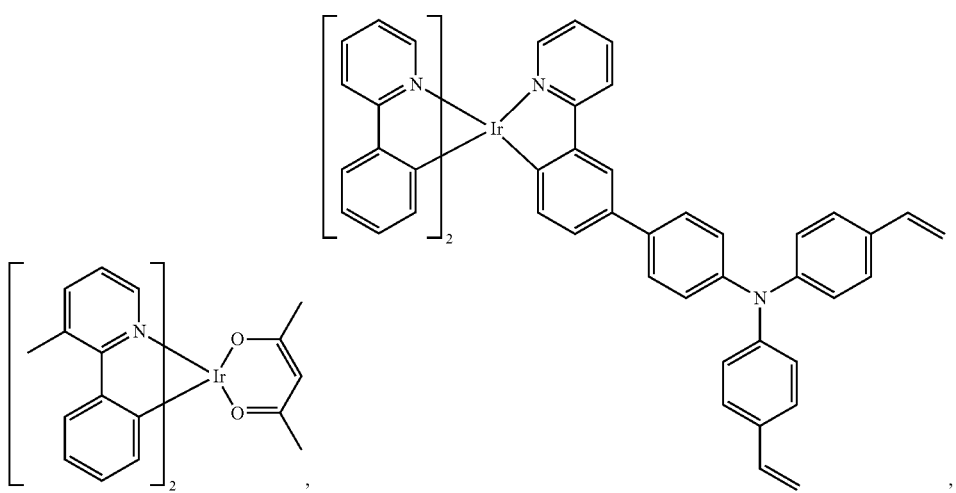
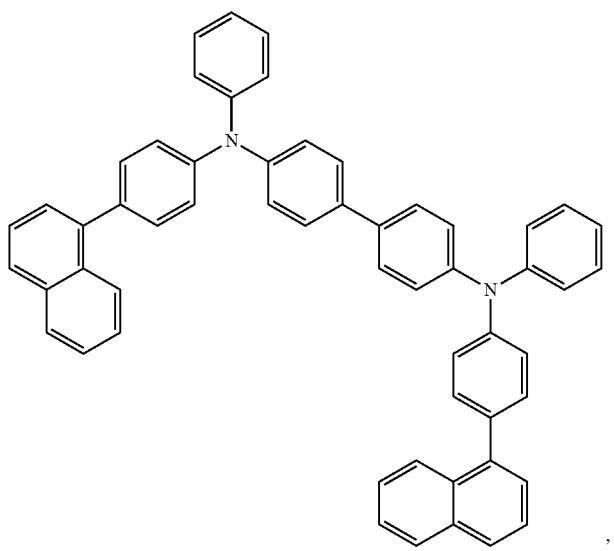

-continued
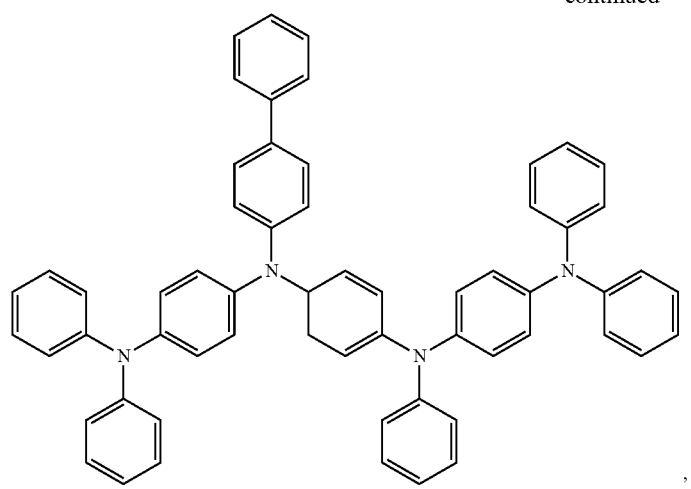
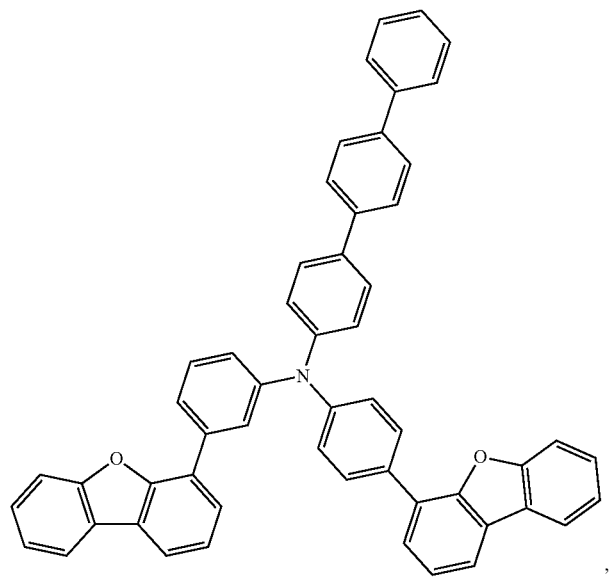
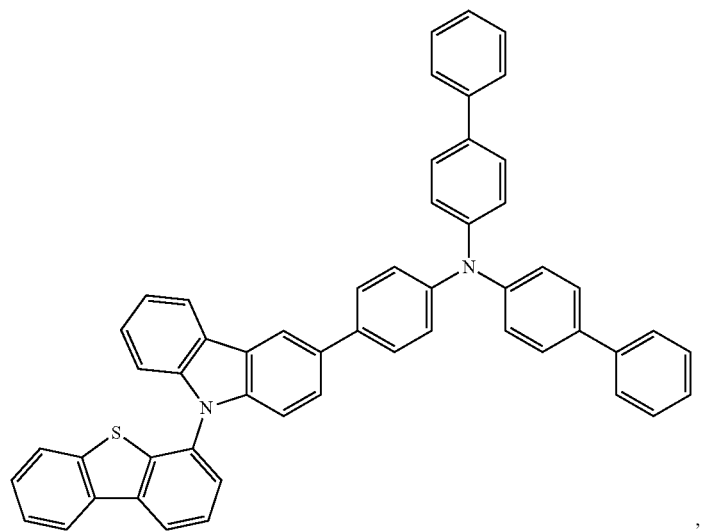

-continued
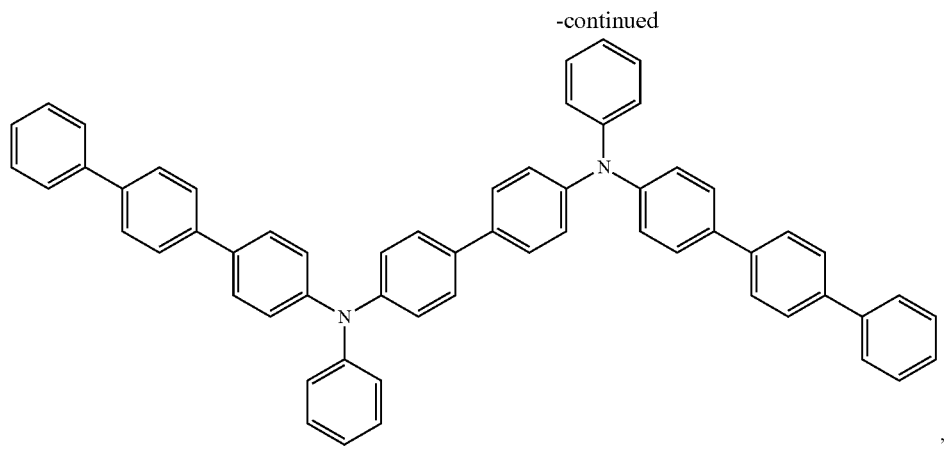
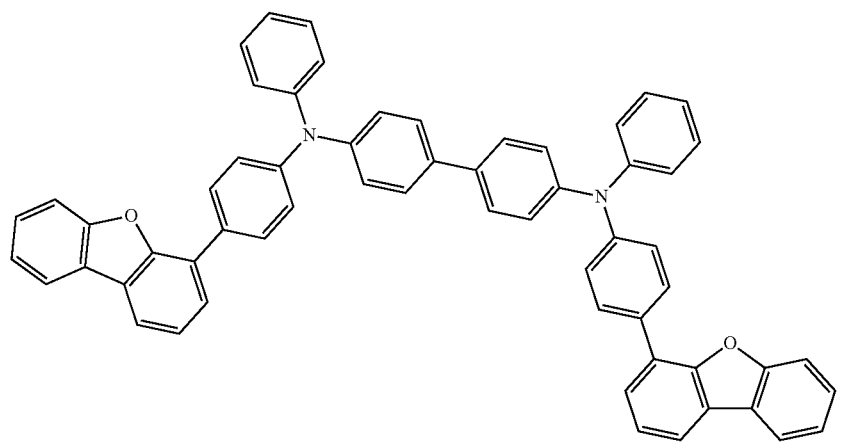
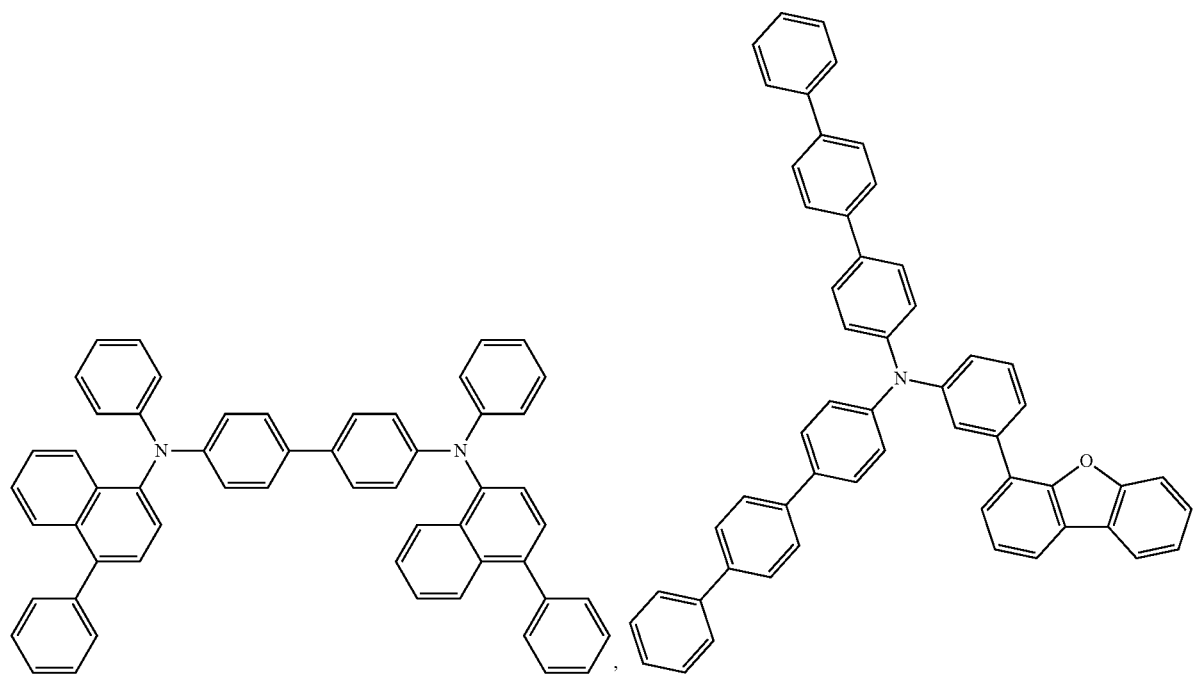

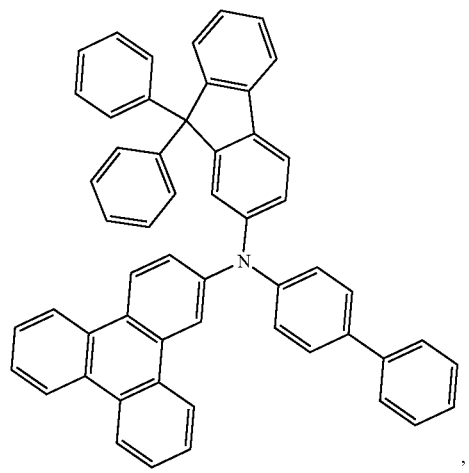
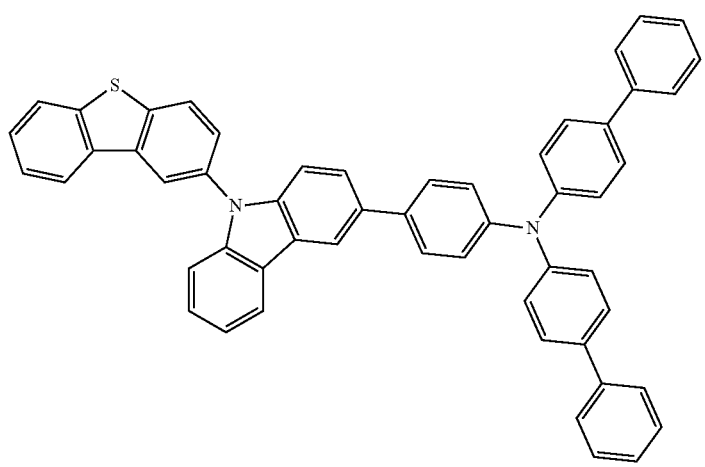
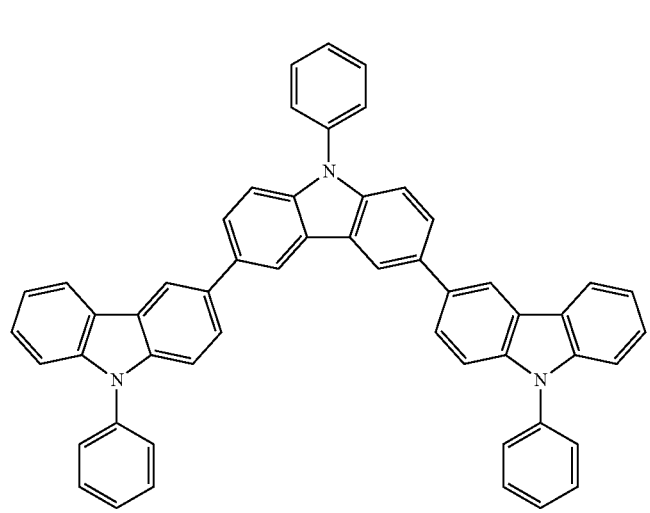
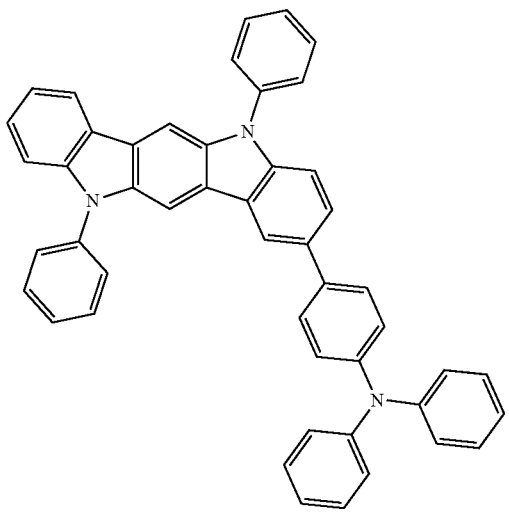
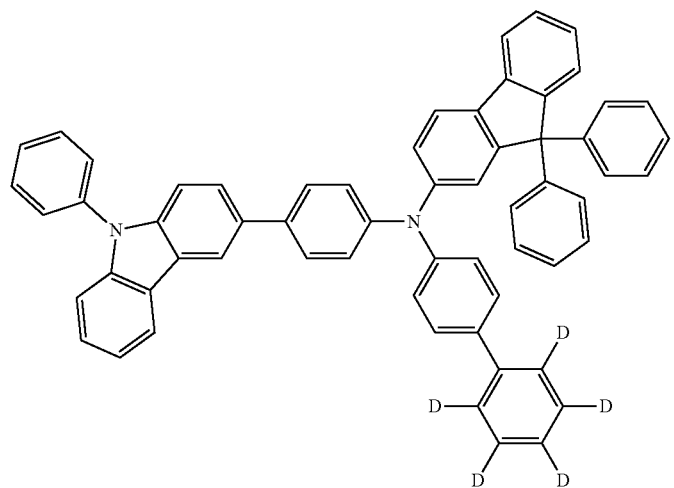

-continued
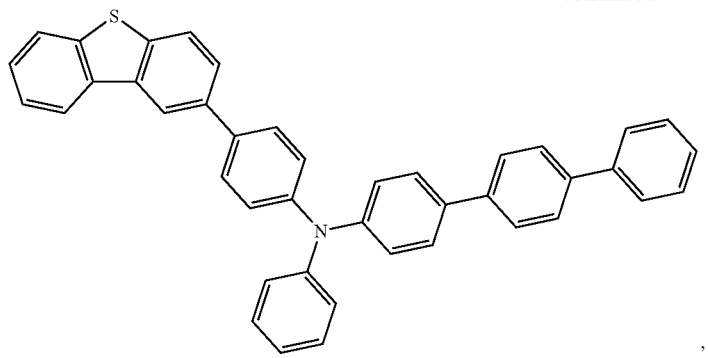
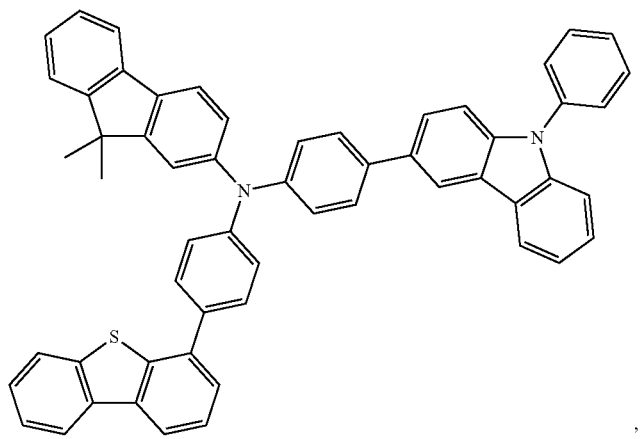
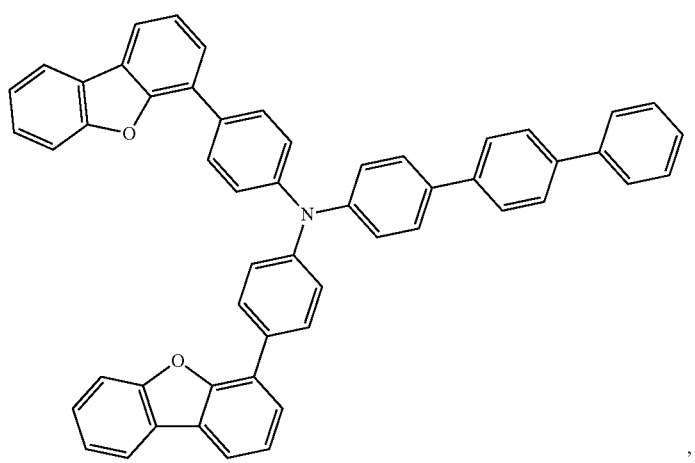

-continued
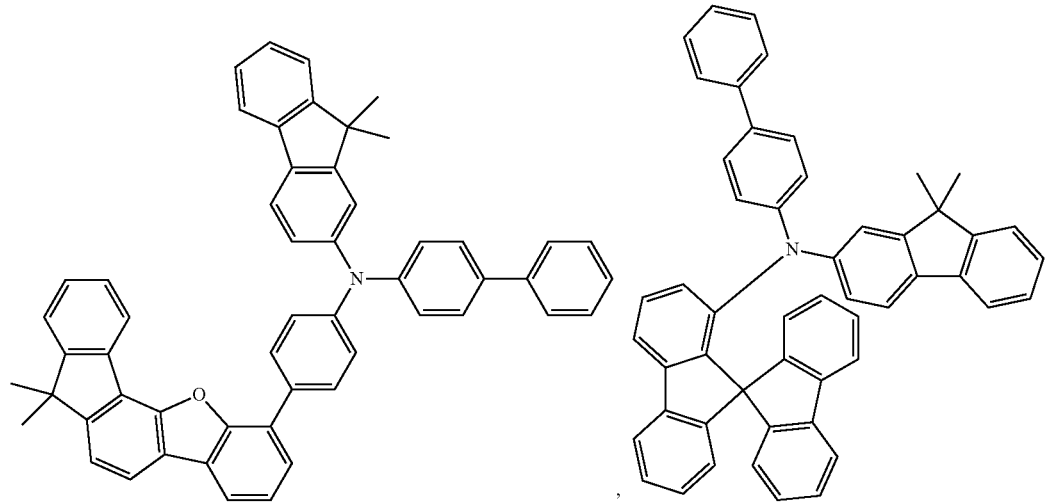
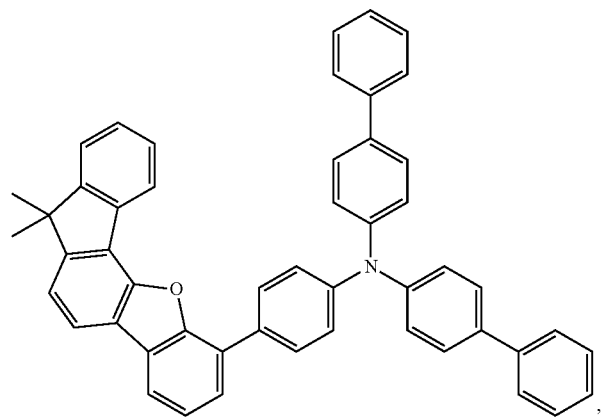
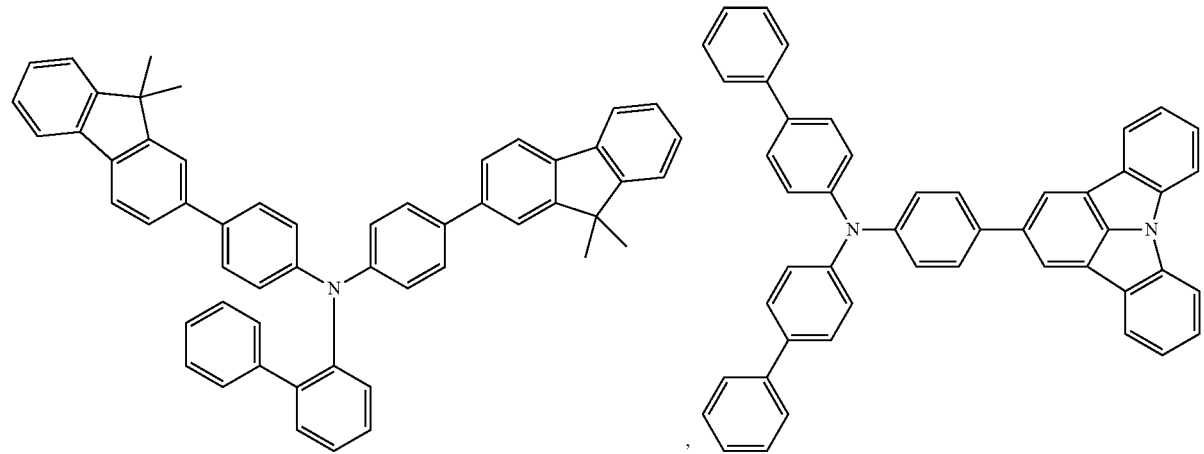

-continued
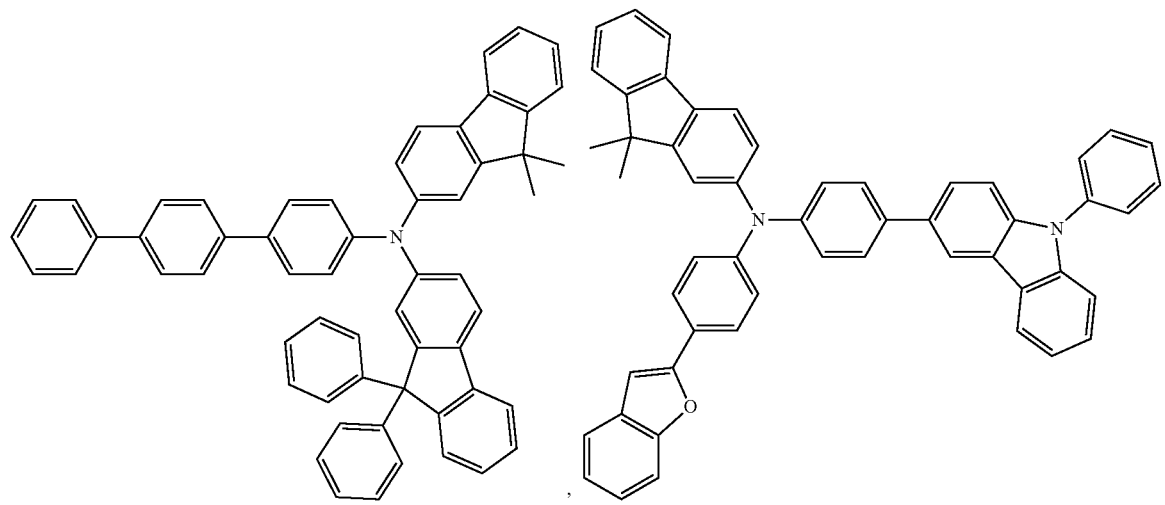
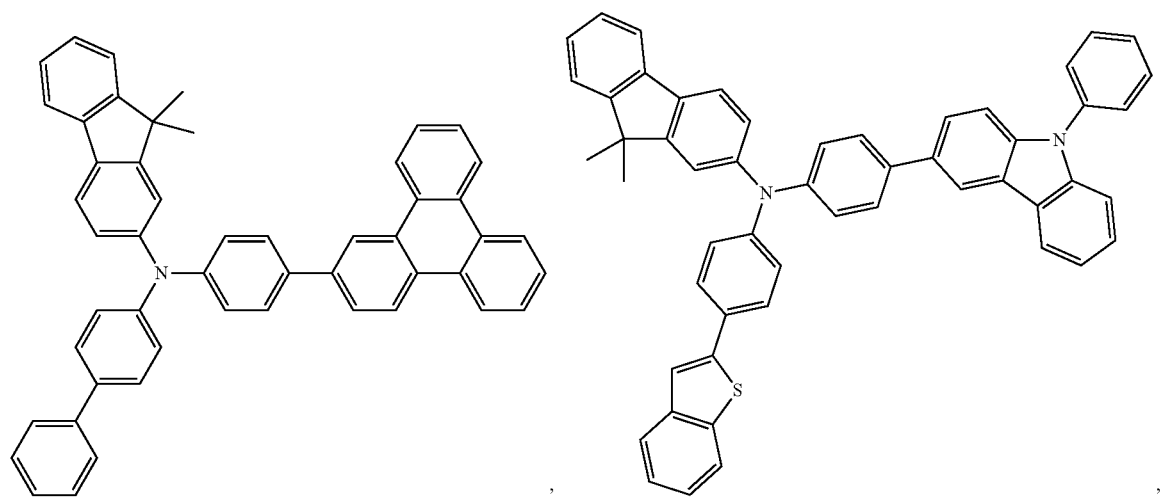
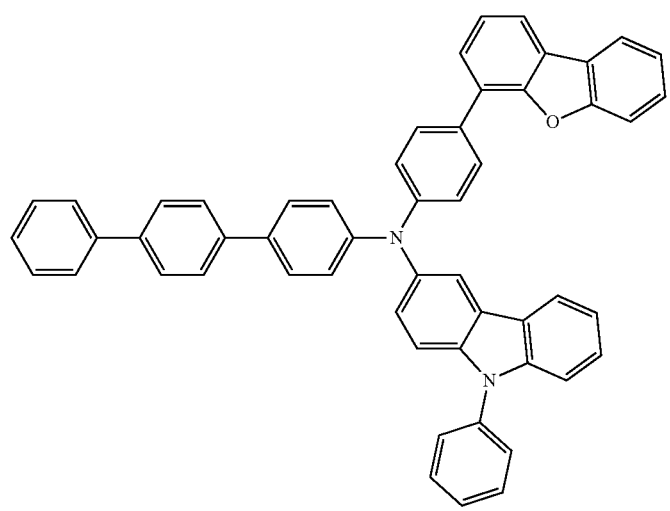

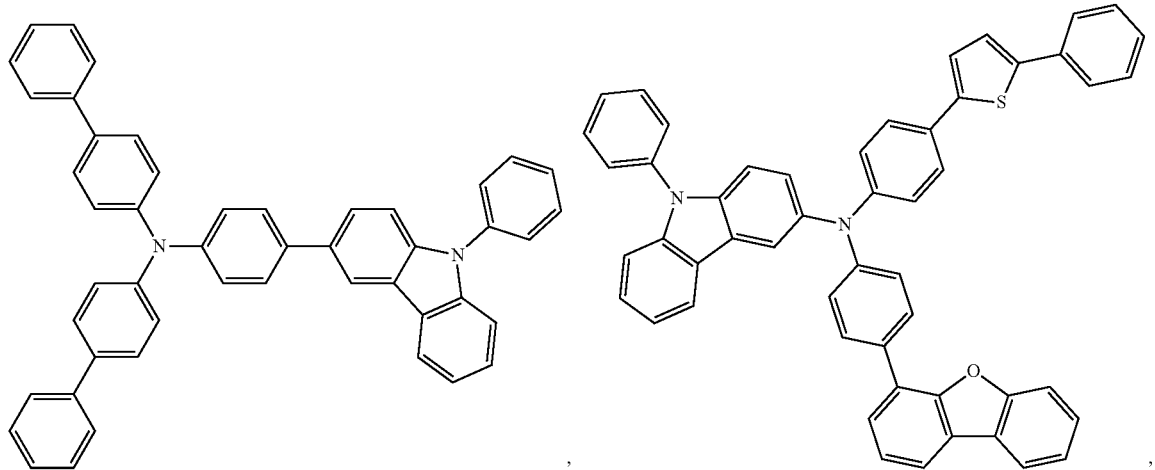
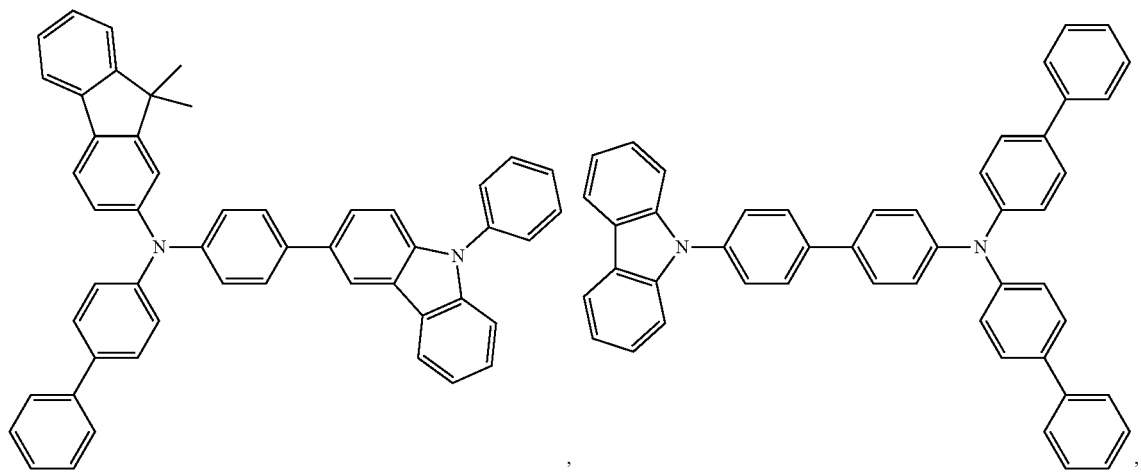
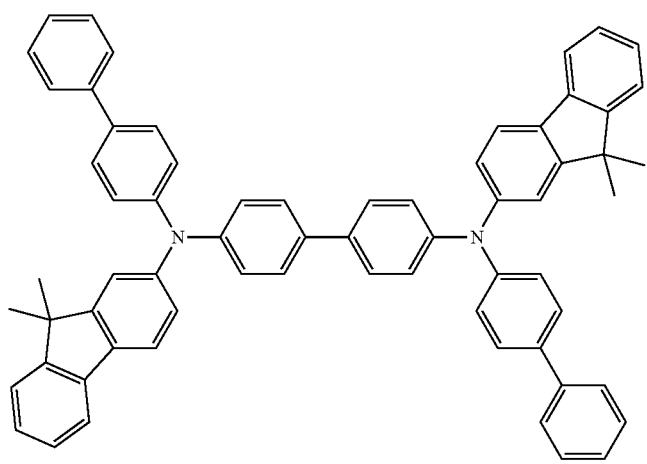

-continued
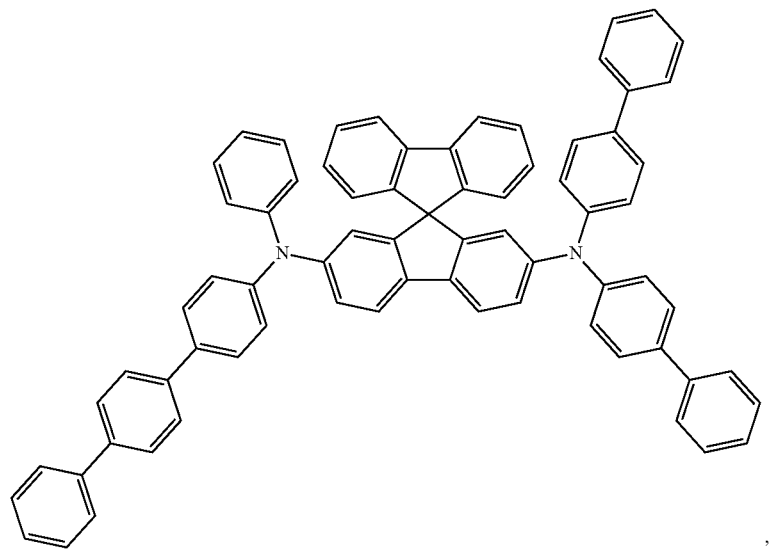
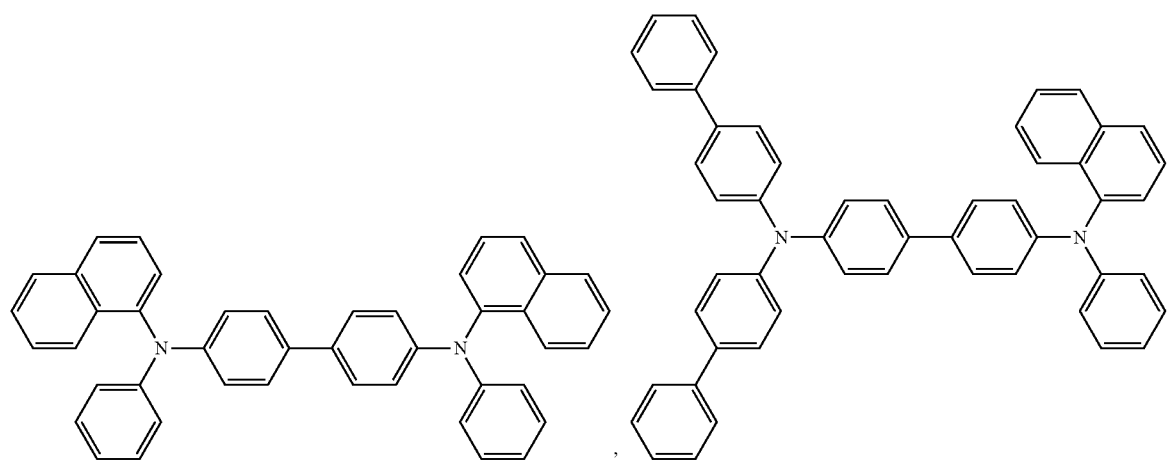
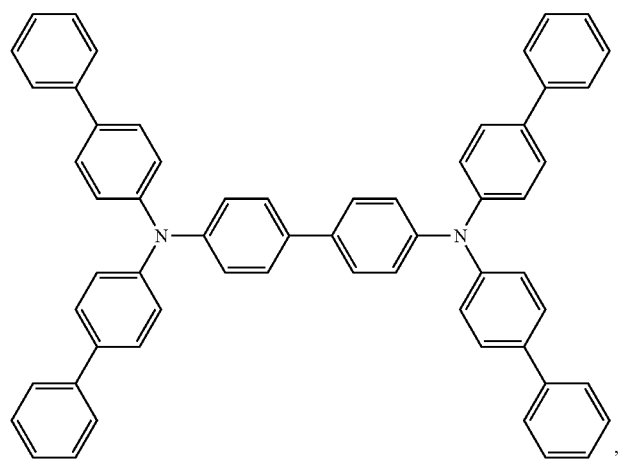

-continued
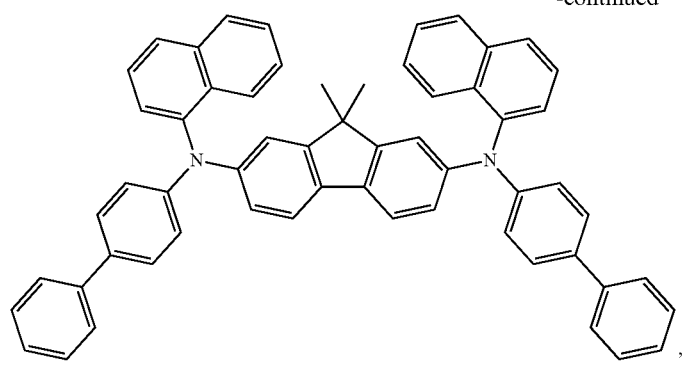
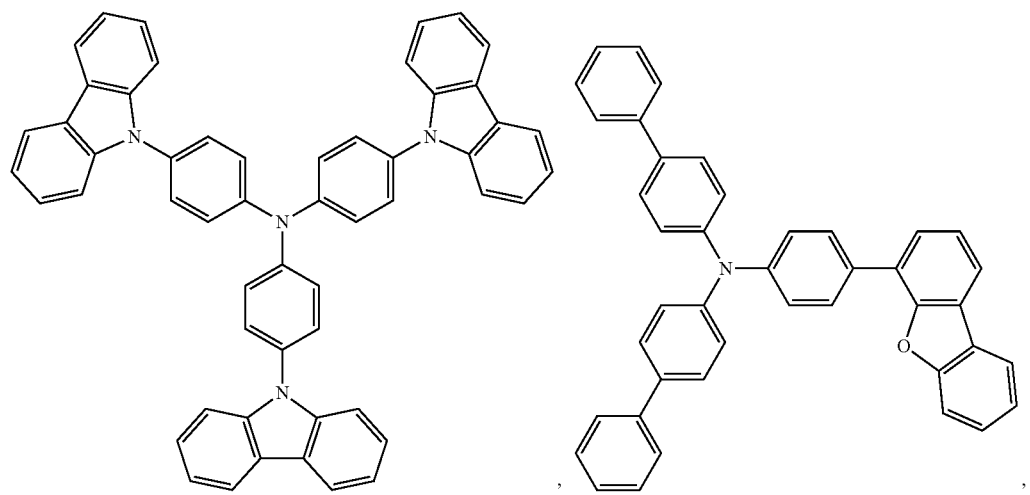
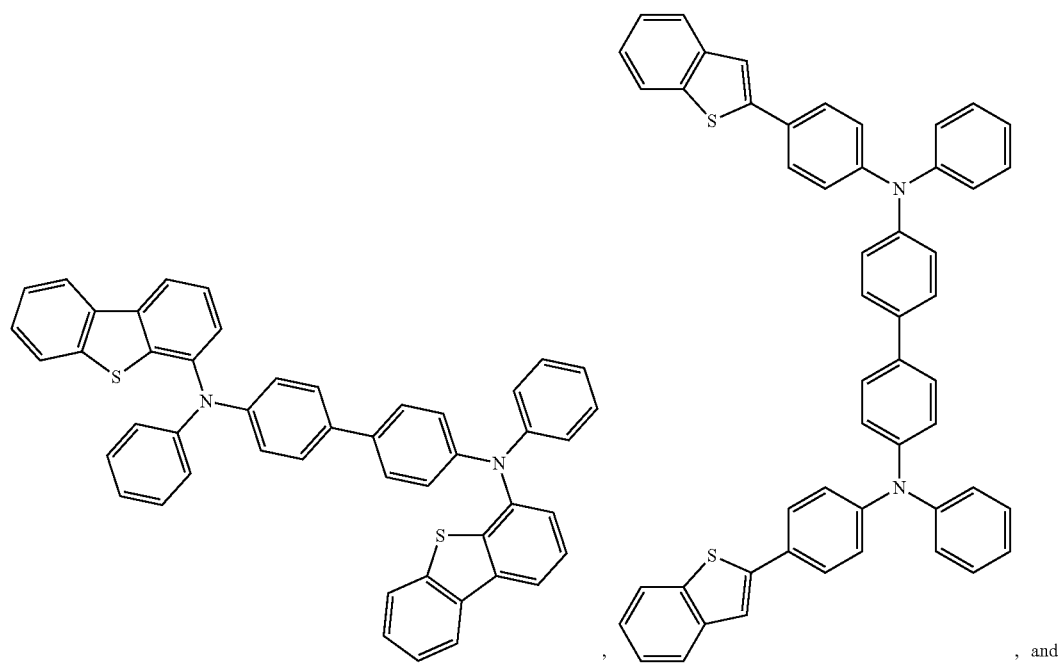
, and

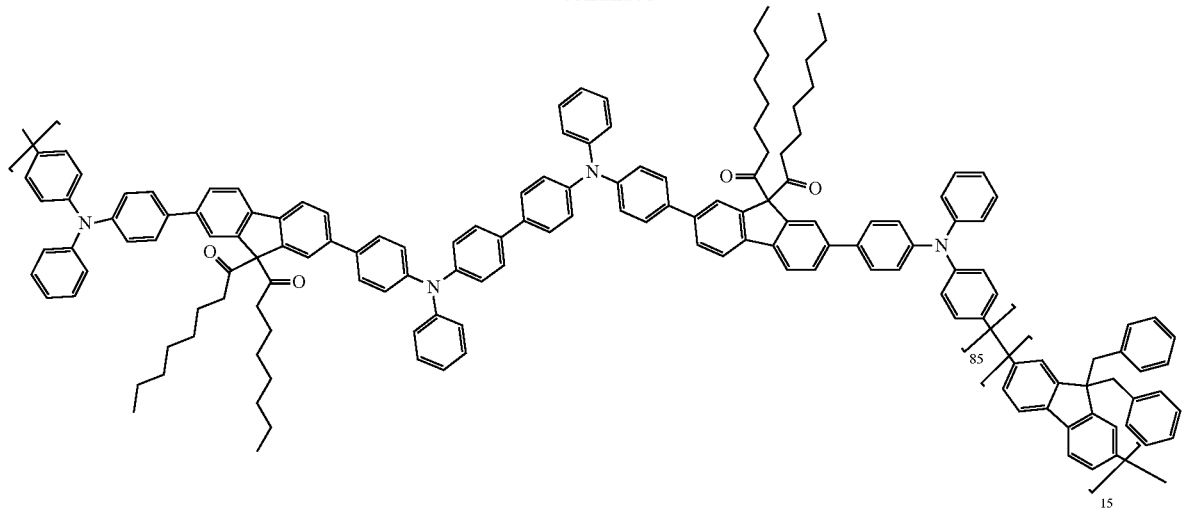

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

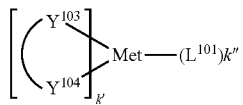

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

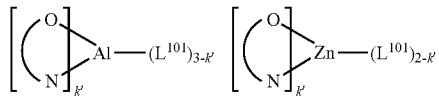

wherein (O—N) is a bidentate ligand, having metal coordinated to atoms O and N.

In another aspect, Met is selected from Ir and Pt. In a further aspect, $(Y^{103}-Y^{104})$ is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

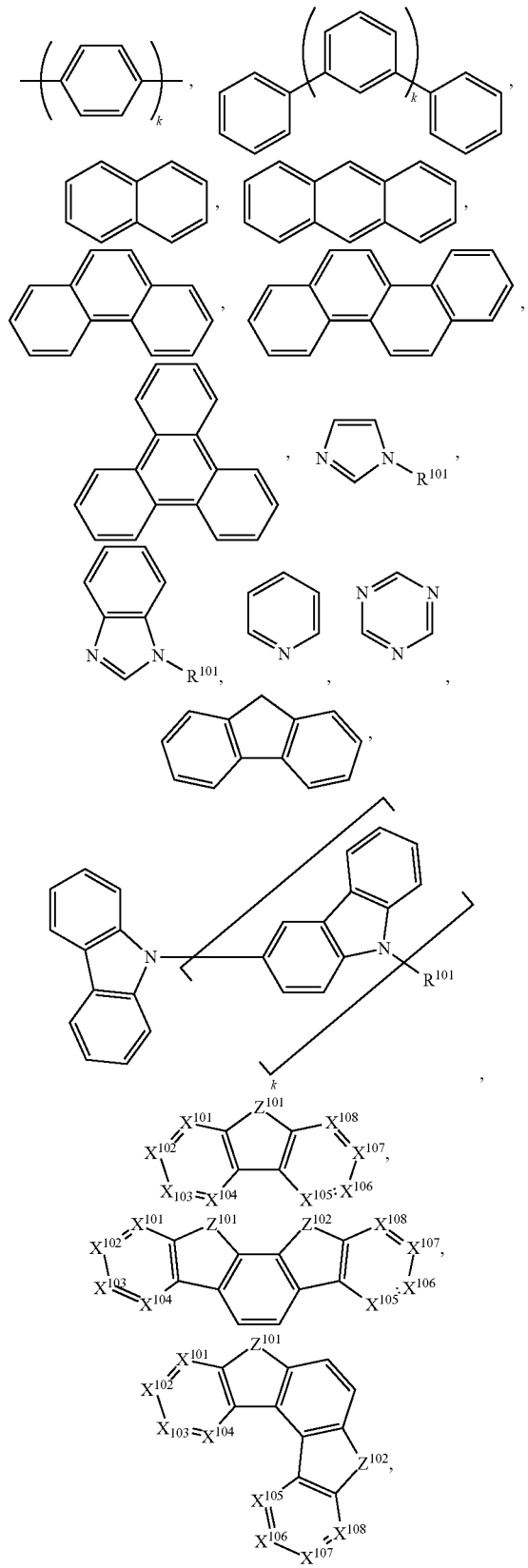

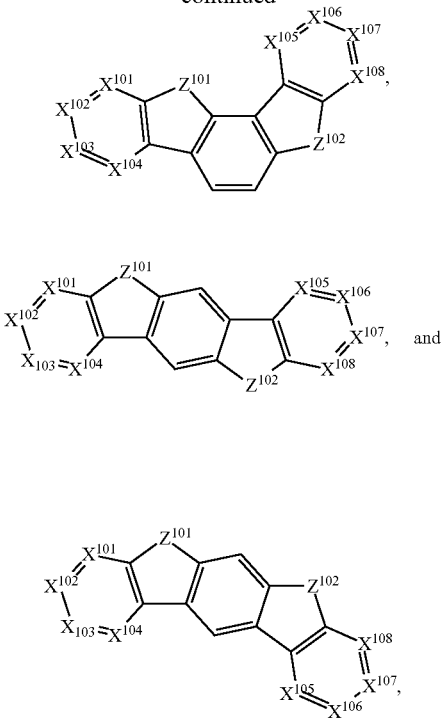

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

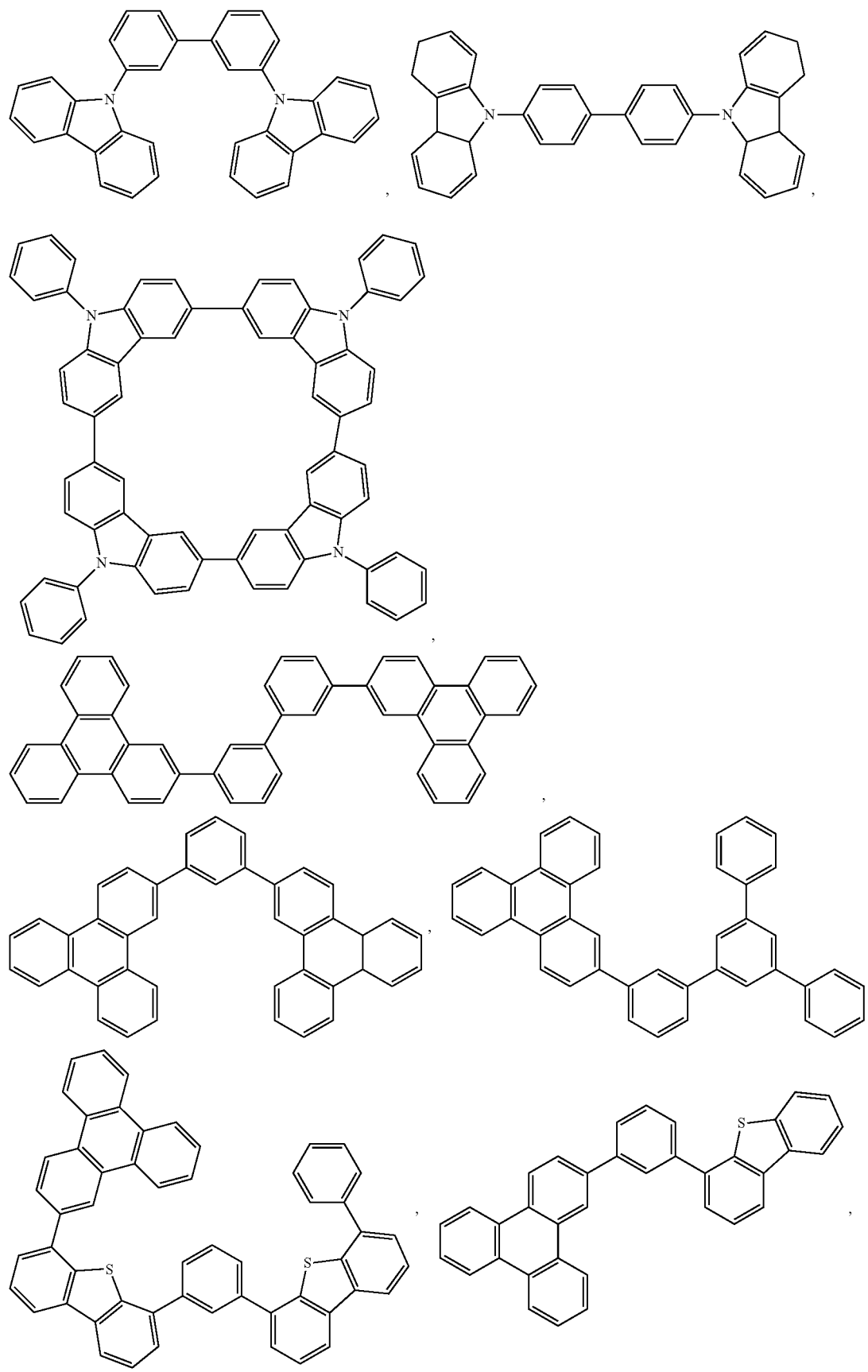

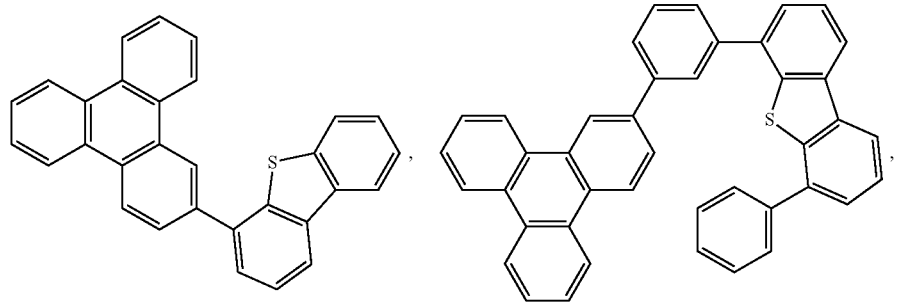
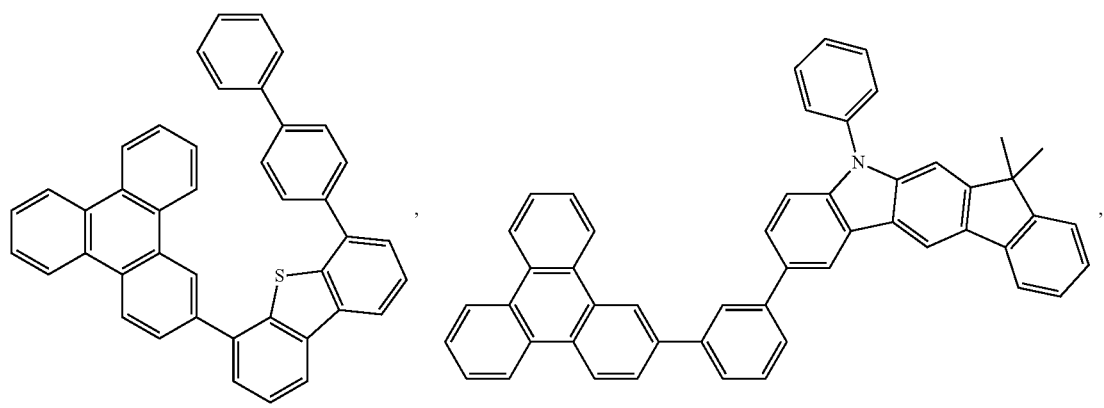
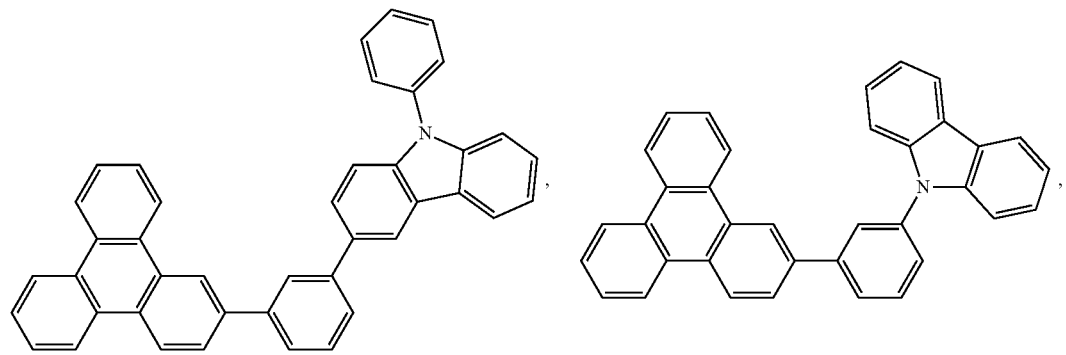
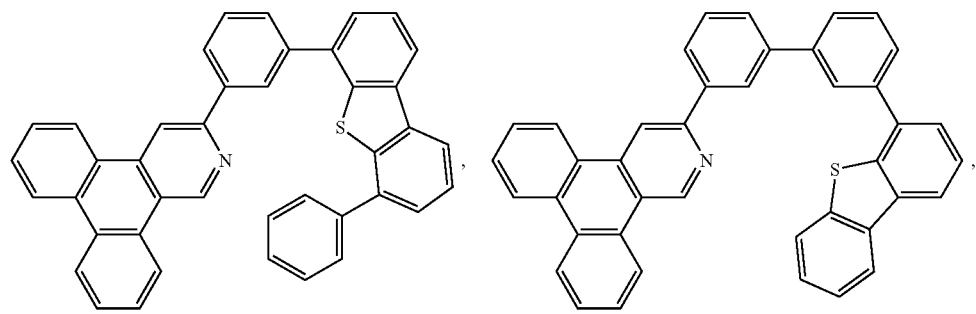
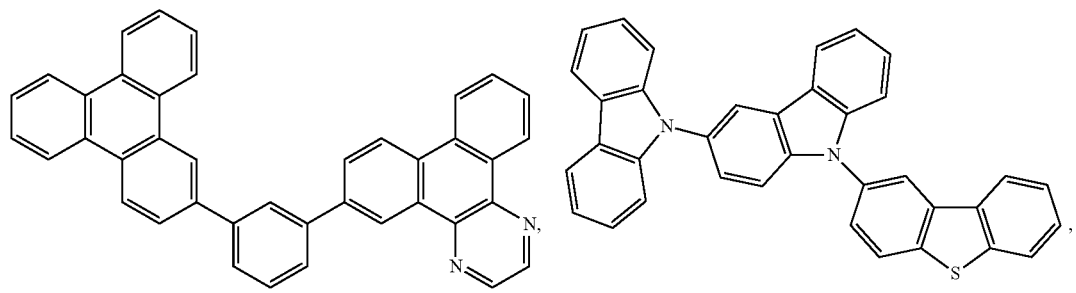

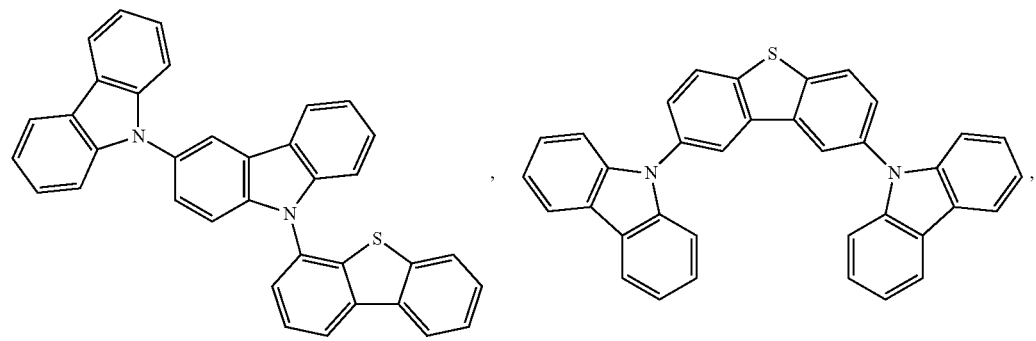
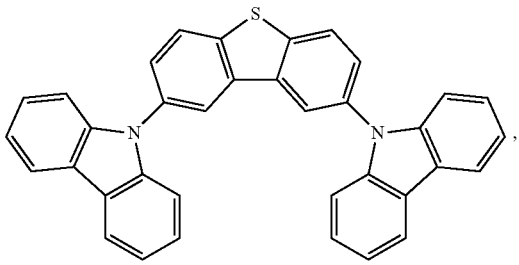
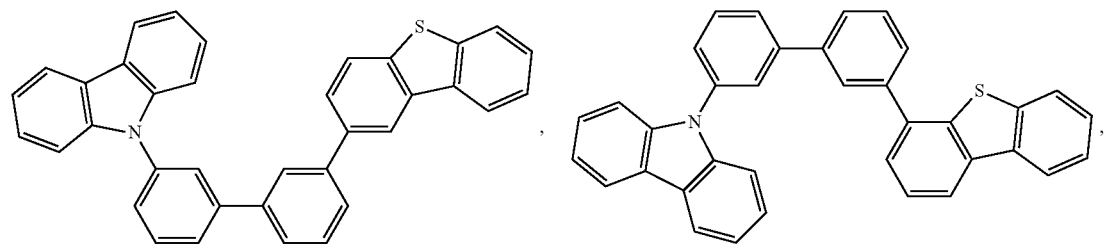
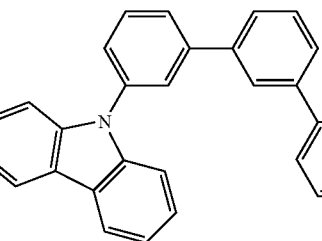
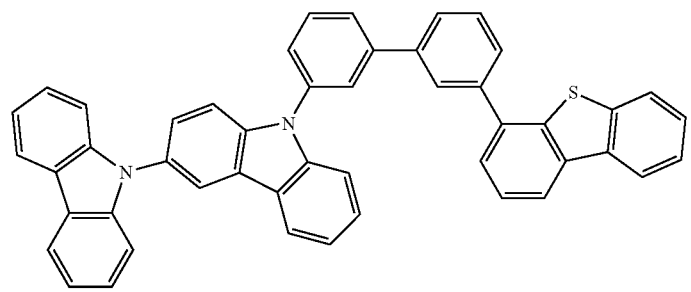
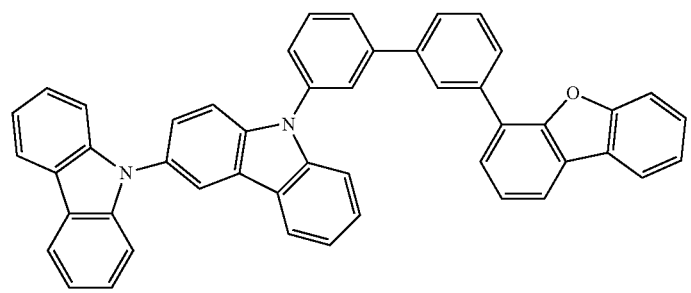
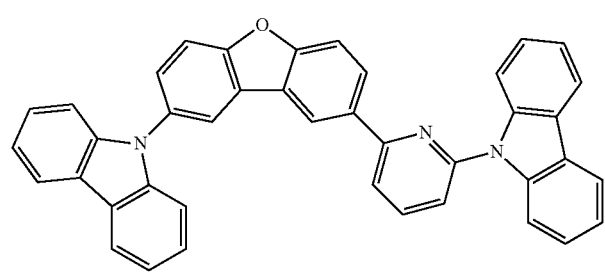
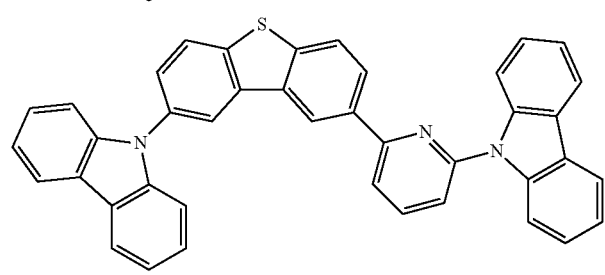

-continued
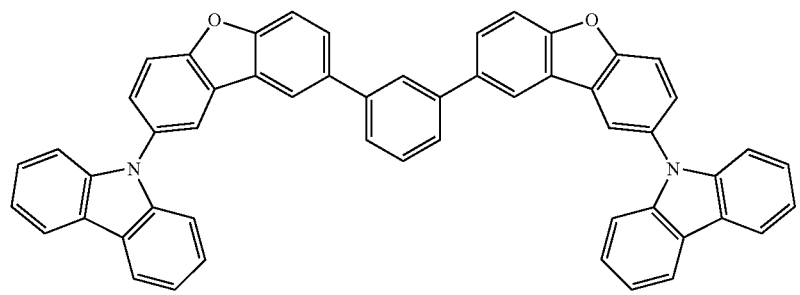
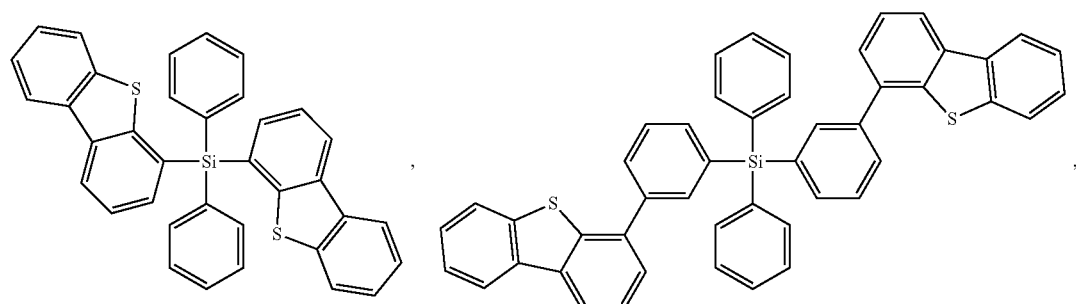
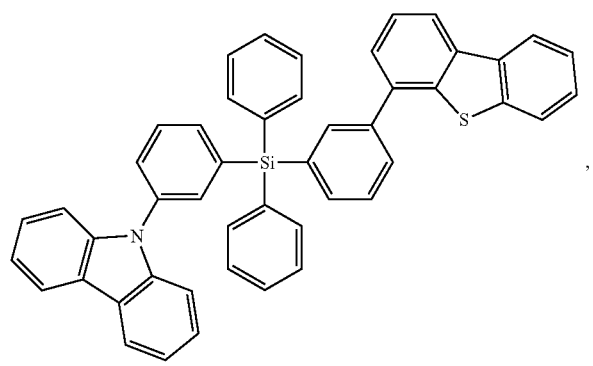
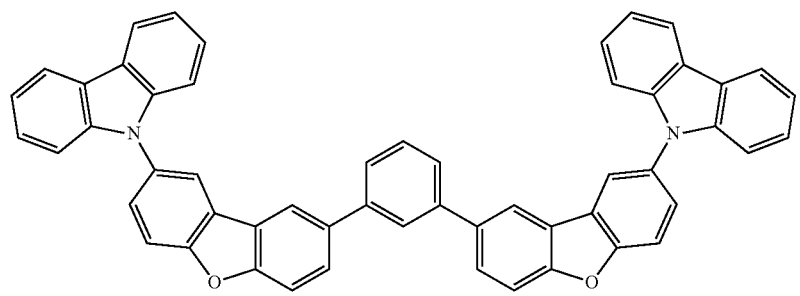
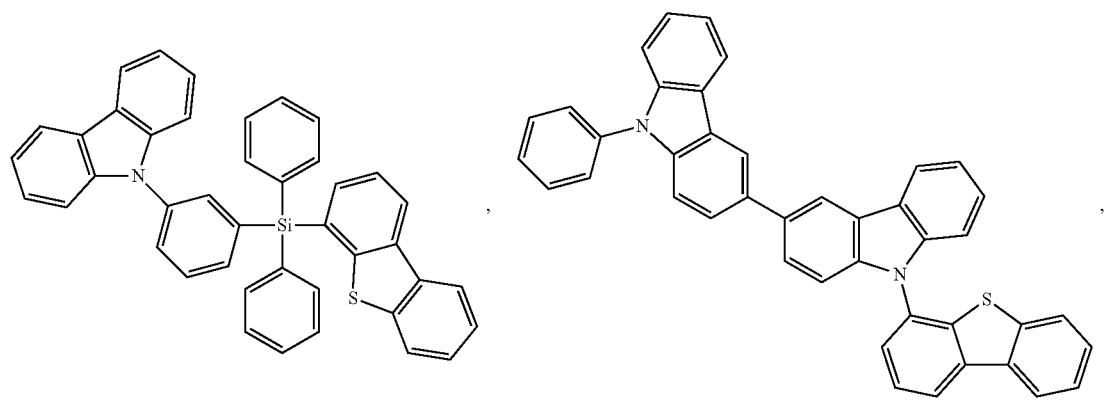

-continued
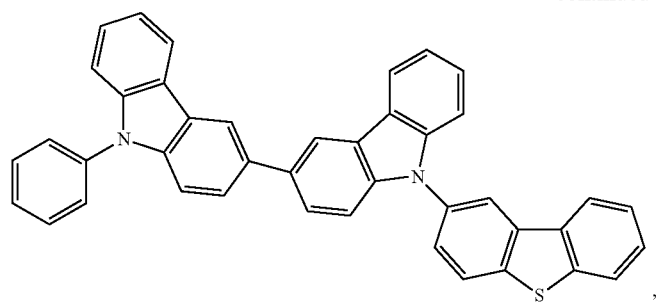
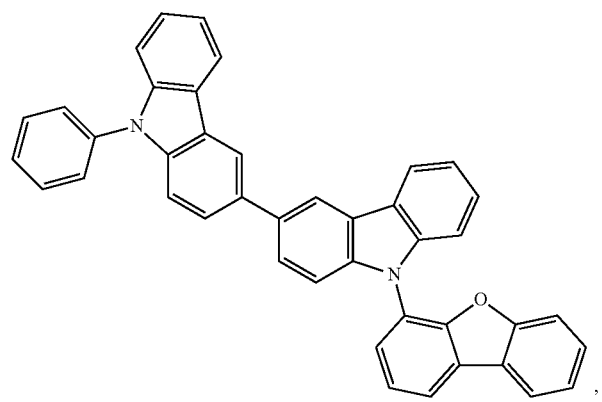
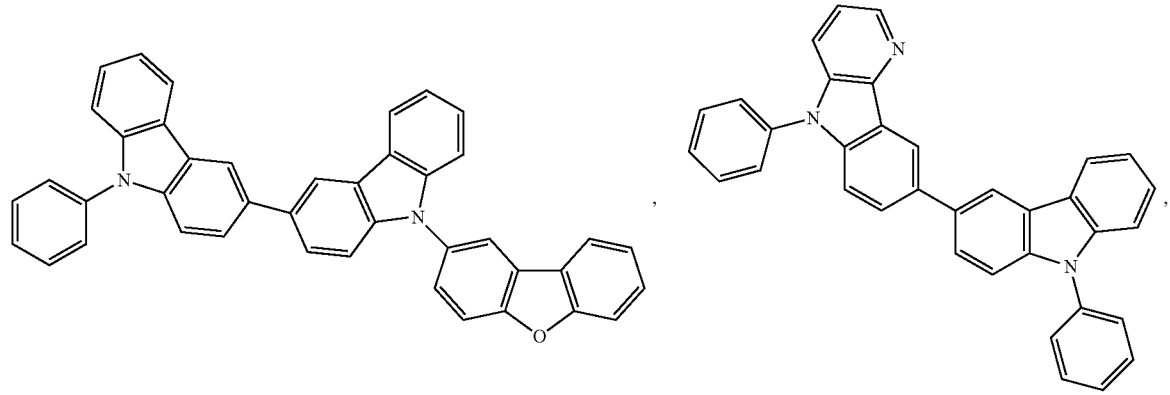
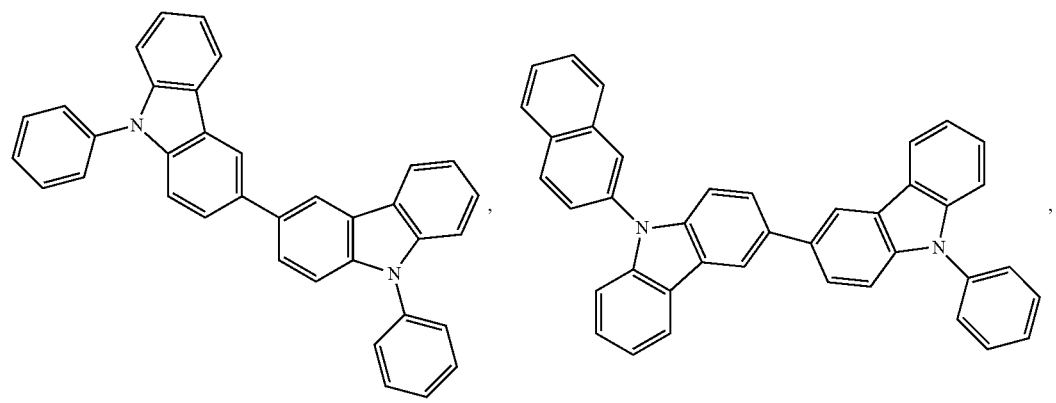

-continued
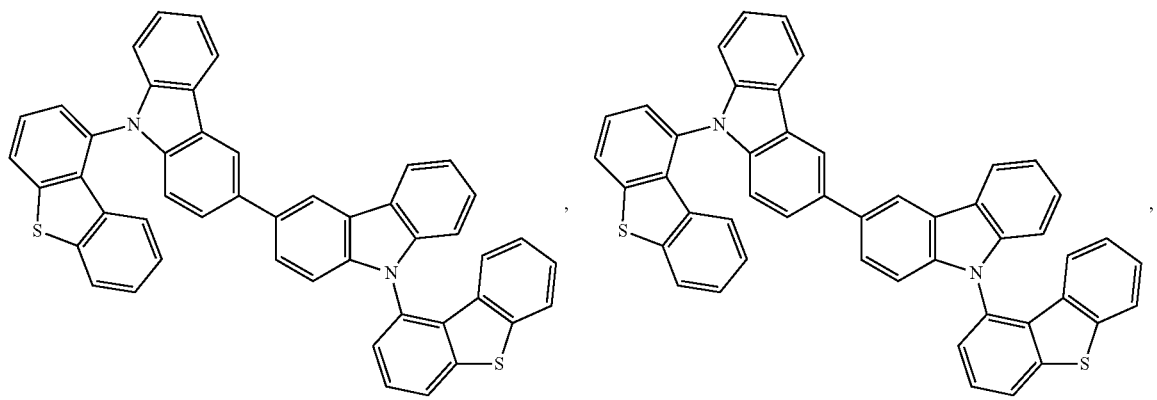
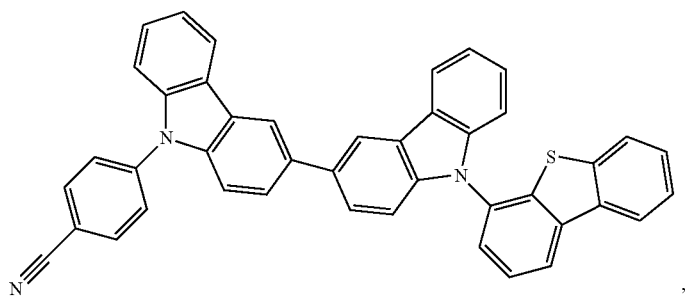
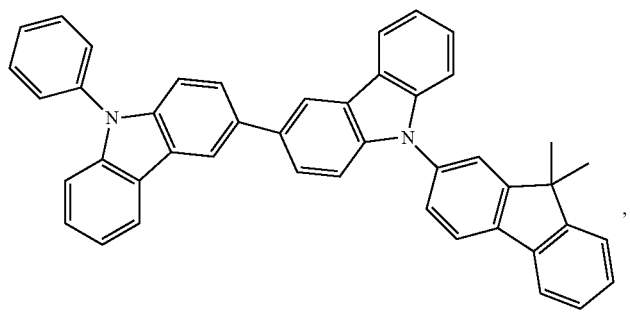
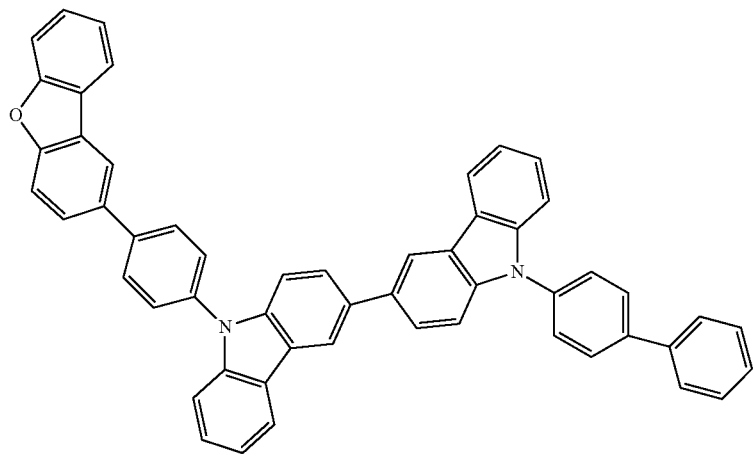

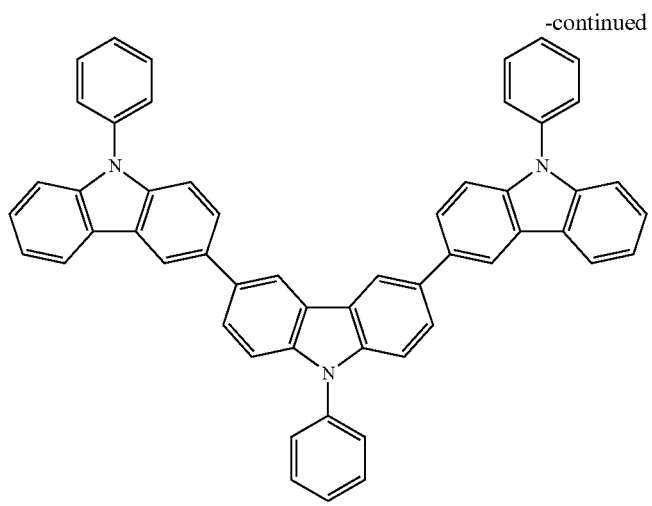
,
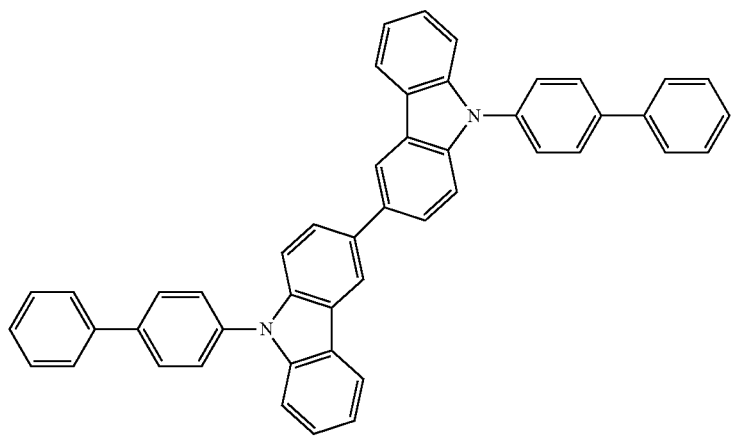
,
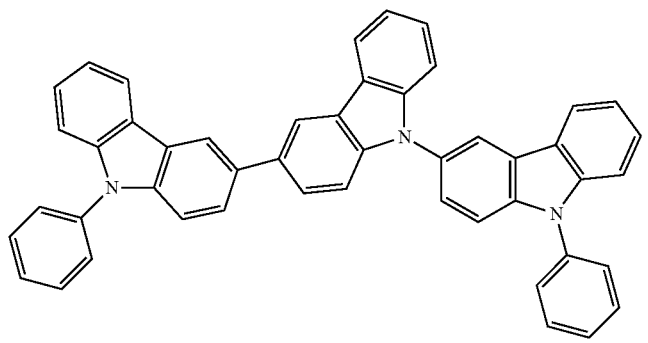
,
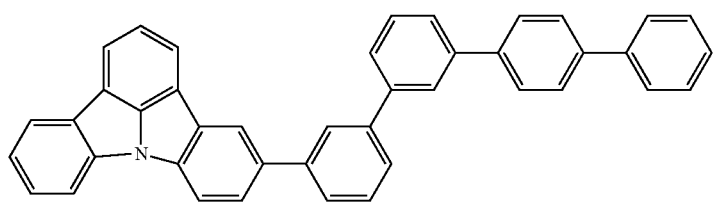
,

-continued
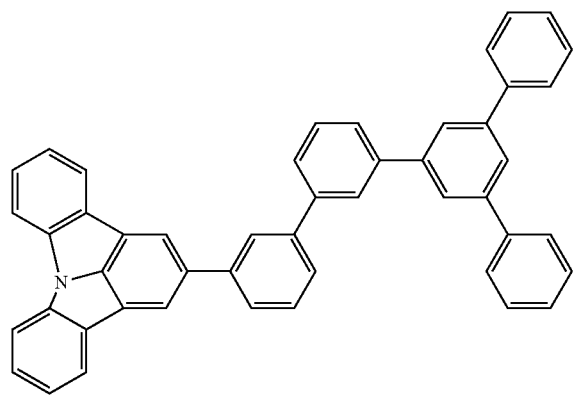
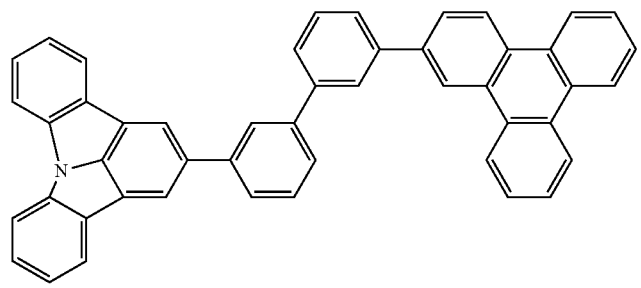
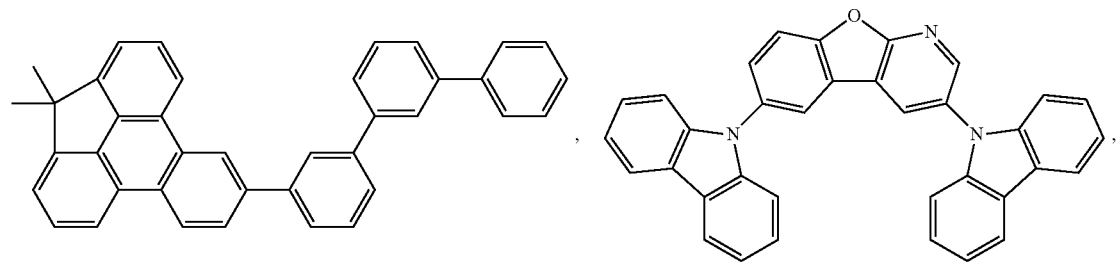
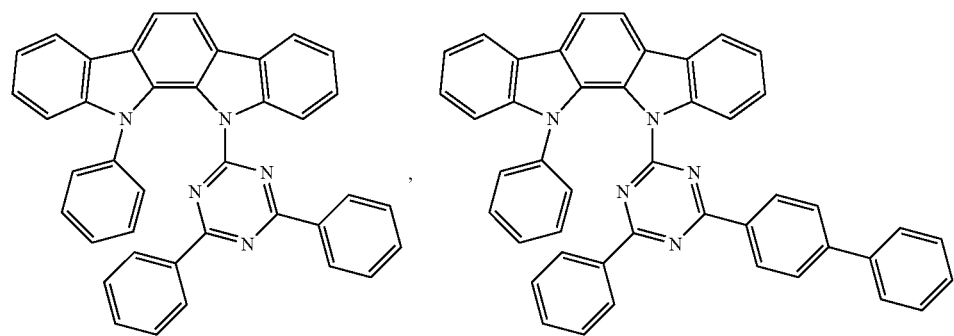
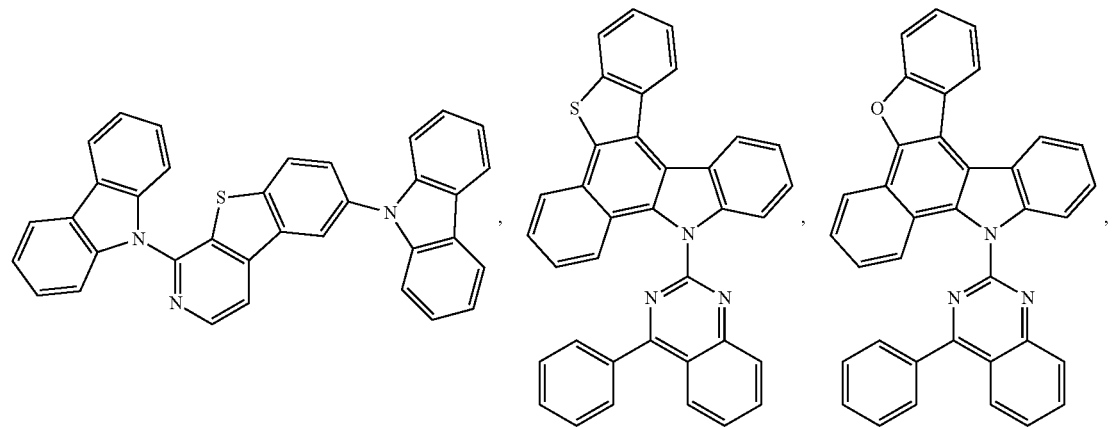

-continued
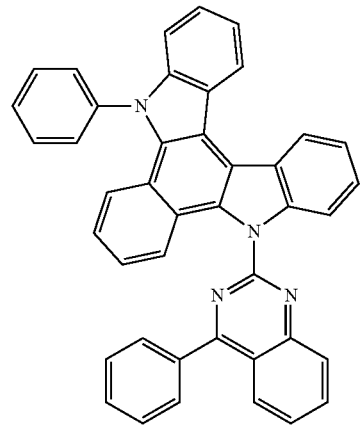
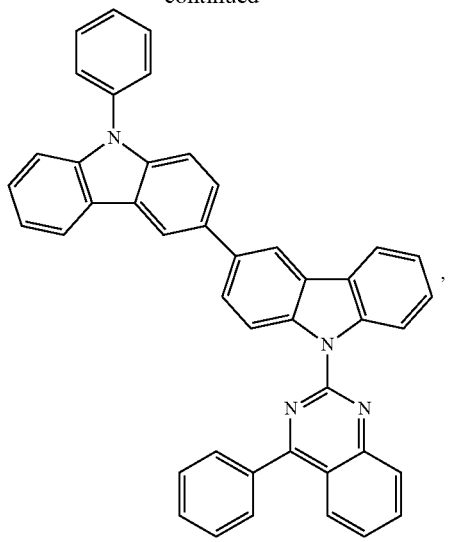
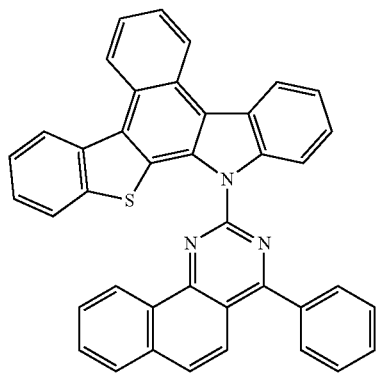
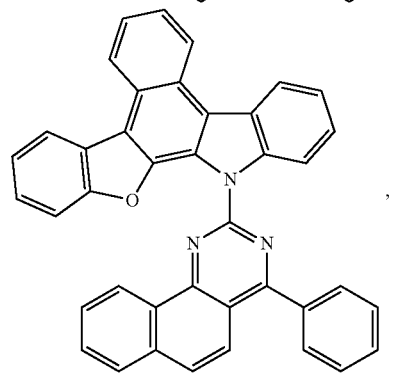
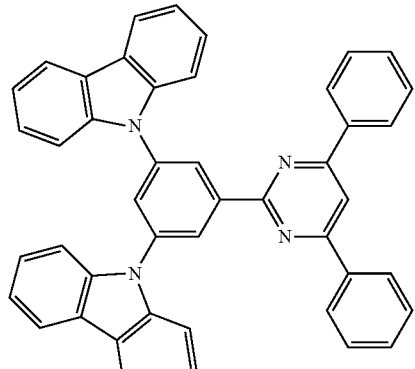
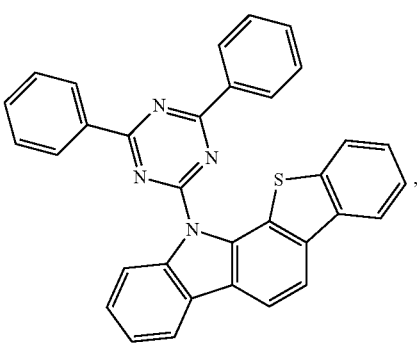
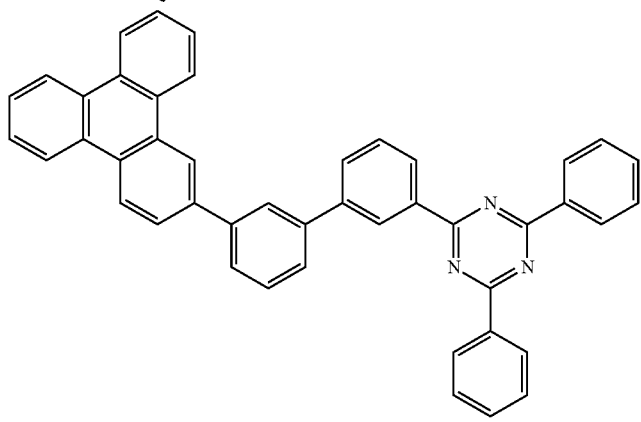

-continued
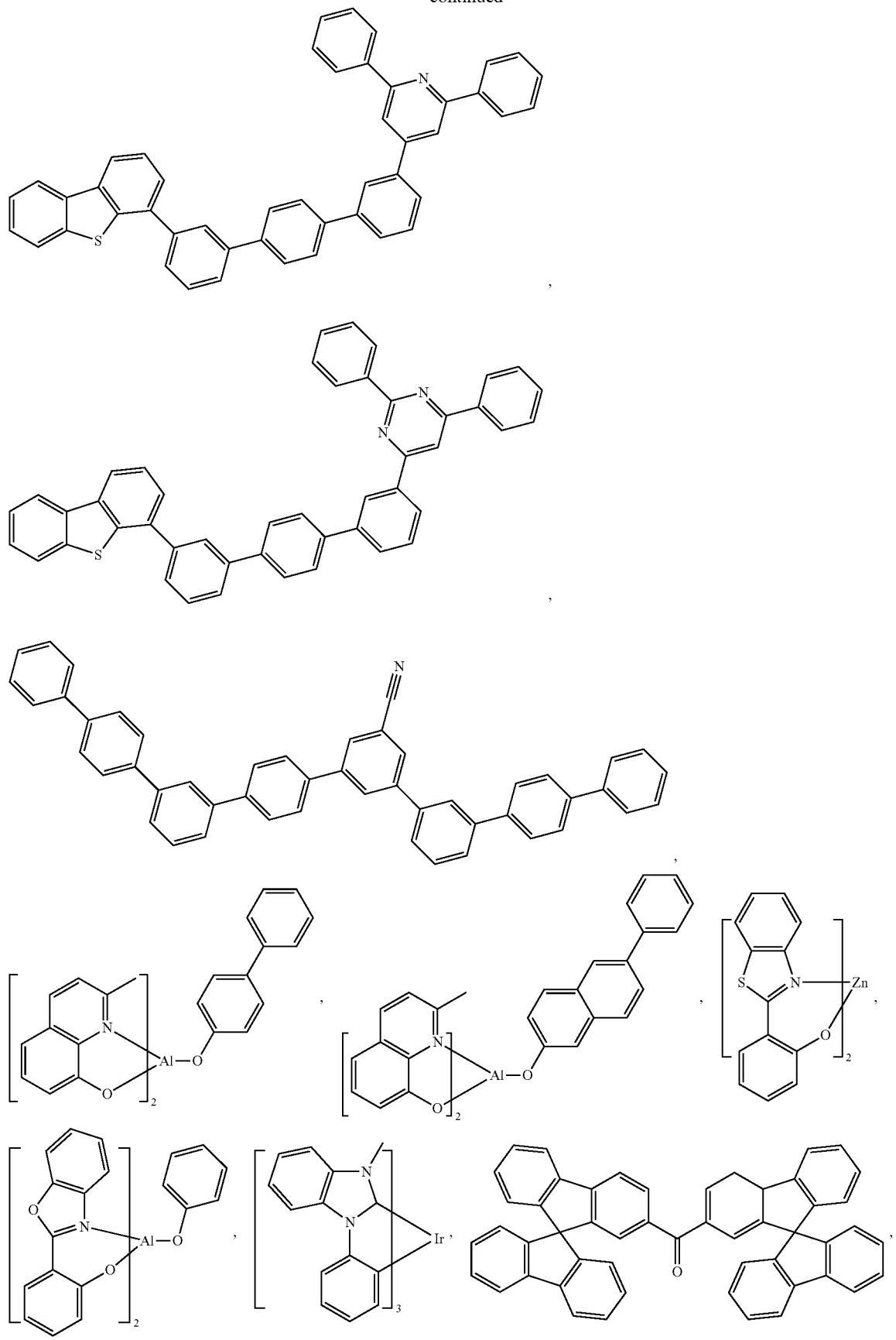

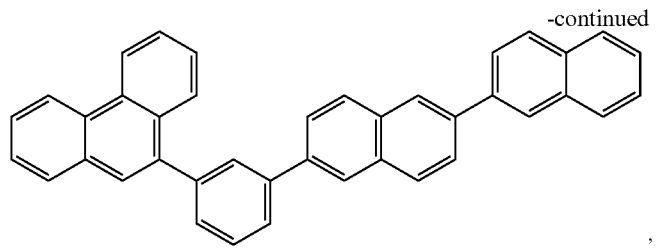

,

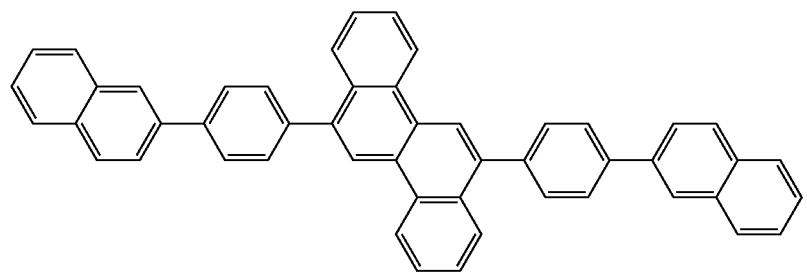

, and

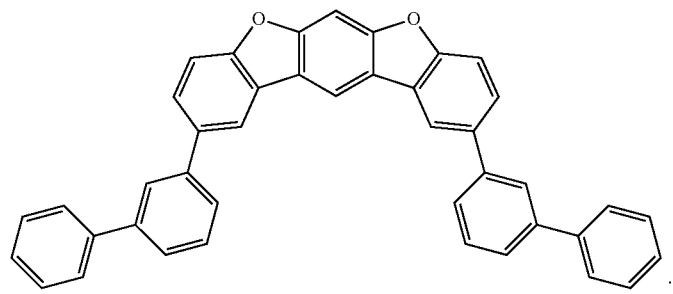

.

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

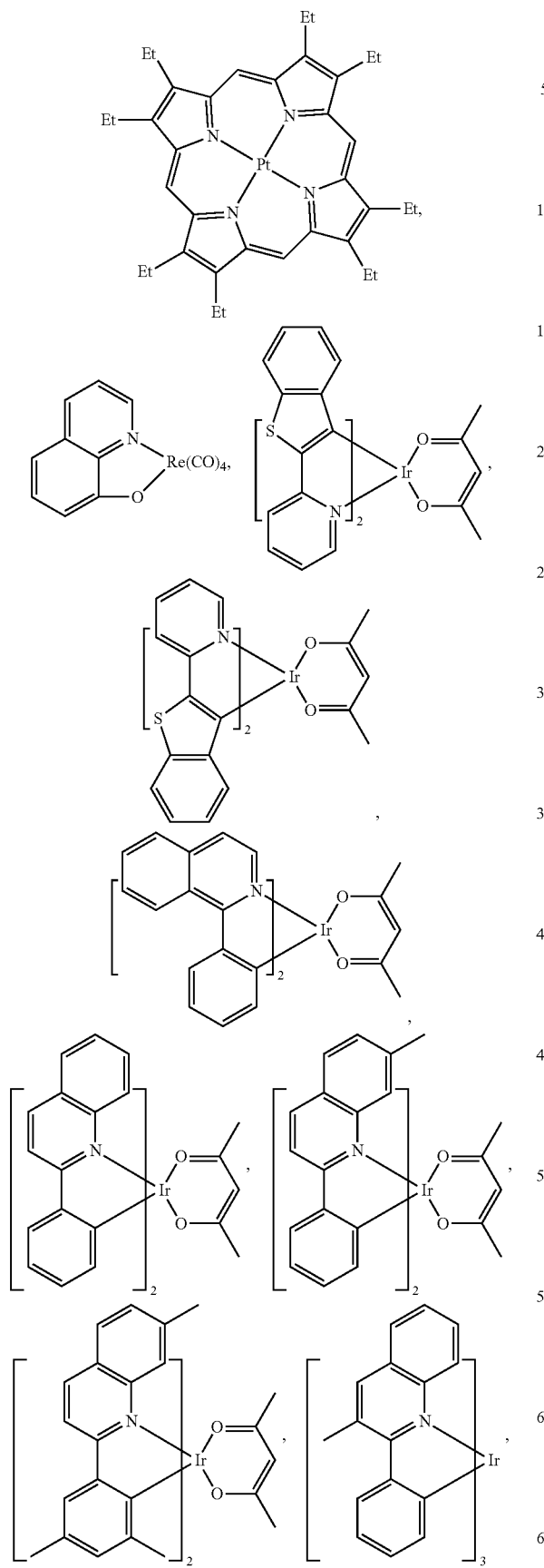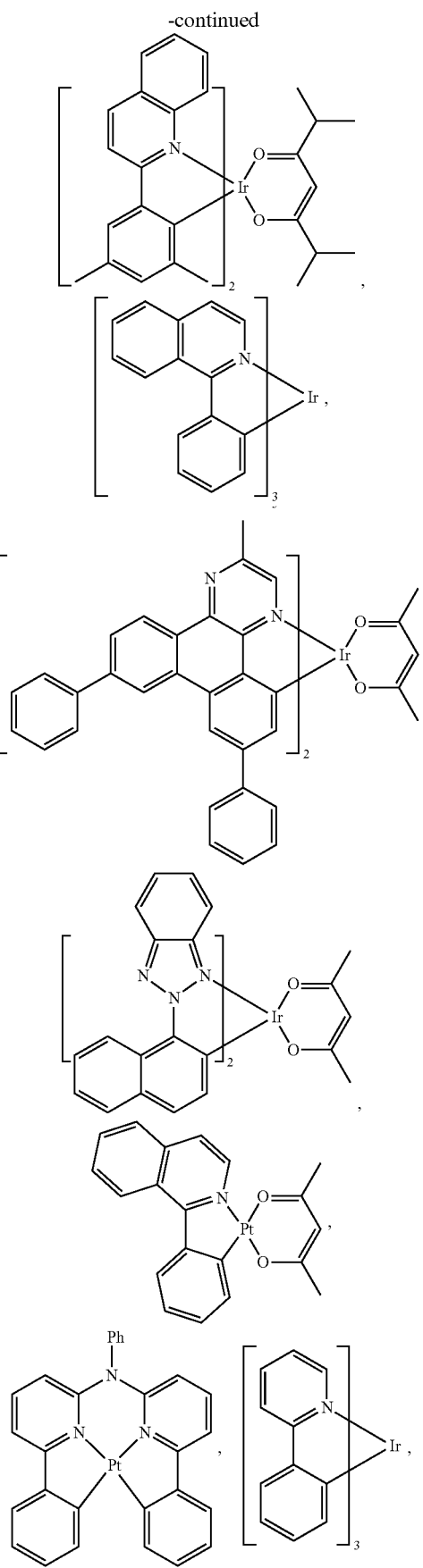

111
-continued
112
-continued
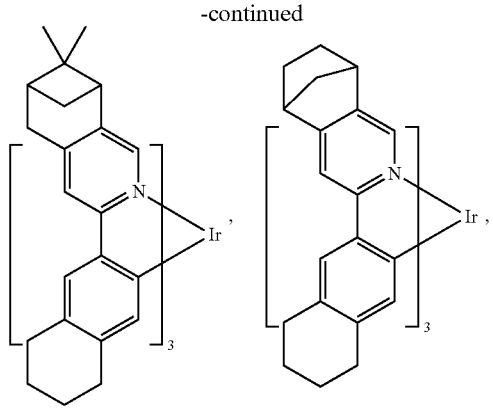
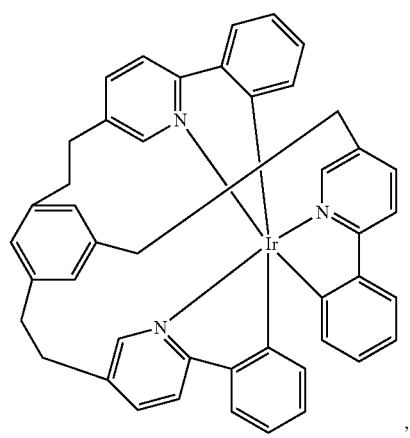
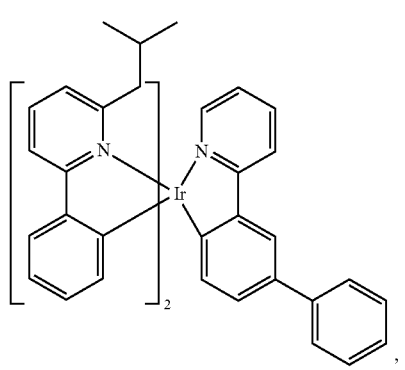
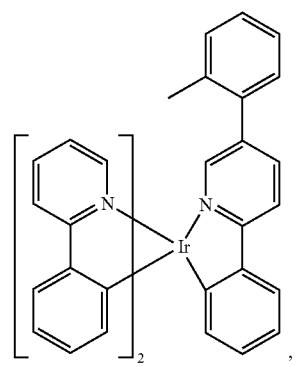
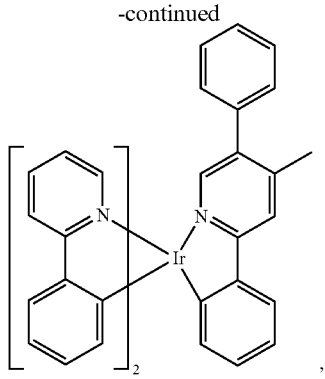
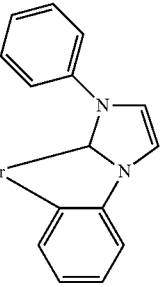
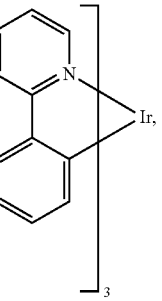
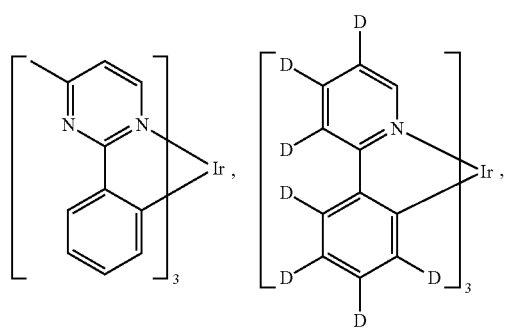
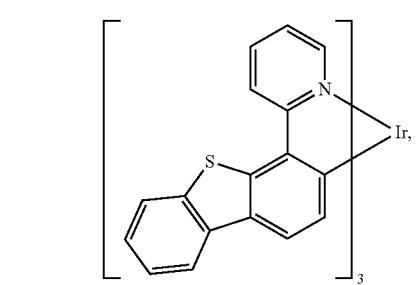

113
-continued
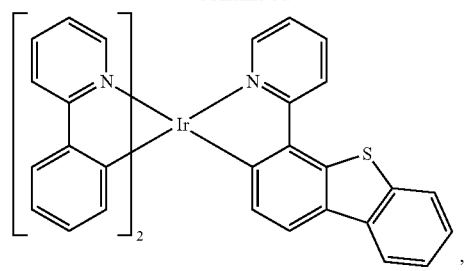
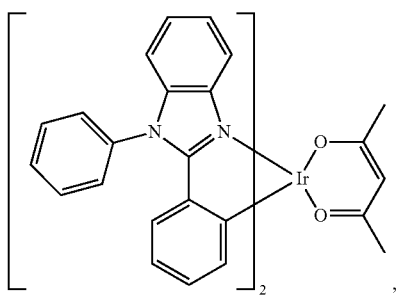
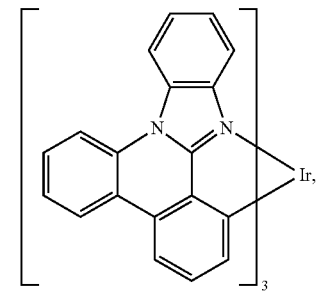
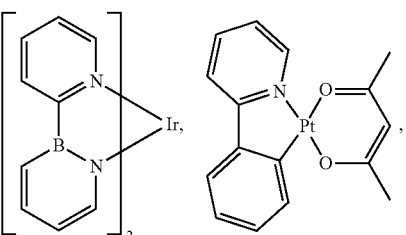
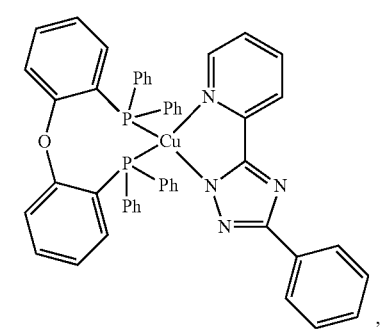
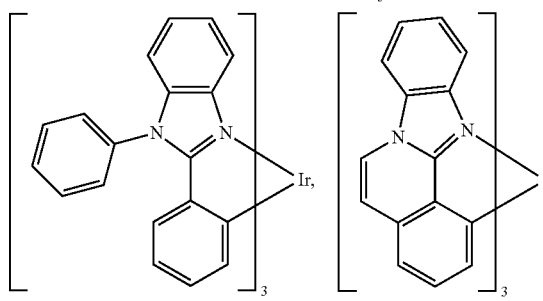
114
-continued
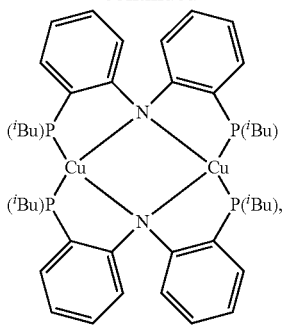
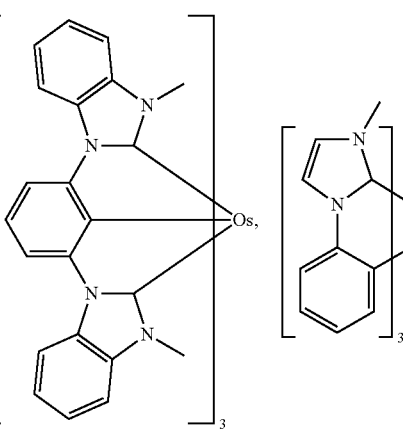
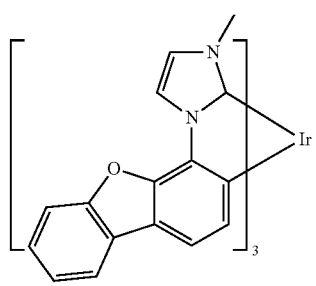
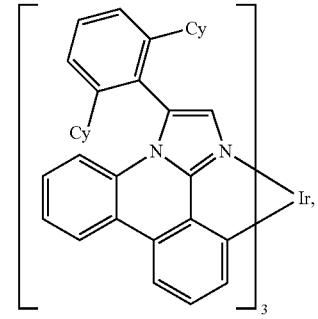
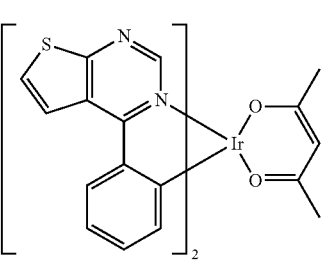

115
-continued
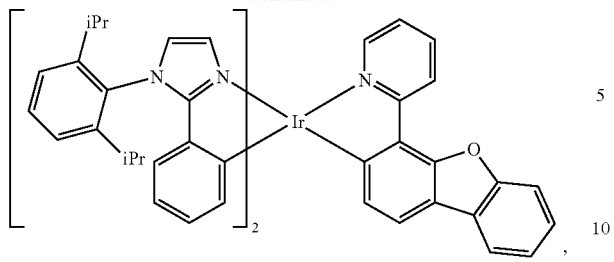
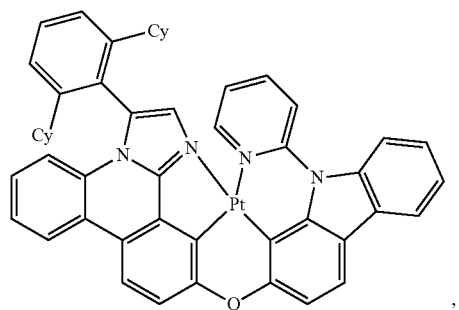
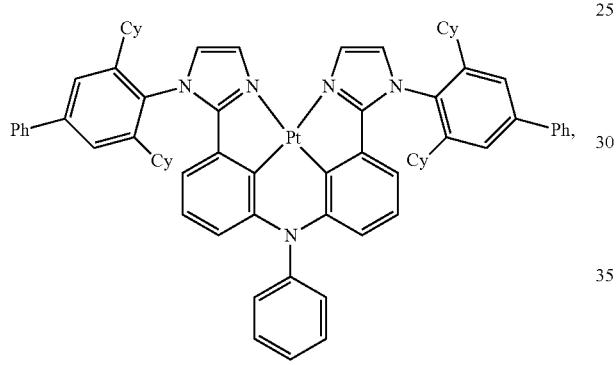
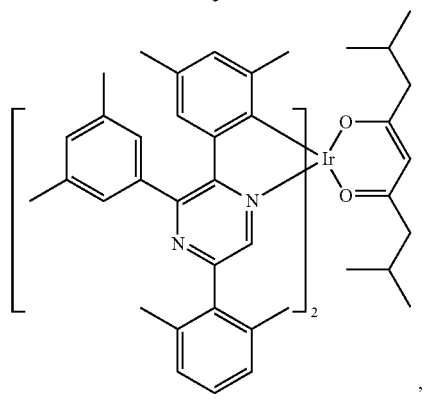
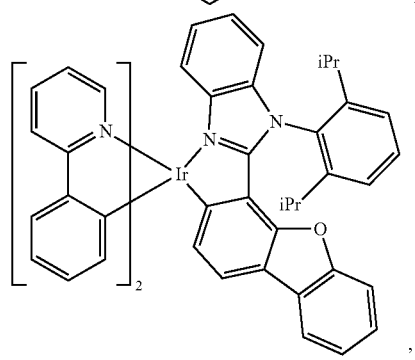
116
-continued
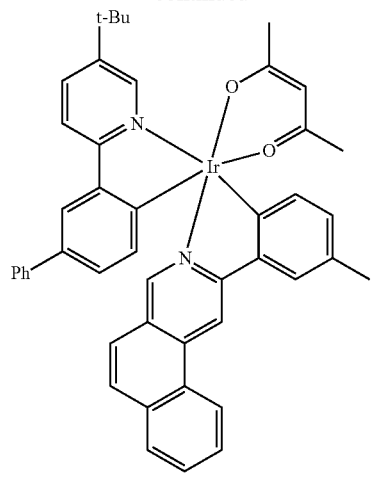
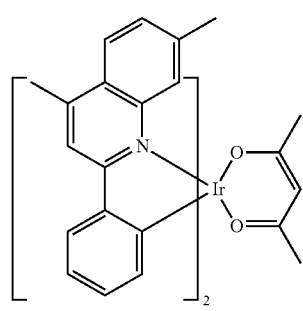
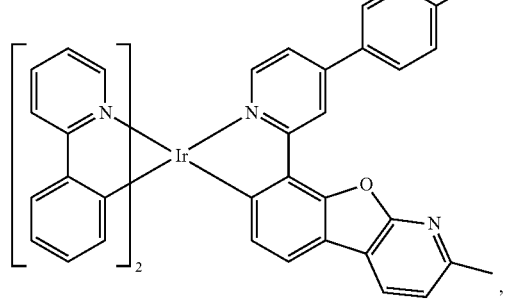
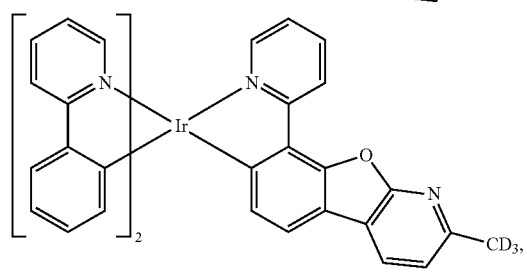
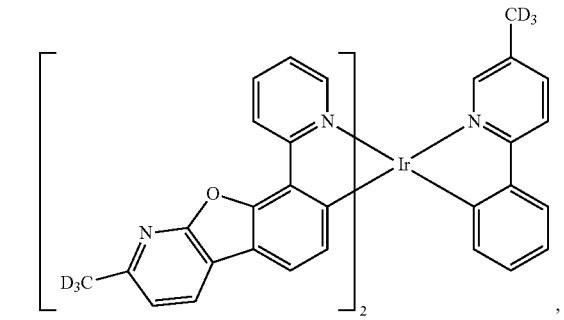

117
-continued
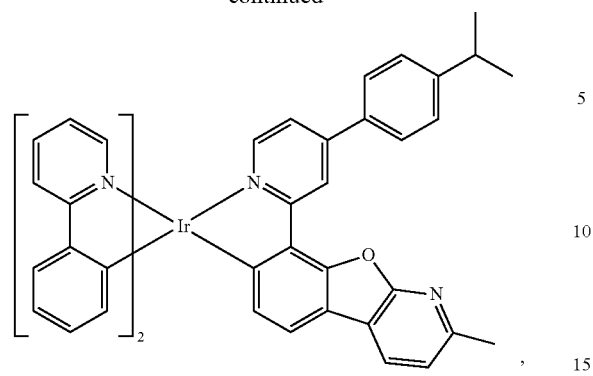
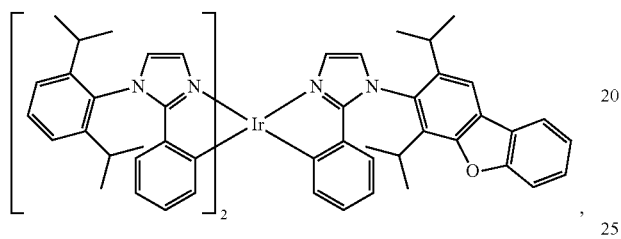
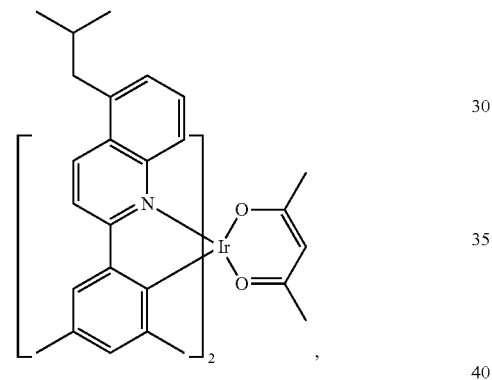
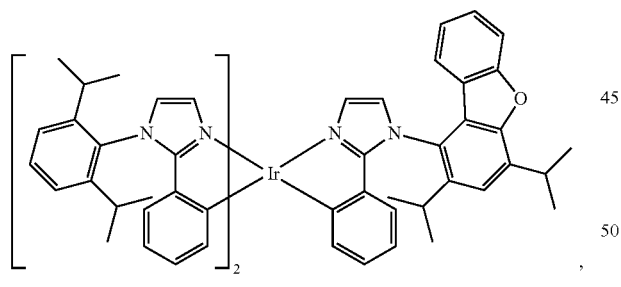
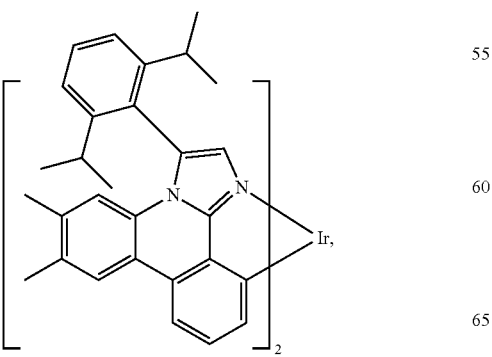
118
-continued
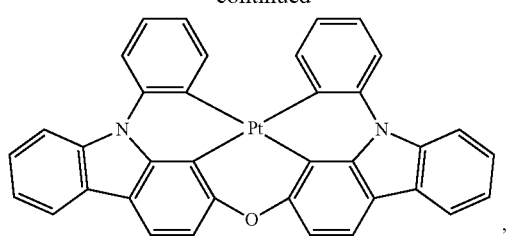
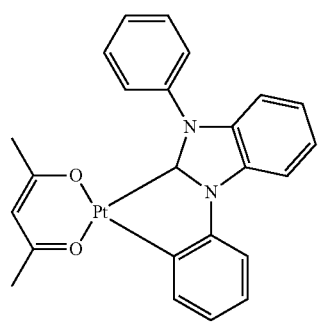
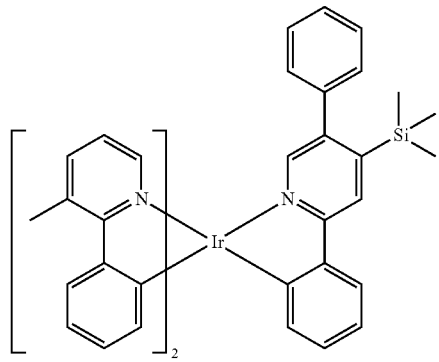
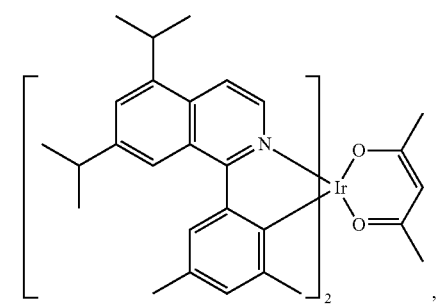
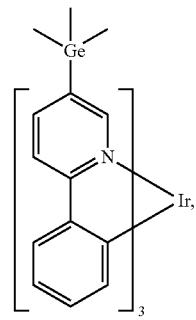

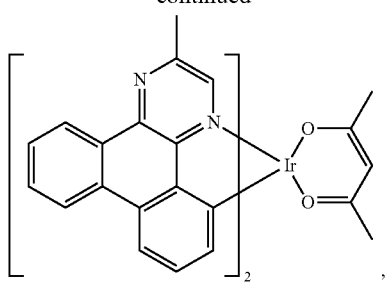
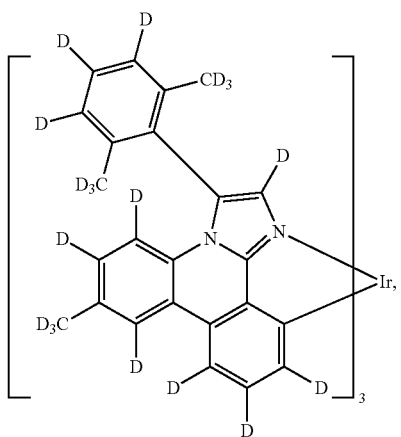
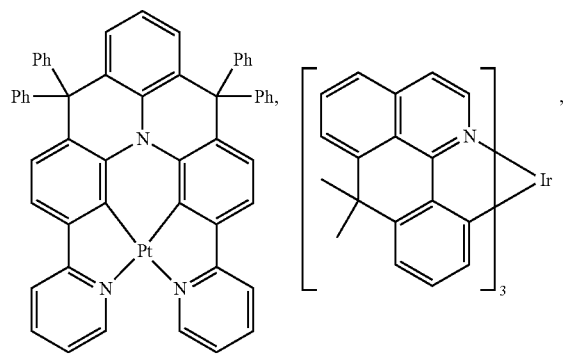
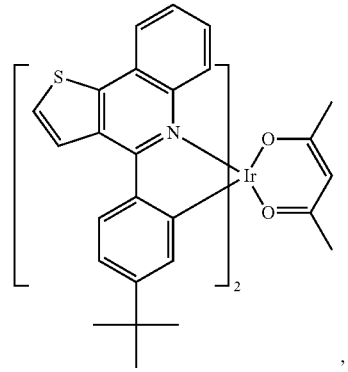
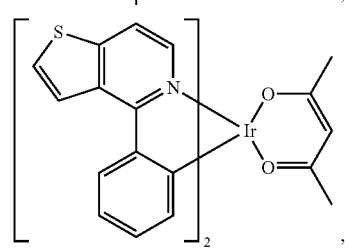
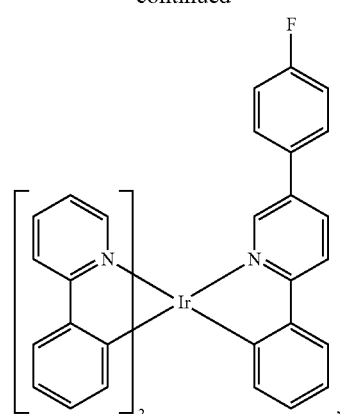
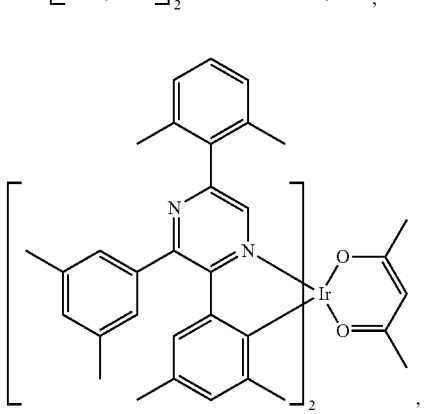
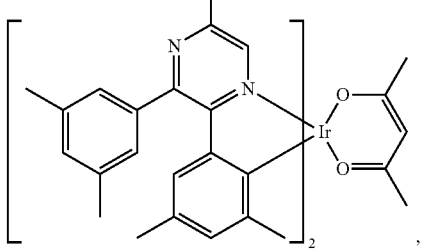
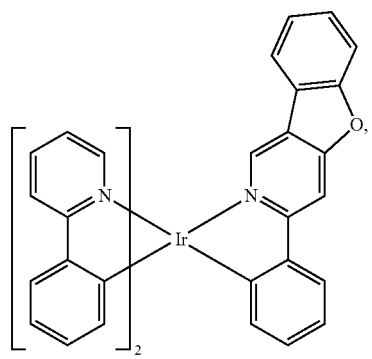
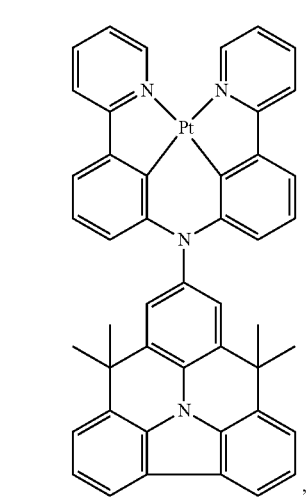

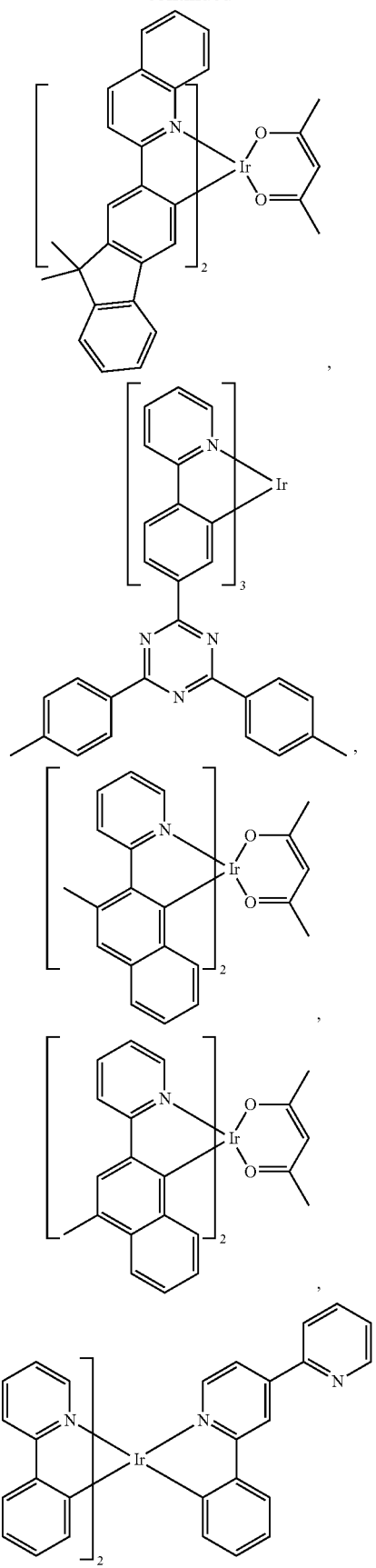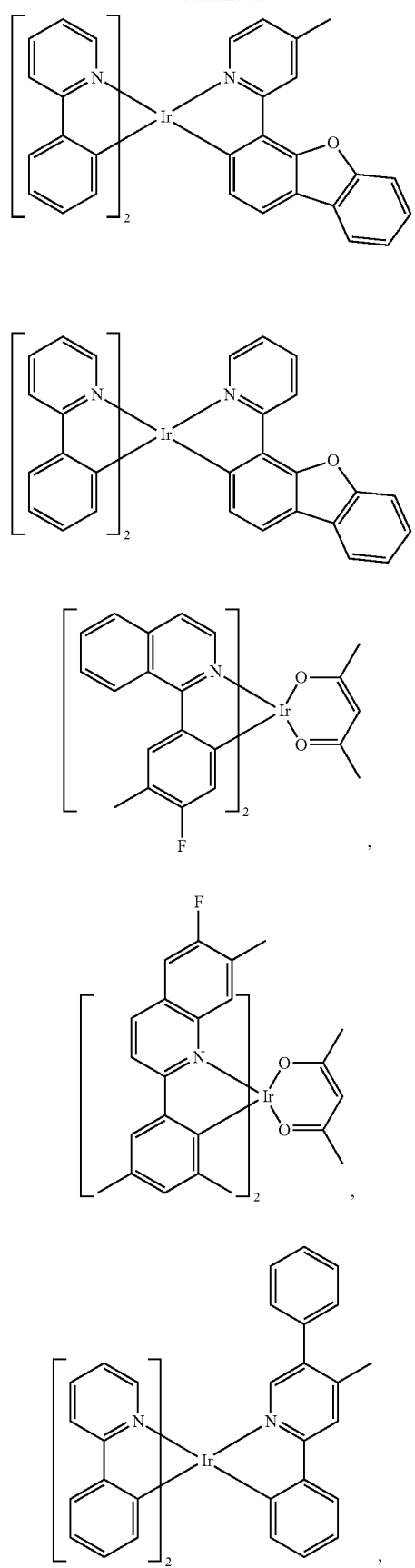

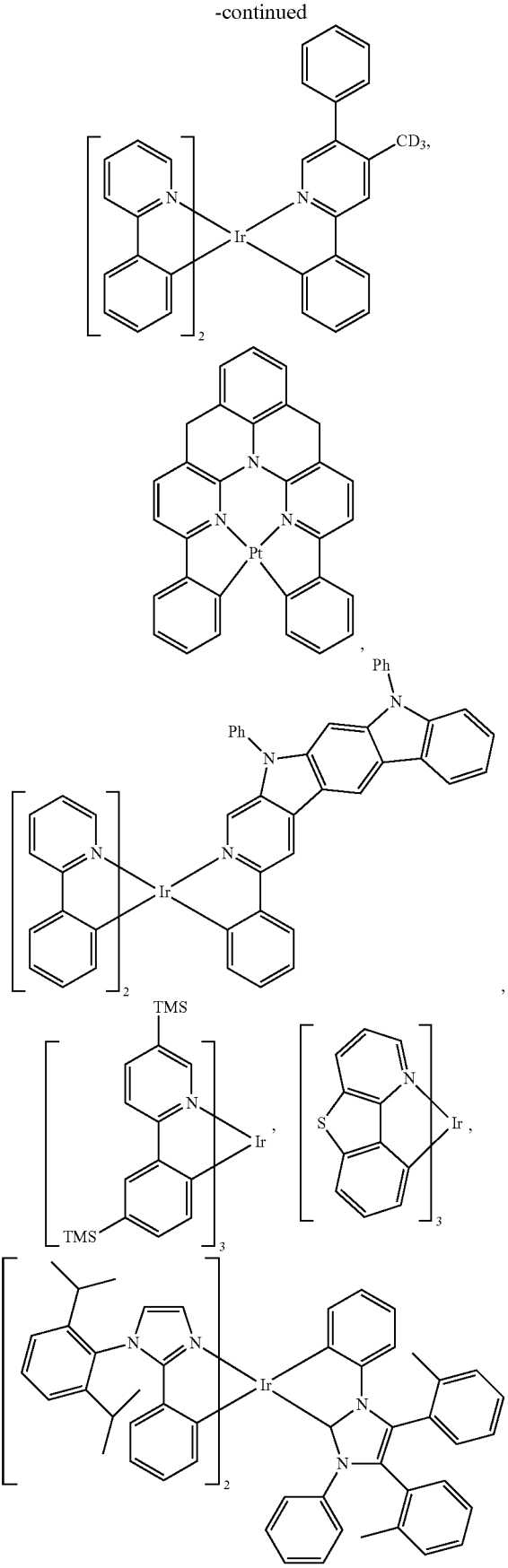
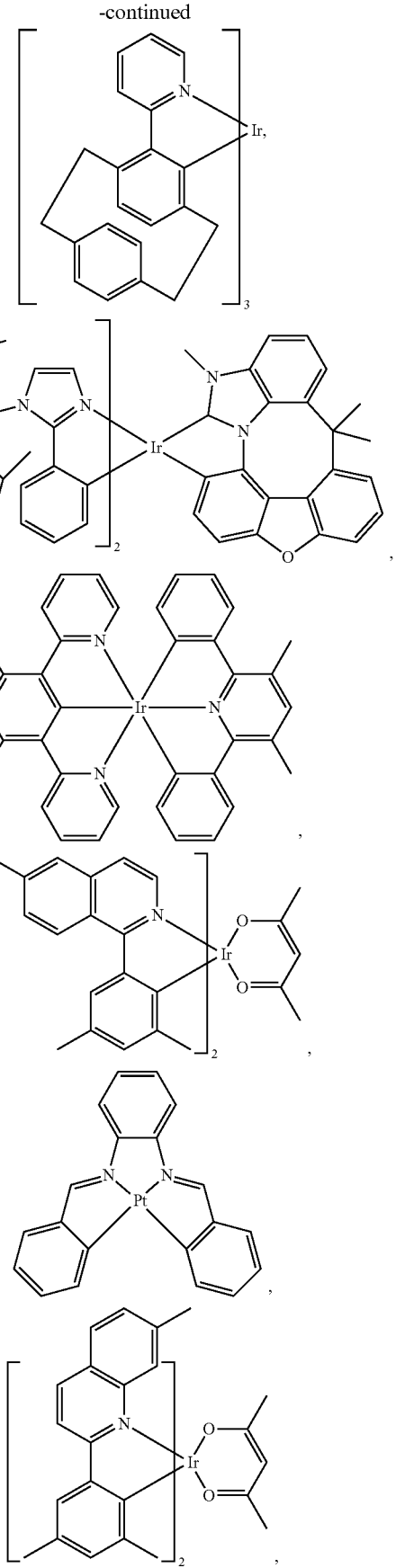

125
-continued
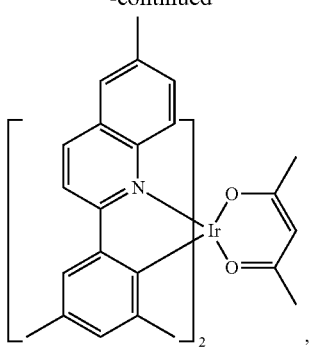
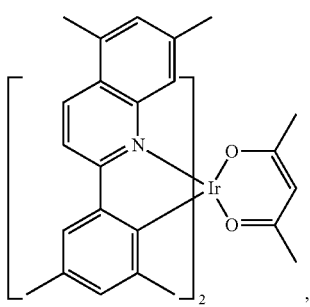
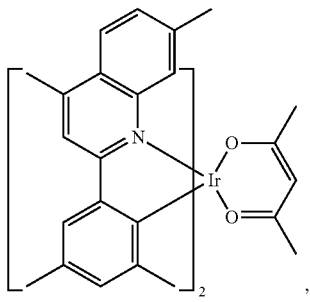
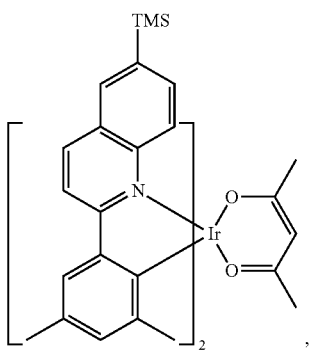
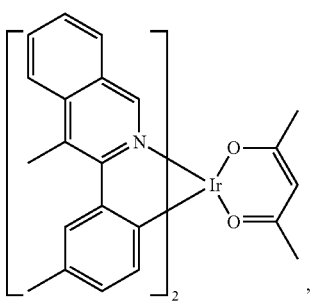
126
-continued
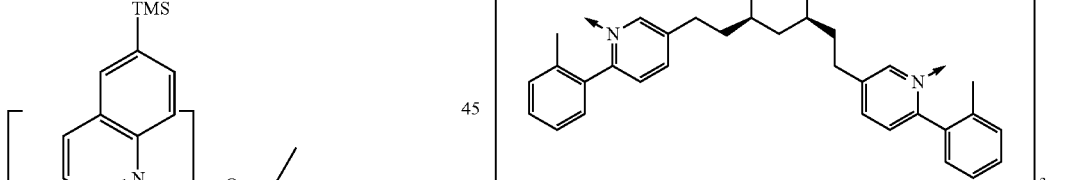
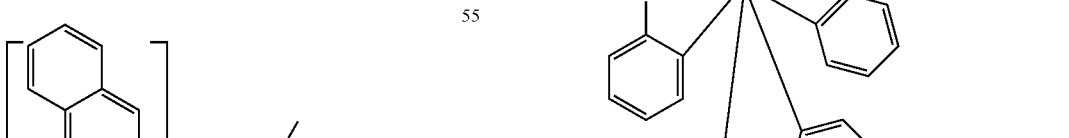
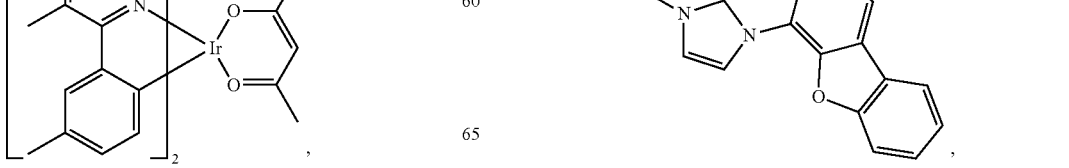

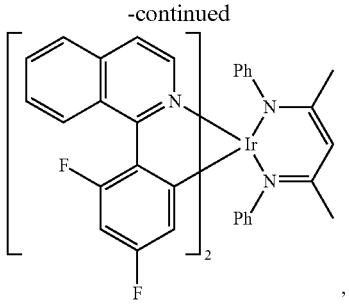
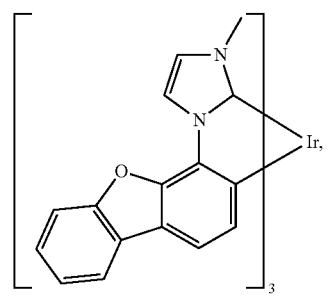
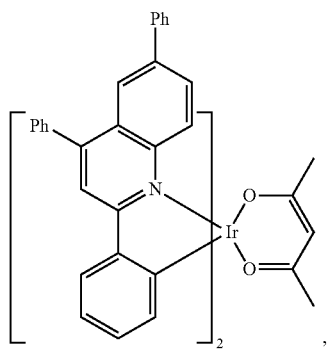
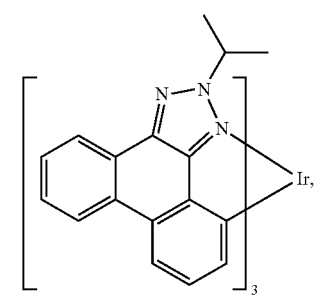
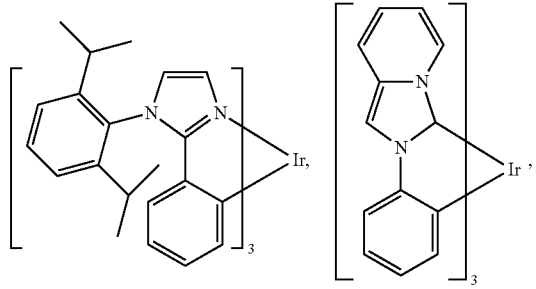
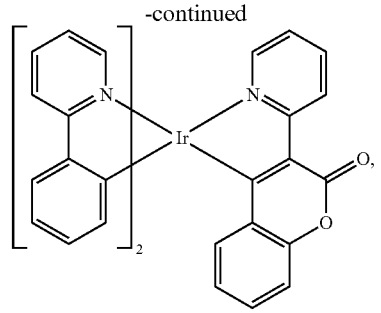
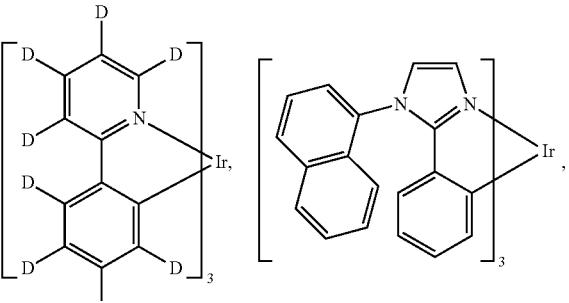
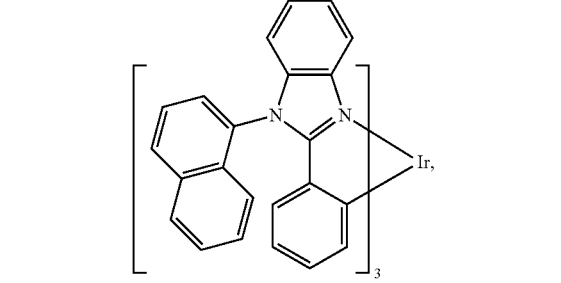
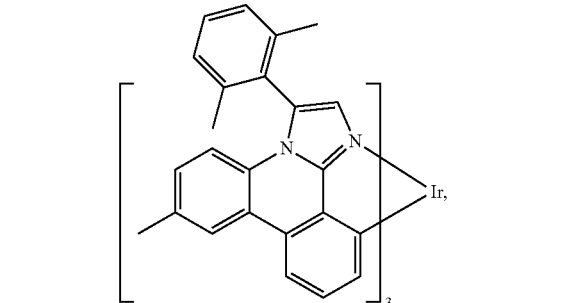
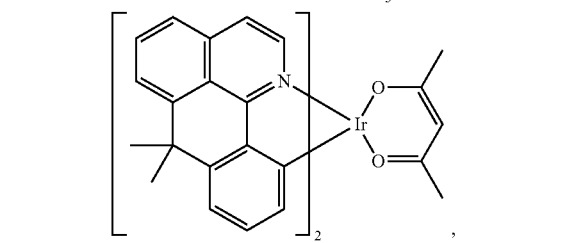
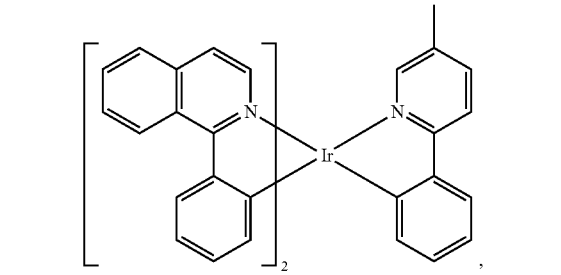

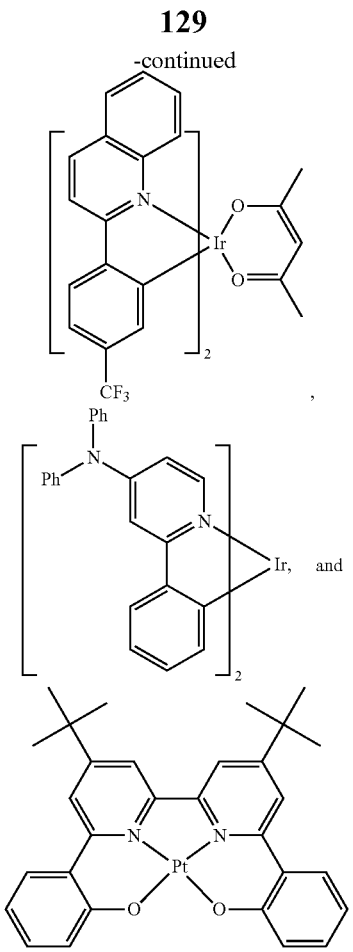

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

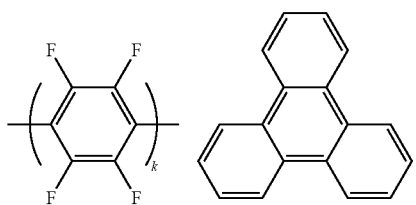

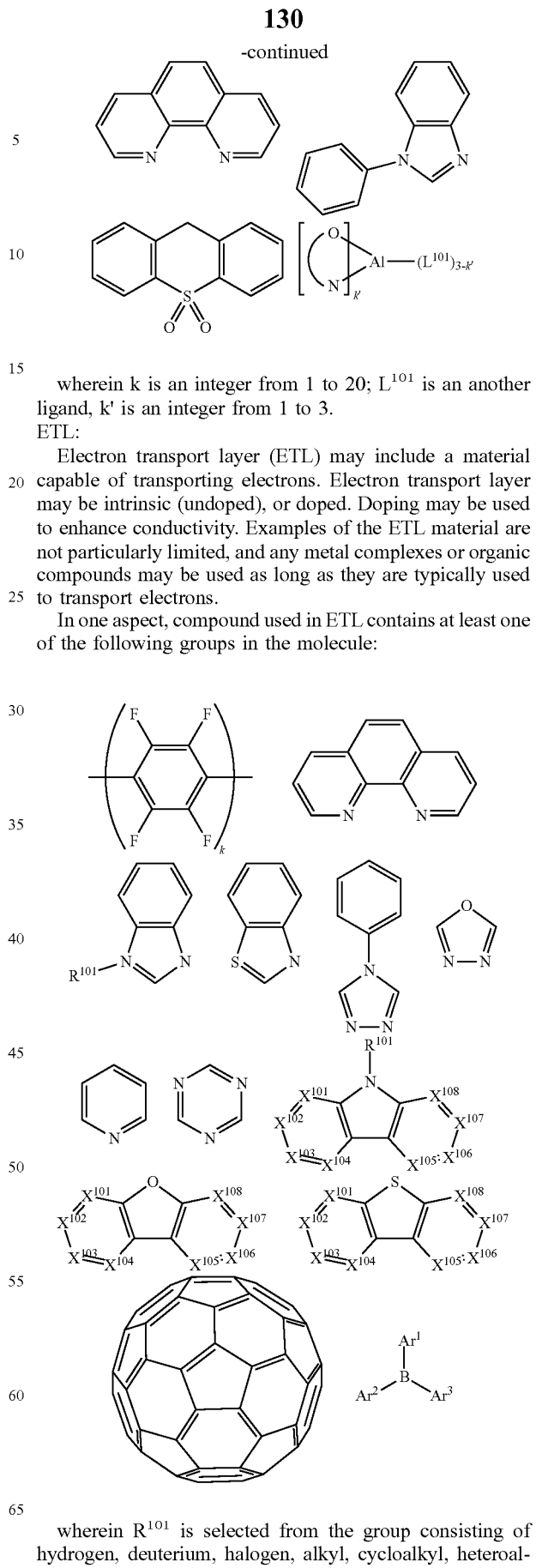

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

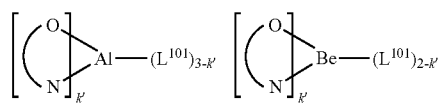
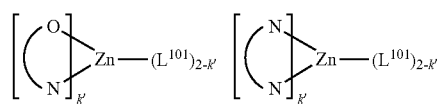

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

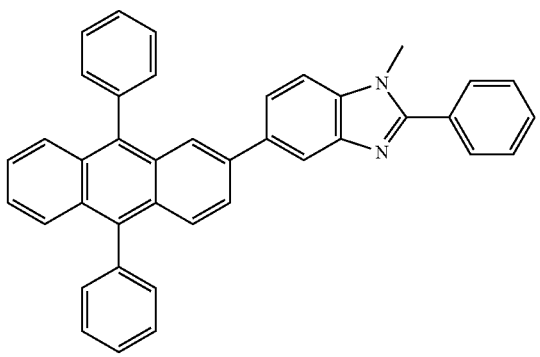

,

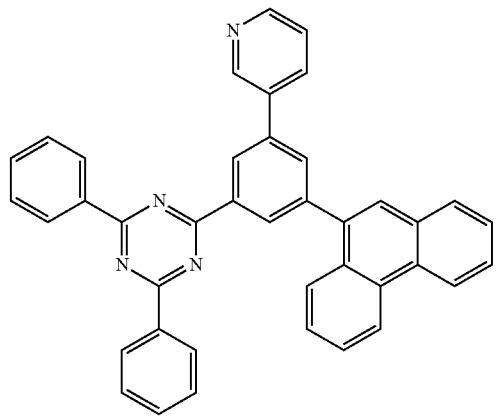

,

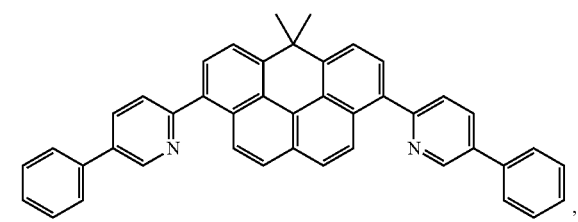

,

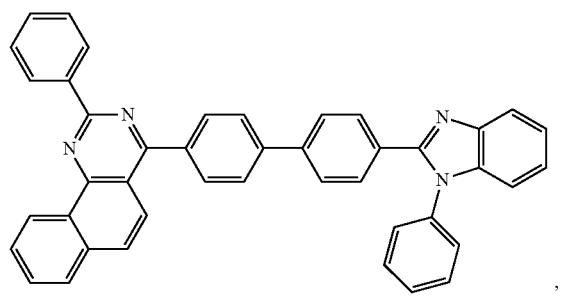

,

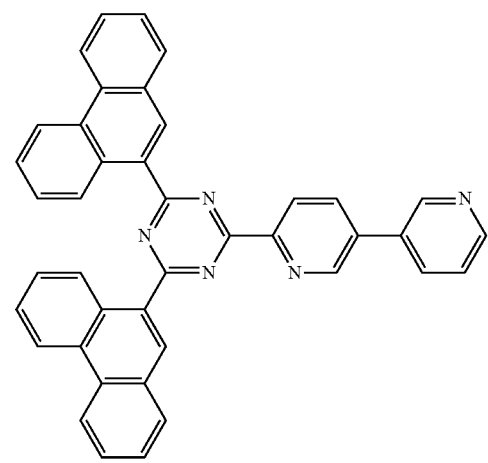

,

133
-continued
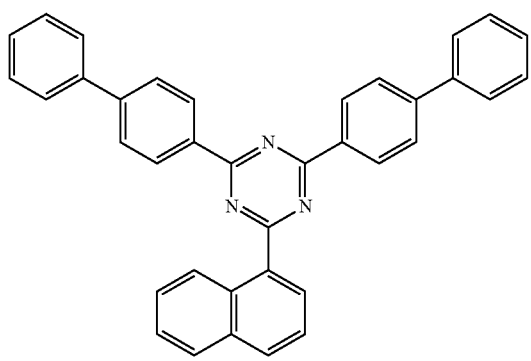
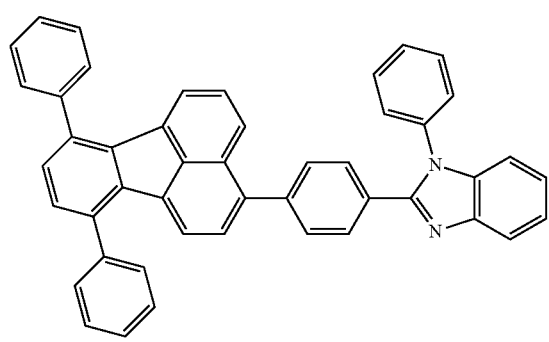
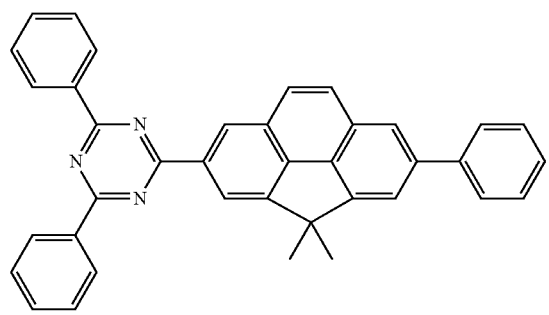
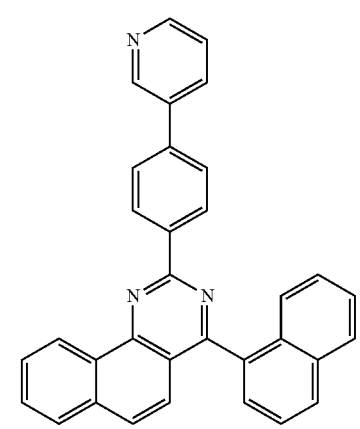
134
-continued
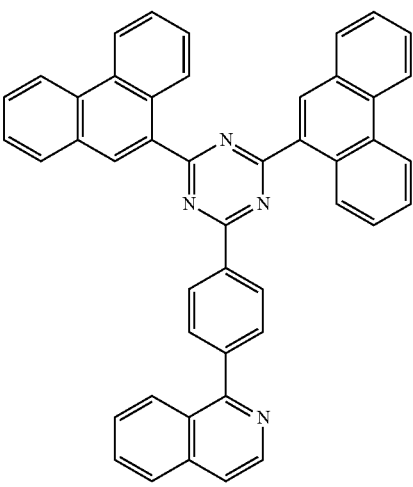
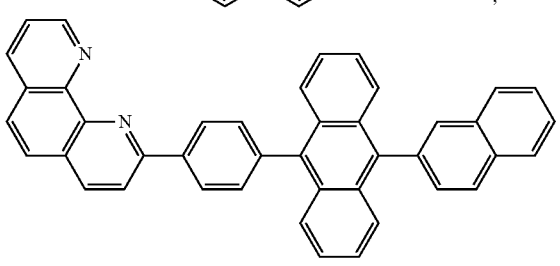
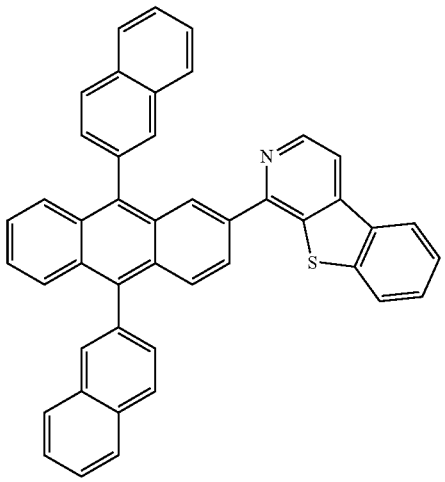
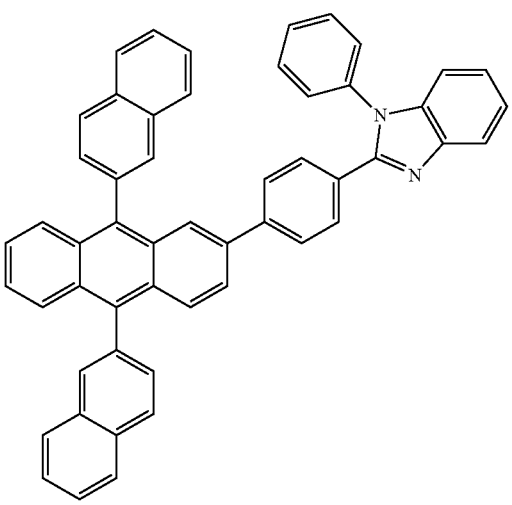

135
-continued
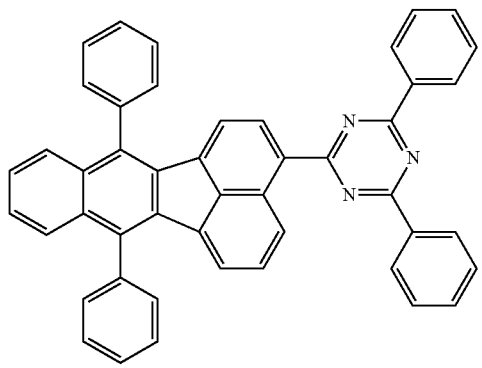
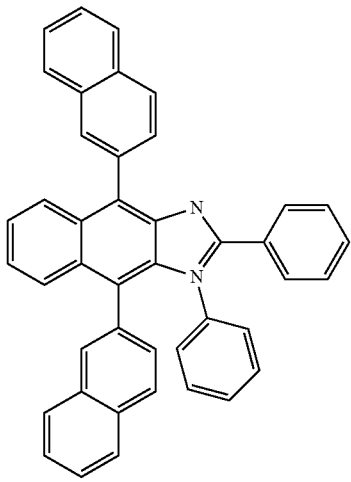
136
-continued
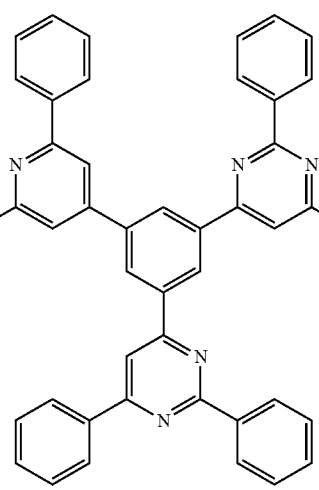
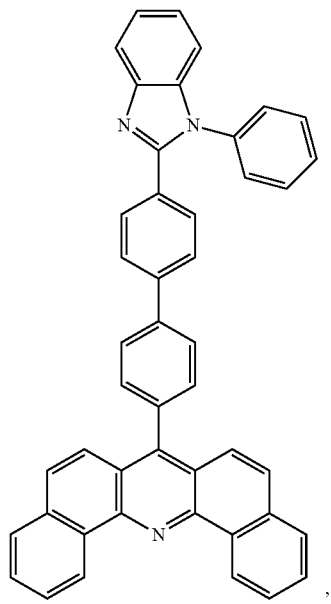

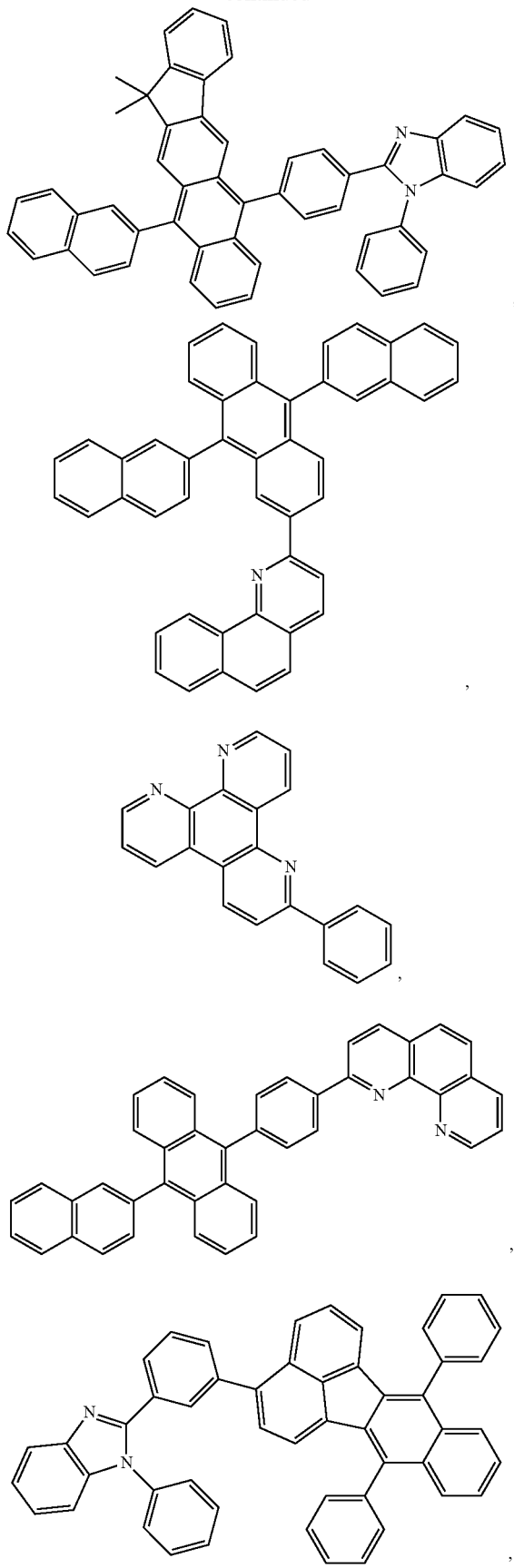
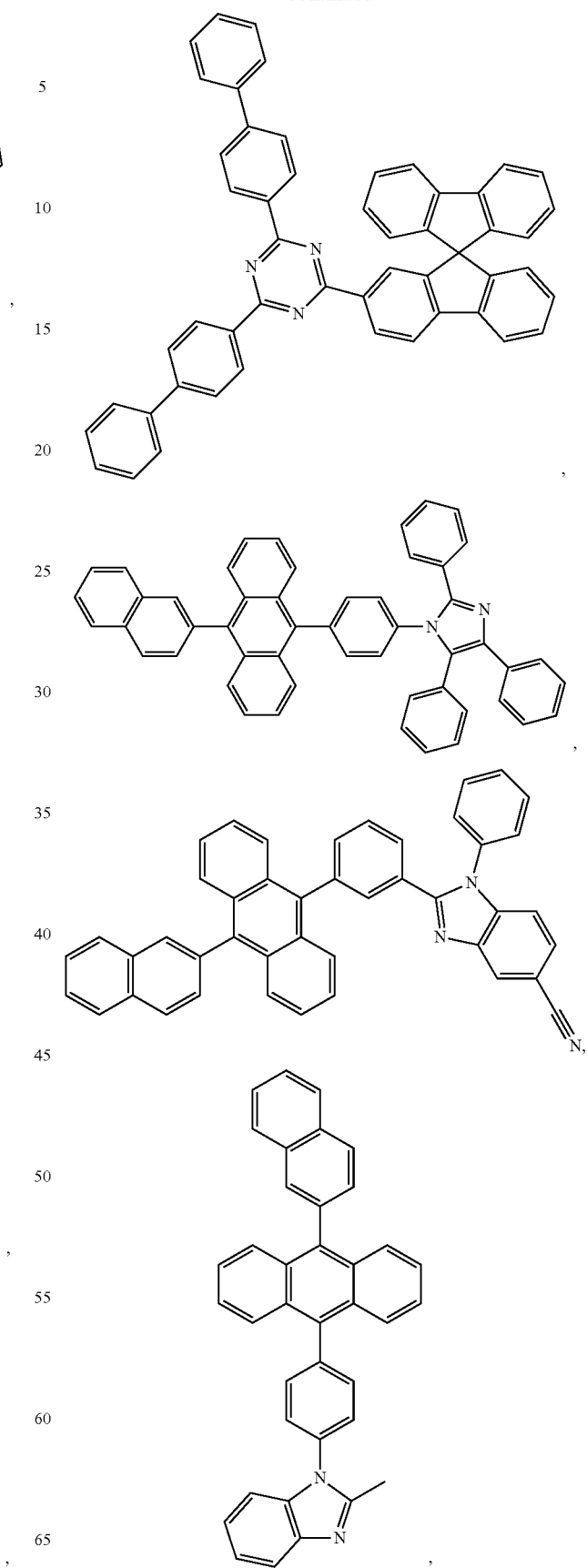

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

Synthetic Examples

Synthesis of Compound 3,063,483

Step 1: Synthesis of 2-iodo-4'-methoxy-1,1'-biphenyl

A solution of concentrated hydrochloric acid (4.6 mL, 55 mmol) in water (85 ml) was added slowly to 4'-methoxy-

[1,1'-biphenyl]-2-amine (10 g, 42 mmol) with stirring. The mixture was cooled in an ice bath and sodium nitrite (4.38 g, 63.5 mmol) in water (20 mL) was added dropwise to maintain an internal temperature between 5° C. and 10° C. The reaction mixture was then stirred for 1 hour at 5° C., then acetonitrile (MeCN) (5 mL) was added to dissolve the precipitates. Urea (1.40 g, 23.3 mmol) was added, followed by dropwise addition of KI (14 g, 85 mmol) in water (20 mL). The reaction mixture was stirred for 18 hours at room temperature (~22° C.). The reaction mixture was then diluted with a saturated aqueous sodium thiosulfate solution (100 mL) and the product was extracted with ethyl acetate (2×250 mL), dried over $Na_2SO_4$ and concentrated in vacuo. The material was purified by column flash chromatography on silica gel (0-10% EtOAc/isohexane) to give 2-iodo-4'-methoxy-1,1'-biphenyl (9.0 g, 68% yield) as a yellow oil that slowly solidified on standing.

Step 2: Synthesis of 2,15-dimethoxytetraphenylene

The 2-iodo-4'-methoxy-1,1'-biphenyl (1) (6.0 g, 19 mmol) from Step 1 was dissolved in trifluoroacetic acid (TFA) (50 mL) and palladium(II) acetate (1.09 g, 4.84 mmol), and silver carbonate (2.67 g, 9.67 mmol) were added. The reaction mixture was heated to 100° C. for 16 hours, then concentrated in vacuo. The residue was dissolved in dichloromethane (DCM) (100 mL), filtered through a short pad of silica gel, then adsorbed onto silica gel. The material was purified by column flash chromatography on silica gel (0-40% DCM/isohexane) to give a mixture of 2,15-dimethoxytetraphenylene and 2,10-dimethoxytetraphenylene in a 2:1 ratio (1.2 g, 16% yield) as a clear colorless gum.

Step 3: Synthesis of tetraphenylene-2,15-diol and tetraphenylene-2,10-diol

The 2:1 mixture of 2,15-dimethoxytetraphenylene and 2,10-dimethoxytetraphenylene (1.2 g, 3.3 mmol) from step 2 was dissolved in DCM (30 mL), cooled to 0° C. and $BBr_3$ (1 M in DCM, 15 mL, 15 mmol) was added dropwise. The reaction mixture was stirred at room temperature for 3 hours, then concentrated in vacuo. Water (20 mL) and saturated aqueous $NaHCO_3$ (100 mL) solution were added, and the aqueous phase was extracted with 10% methanol/DCM (2×100 mL), then dried over $Na_2SO_4$ and concentrated in vacuo. The residue was purified by column flash chromatography on silica gel (20% acetone/isohexane) to give a mixture of isomers (780 mg) as a colorless oil. This material was further purified by preparative reverse phase-high-performance liquid chromatography (RP-HPLC) (25-50% acetonitrile/water; 10 mM ammonium bicarbonate; 'Waters ELSD system'; BEH X-Bridge 19×50 mm column) to give (first eluting) tetraphenylene-2,10-diol (170 mg, 15% yield) as white solid and (second eluting) tetraphenylene-2,15-diol (290 mg, 26% yield) as a white solid.

Step 4: Synthesis of Tetraphenylene-2,15-diyl bis(trifluoromethanesulfonate)

Tetraphenylene-2,15-diol (160 mg, 0.476 mmol) from step 3, $K_2CO_3$ (263 mg, 1.90 mmol), and 1,1,1-trifluoro-N-phenyl-N-((trifluoromethyl)sulfonyl)methanesulfonamide (510 mg, 1.43 mmol) were dissolved in acetonitrile (20 mL) under $N_2$ and the mixture was stirred at room temperature (~22° C.) for 16 hours. The reaction mixture was poured into an ice-water (10 mL) mixture and extracted with ethyl acetate (3×30 mL). The combined organic layers were washed with brine (10 mL), dried over $Na_2SO_4$, and concentrated in vacuo. Two successive purifications by column chromatography on silica gel (0-10% ethylacetate/isohexane, then isohexane) gave tetraphenylene-2,15-diyl bis (trifluoromethanesulfonate) (150 mg, 52% yield) as a white solid.

Step 5: Synthesis of 15-(Diphenylamino)tetraphenylen-2-yl trifluoromethanesulfonate A mixture of diphenylamine (54 mg, 0.32 mmol), tetraphenylene-2,15-diylbis(trifluoromethanesulfonate) (190 mg, 0.316 mmol) from step 4, and sodium tert-butoxide (61 mg, 0.63 mmol) in toluene (10 mL) was degassed with N2 bubbling for 20 min. Di-tert-butyl(1-methyl-2,2-diphenylcyclopropyl)phosphane (13 mg, 0.038 mmol) and allylpalladium chloride dimer (3.5 mg, 9.5 μmo) were added and the resulting mixture was heated at reflux for 16 hours. The reaction was re-charged with additional diphenylamine (4 mg, 0.02 mmol), allylpalladium chloride dimer (3.5 mg, 9.5 μmol), and di-tertbutyl(1-methyl-2,2-diphenylcyclopropyl) phosphane (13 mg, 0.038 mmol), stirred at reflux for an additional 3 hours, then concentrated in vacuo. The residue was diluted with water (5 mL), extracted with 10% methanol/DCM (2×5 mL), passed through a hydrophobic phase-separator and concentrated in vacuo. Three successive purifications by column flash chromatography on silica gel (0-10% ethyl acetate/pentane; 0-2% methyl tert-butyl ether (MTBE)/pentane twice) followed by reverse phase (C18) column chromatography (0-100% acetonitrile/water; 10 mM ammonium bicarbonate) gave 15-(diphenylamino)tetraphenylen-2-yl trifluoromethanesulfonate (41 mg, 18% yield) as a white solid.

Step 6: Synthesis of 4-(4,4,5,5-tetramethyl-1,3,2-dioxaborolan-2-yl)phthalonitrile 4-Bromophthalonitrile (3.0 g, 14 mmol) and potassium acetate (4.27 g, 43.5 mmol) were suspended in Dioxane (30 mL) and the mixture was purged with N2 for 10 min. Bis(pinacolato)diboron (4.60 g, 18.1 mmol) and $PdCl_2$ (dppf) (0.742 g, 1.01 mmol) were added and the reaction mixture was heated at 90° C. for 16 h. The reaction mixture was cooled to RT, diluted with DCM (50 mL), washed with water (25 mL) and brine (25 mL), dried over $Na_2SO_4$, filtered and concentrated in vacuo. Purification by column flash chromatography (0-10% MeOH/DCM) gave 4-(4,4,5,5-tetramethyl-1,3,2-dioxaborolan-2-yl)phthalonitrile (1.0 g, 26% yield) as a pale blue solid.

Step 7: Synthesis of 4-(15-(Diphenylamino)tetraphenylen-2-yl)phthalonitrile (Compound 3063483)

A mixture of 15-(diphenylamino)tetraphenylen-2-yl trifluoromethanesulfonate from step 5 (40 mg, 0.065 mmol), 4-(4,4,5,5-tetramethyl-1,3,2-dioxaborolan-2-yl)phthalonitrile (33 mg, 0.129 mmol) from step 6, and sodium carbonate (14 mg, 0.13 mmol) in dioxane (5 mL) and water (0.5 mL) was degassed with bubbling N2 for 15 min. tris(dibenzylideneacetone)dipalladium(0) (Pd2(dba)3) (2 mg, 3 μmo) and 2-dicyclohexylphosphino-2',6'-dimethoxybiphenyl (Sphos) (3 mg, 8 μmo) were added and the mixture was heated at reflux for 16 hours. The reaction mixture was cooled to room temperature, diluted with water (5 mL), extracted with 10% methanol/DCM (3×5 mL) and concentrated in vacuo. Two successive chromatographic purifications (reverse phase (C18), 0-80% acetonitrile/water; 10 mM ammonium bicarbonate; then silica gel, 0-20% ethyl acetate/isohexane) gave 4-(15-(diphenylamino)tetraphenylen-2-yl)phthalonitrile (13 mg, 33% yield) as a yellow solid.

Data Examples

Table 1 shows first singlet ($S_1$)-first triplet ($T_1$) values that were calculated using density functional theory (DFT) for compound 2,929,762; compound 2,946,421; compound 3,063,821; compound 3,062,822; compound 3,062,823; compound 3,063,483; compound 3,063,006; compound 3,063,014; and compound 3,063,126. These very small $S_1$-$T_1$ gaps can lead to very efficient thermally activated delayed fluorescence (TADF) behaviour. Another aspect to be noted here is that from Compound 3,063,821 (one donor) to Compound 2946421 (two same donors) to Compound 2,929,762 (two different donors), the S1-T1 gap is reduced and there are multiple charge transfer states close in energy. In Compound 2,929,762 with two slightly different donors, the addition of the methyl group on the donor results in a slightly higher HOMO level of the donor unit on the right side of the molecule. This results in a lower energy charge transfer (hence the lower energy S1 and T1) between the acceptor unit and the donor unit. Now a charge transfer state can form between the acceptor unit and the donor unit on the left or right side of the molecule. These two charge transfer states are close in energy and can mix which should result in faster TADF emission from Compound 2,929,762 than Compound 2,946,421 or Compound 3,063,821.

Further evidence that using either at least two donors and one acceptor or two acceptors and one donor in the molecule can bring two or more charge transfer states close in energy, the $S_1$, $S_2$, and $S_3$ of the compounds discussed above were calculated. They are presented in Table 2 below. As can be seen, the compounds with two same or different donors have much smaller S3-S1 gap then the one with just one donor.

The singlet and triplet energies were calculated using Gaussian 16, Revision B.01, using time-dependent density functional theory (TDDFT) at the ground state geometries, with the B3LYP functional employing a 6-31G* basis set and THF solvent. Table 1 below provides the singlet ($S_1$), triplet ($T_1$), and singlet-triplet ($S_1$-$T_1$) gap values or selected compounds calculated using DFT.

TABLE 1

| Chemical Structure | | $S_1$ (nm) | $T_1$ (nm) | $S_1$ - $T_1$ (meV) | HOMO (eV) | LUMO (eV) |
|---|---|---|---|---|---|---|
| Compound 2,929,762 | | 441 | 453 | 75 | −5.51 | −2.25 |
| Compound 2,946,421 | | 432 | 444 | 78 | −5.59 | −2.26 |

TABLE 1-continued

| Chemical Structure | S₁ (nm) | T₁ (nm) | S₁ − T₁ (meV) | HOMO (eV) | LUMO (eV) |
|---|---|---|---|---|---|
| Compound 3,063,821 | 430 | 443 | 85 | −5.61 | −2.27 |
| Compound 3,062,822 | 429 | 440 | 72 | −5.52 | −2.34 |
| Compound 3,062,823 | 498 | 499 | 5 | −5.12 | −2.33 |
| Compound 3,063,483 | 512 | 513 | 5 | −5.13 | −2.34 |

TABLE 1-continued

| Compound | Chemical Structure | $S_1$ (nm) | $T_1$ (nm) | $S_1 - T_1$ (meV) | HOMO (eV) | LUMO (eV) |
|---|---|---|---|---|---|---|
| Compound 3,063,006 | 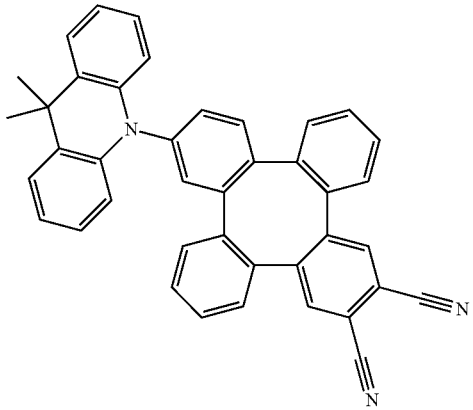 [SMILES: CC1(C)c2ccccc2N(c2ccc3c(c2)-c2ccccc2-c2cc(C#N)c(C#N)cc2-c2ccccc2-3)c2ccccc21] | 517 | 517 | 0 | −5.07 | −2.31 |
| Compound 3,063,014 | 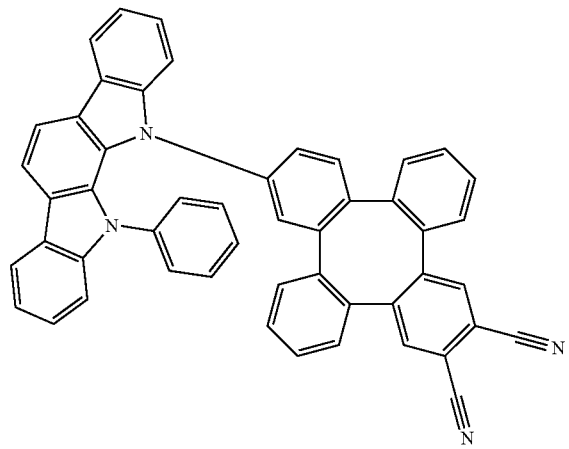 [SMILES: N#Cc1cc2c(cc1C#N)-c1ccccc1-c1cc(-n3c4ccccc4c4ccc5c6ccccc6n(-c6ccccc6)c5c43)ccc1-c1ccccc1-2] | 480 | 480 | 0 | −5.34 | −2.35 |
| Compound 3,063,126 | 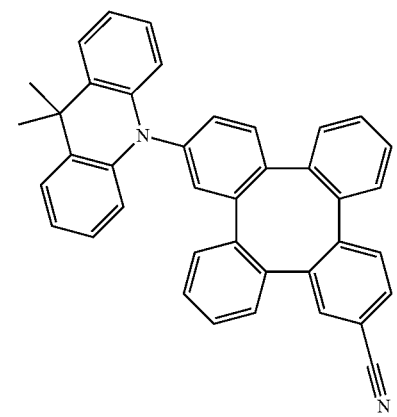 [SMILES: CC1(C)c2ccccc2N(c2ccc3c(c2)-c2ccccc2-c2cc(C#N)ccc2-c2ccccc2-3)c2ccccc21] | 401 | 401 | 0 | −5.07 | −2.31 |

TABLE 2

| Compound | $S_1$ (eV) | $S_2$ (eV) | $S_3$ (eV) | $\Delta S_3 - S_1$ (eV) |
|---|---|---|---|---|
| 3,063,821 | 2.89 | 3.30 | 3.64 | 0.75 |
| 2,946,421 | 2.87 | 2.90 | 3.28 | 0.41 |
| 2,929,762 | 2.81 | 2.89 | 3.23 | 0.42 |

Figure 3:
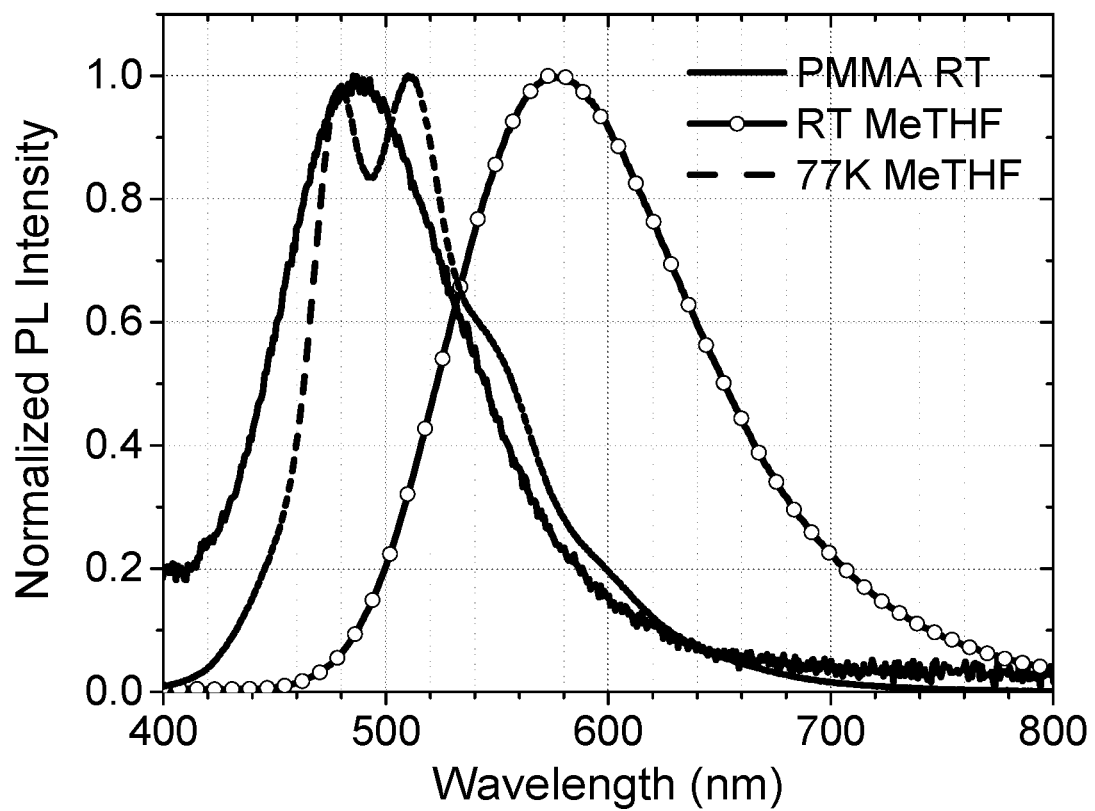
FIG. 3 shows the photoluminescent spectra of Compound 3,063,483 in polymethylmethacrylate at room temperature, in 2-methyltetrahydrofuran at room temperature, and in 2-methyltetrahydrofuran at 77 K.

FIG. 3 shows the photoluminescent spectra of Compound 3,063,483. The significant spectral shift between polymethylmethacrylate (PMMA) film and 2-methyl tetrahydrofuran (2-MeTHF) at room temperature suggests that the compound has a highly polar excited state which is usually a charge transfer state for molecules involving donor(s) and acceptor(s). In the case of Compound 3,063,483, the diphenylamine is a donor and the phthalonitrile is an acceptor. The 2-MeTHF spectrum at 77K overlaps quite well with that in PMMA at room temperature, indicating very close $S_1$ and $T_1$ energies, which is an important criterion for TADF property.

The calculations obtained with the above-identified DFT functional set and basis set are theoretical. Computational composite protocols, such as the Gaussian09 with B3LYP and CEP-31G protocol used herein, rely on the assumption that electronic effects are additive and, therefore, larger basis sets can be used to extrapolate to the complete basis set (CBS) limit. However, when the goal of a study is to understand variations in HOMO, LUMO, S1, T1, bond dissociation energies, etc. over a series of structurally-related compounds, the additive effects are expected to be similar. Accordingly, while absolute errors from using the B3LYP may be significant compared to other computational methods, the relative differences between the HOMO, LUMO, S1, T1, and bond dissociation energy values calculated with B3LYP protocol are expected to reproduce experiment quite well. See, e.g., Hong et al., Chem. Mater. 2016, 28, 5791-98, 5792-93 and Supplemental Information (discussing the reliability of DFT calculations in the context of OLED materials). Moreover, with respect to iridium or platinum complexes that are useful in the OLED art, the data obtained from DFT calculations correlates very well to actual experimental data. See Tavasli et al., J. Mater. Chem. 2012, 22, 6419-29, 6422 (Table 3) (showing DFT calculations closely correlating with actual data for a variety of emissive complexes); Morello, G. R., J. Mol. Model. 2017, 23:174 (studying of a variety of DFT functional sets and basis sets and concluding the combination of B3LYP and CEP-31G is particularly accurate for emissive complexes).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having exactly one structure of Formula I:

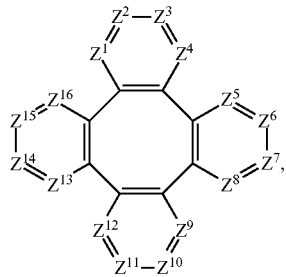

wherein $Z^1$ to $Z^{16}$ are each CR or N;
wherein three consecutive ones of $Z^1$ to $Z^{16}$ within the same ring cannot be N;
wherein each R is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
wherein at least one R comprises a donor substituent selected from the group consisting of carbazole, indolocarbazole, indoloindole, phenothiazine, 5H-benzo[d]benzo[4,5]imidazo[1,2-a]imidazole, diphenylamino, phenoxazine, phenothiazine, dibenzoazasiline, pyrrolidine, piperidine, phenoxide, and methoxide;
wherein at least one R comprises an acceptor substituent selected from the group consisting of a halogen, a nitrile group, a 5-membered aromatic ring containing at least two heteroatoms, and a 6-membered heteroaromatic ring;

wherein the at least one R comprising a donor substituent and the at least one R comprising an acceptor substituent are different;
wherein at least one of the following is true: (i) wherein at least one R comprises a donor substituent selected from the group consisting of indolocarbazole, indoloindole, phenoxazine, phenothiazine, 5H-benzo[d]benzo[4,5]imidazo[1,2-a]imidazole, dibenzoazasiline, and pyrrolidine, or (ii) the compound has exactly one donor substituent and exactly one acceptor substituent, and the acceptor substituent comprises heteroaryl; and
wherein any two Rs on the same 6-membered ring can be joined or fused together to form a ring, and Rs from different 6-membered rings cannot be joined, with the proviso that if the acceptor is selected from the group consisting of aza-carbazole, aza-dibenzofuran and aza-dibenzothiophene, then the donor is not carbazole.

2. The compound of claim 1, wherein at least one R comprises at least one acceptor group selected from the group consisting of cyano, pyrazole, imidazole, triazole, pyridine, pyrimidine, triazine, aza-carbazole, aza-dibenzofuran, and aza-dibenzothiophene group.

3. The compound of claim 1, wherein each one of $Z^1$ through $Z^{16}$ is CR.

4. The compound of claim 3, wherein the exactly one donor substituent comprises carbazole.

5. The compound of claim 1, wherein at least one of $Z^1$ through $Z^{16}$ is N.

6. The compound of claim 1, wherein at least one R comprises a chemical group selected from the group consisting of

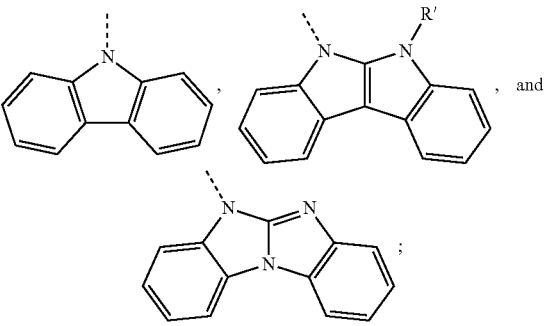

wherein R' is selected from the group consisting of alkyl, cycloalkyl, heteroalkyl, aryl, and heteroaryl.

7. The compound of claim 1 wherein the compound has exactly one donor substituent and exactly one acceptor substituent, and the acceptor substituent comprises heteroaryl.

8. A formulation comprising a compound according to claim 1.

9. A chemical structure selected from the group consisting of a monomer, a polymer, a macromolecule, and a supramolecule, wherein the chemical structure comprises a monovalent or polyvalent variant of a compound of claim 1.

10. The compound of claim 1, wherein a maximum of one R per 6-membered ring is not hydrogen.

11. The compound of claim 1, wherein at least one of the 6-membered rings of Formula I has two Rs that comprise nitrile.

12. An organic light emitting device (OLED) comprising:
an anode;
a cathode; and
an organic layer, disposed between the anode and cathode, comprising a compound of claim 1.

13. A compound selected from the group consisting of the following compounds:

| Compound Z | Structure of Compound Z | $Ar^1, Ar^2, Ar^3, Ar^4$ | Z |
|---|---|---|---|
| Compound 1 to Compound 540,000 having the structure | (structure with $Ar^1, Ar^2, Ar^3, Ar^4$ attached to a ring of $C^x$–$C^y$ atoms) | wherein $Ar^1$ = Di, $Ar^2$ = Aj, $Ar^3$ = Ak, and $Ar^4$ = Al, wherein i is an integer from 1 to 20, j is an integer from 1 to 30, k is an integer from 1 to 30, and l is an integer from 1 to 30, | wherein $Z = i + 20(j - 1) + 600 (k - 1) + 18,000 (l - 1)$, |
| Compound 540,001 to Compound 1436,000 having the structure | (structure with $Ar^1, Ar^2, Ar^3, Ar^4$ attached to a ring of $C^x$–$C^y$ atoms) | wherein $Ar^1$ = Ai, $Ar^2$ = Dj, $Ar^3$ = Dk, and $Ar^4$ = Dl, wherein i is an integer from 1 to 14, j is an integer from 1 to 40, k is an integer from 1 to 40, and l is an integer from 1 to 40, | wherein $Z = i + 14(j - 1) + 560 (k - 1) + 22,400 (l - 1) + 540,000$, |
| Compound 1,436,001 to Compound 1,468,000 having the structure | (structure with $Ar^1, Ar^2, Ar^3, Ar^4$ attached to a ring of $C^x$–$C^y$ atoms) | wherein $Ar^1$ = Ai, $Ar^2$ = Dj, $Ar^3$ = Dk, and $Ar^4$ = Dl, wherein i is an integer from 29 to 30, j is an integer from 1 to 40, k is an integer from 1 to 20, and l is an integer from 1 to 20, | wherein $Z = (i - 28) + 2(j - 1) + 80(k - 1) + 1,600 (l - 1) + 1,4360,000$, |
| Compound 1,468,001 to Compound 1,484,000 having the structure | (structure with $Ar^1, Ar^2, Ar^3, Ar^4$ attached to a ring of $C^x$–$C^y$ atoms) | wherein $Ar^1$ = Ai, $Ar^2$ = Dj, $Ar^3$ = Dk, and $Ar^4$ = Dl, wherein i is an integer from 29 to 30, j is an integer from 21 to 40, k is an integer from 1 to 20, and l is an integer from 21 to 40, | wherein $Z = (i - 28) + 2(j - 21) + 40(k - 1) + 800 (l - 21) + 1,468,000$, |
| Compound 1,484,001 to Compound 2,204,000 having the structure | (structure with $Ar^1, Ar^2, Ar^3, Ar^4$ attached to a ring of $C^x$–$C^y$ atoms) | wherein $Ar^1$ = Di, $Ar^2$ = Aj, $Ar^3$ = Ak, and $Ar^4$ = Al, wherein i is an integer from 1 to 20, j is an integer from 1 to 40, k is an integer from 1 to 30, and i is an integer from 1 to 30, | wherein $Z = i + 20(j - 1) + 800 (k - 1) + 24,000 (l - 1) + 1,484,000$, |

-continued

| Compound Z | Structure of Compound Z | Ar¹, Ar², Ar³, Ar⁴ | Z |
|---|---|---|---|
| Compound 2,204,001 to Compound 2,924,000 having the structure | (structure with Ar¹, Ar², Ar³, Ar⁴ attached to central C$^x$–C$^y$ ring) | wherein Ar¹ = Di, Ar² = Aj, Ar³ = Dk, and Ar⁴ = Al, wherein i is an integer from 1 to 20, j is an integer from 1 to 30, k is an integer from 1 to 40, and l is an integer from 1 to 30, | wherein Z = i + 20(j − 1) + 600 (k − 1) + 24,000 (l − 1) + 2,204,000, |
| Compound 2,924,001 to Compound 2,946,400 having the structure | (structure with Ar¹, Ar², Ar³ attached to central ring fused to benzene) | wherein Ar¹ = Di, Ar² = Aj, and Ar³ = Dk, wherein i is an integer from 1 to 40, j is an integer from 1 to 14, and k is an integer from 1 to 40, | wherein Z = i + 14(j − 1) + 560 (k − 1) + 2,924,000, |
| Compound 2,946,401 to Compound 2,948,000 having the structure | (structure with Ar¹, Ar², Ar³ attached to central ring fused to benzene) | wherein Ar¹ = Di, Ar² = Aj and Ar³ = Dk, wherein i is an integer from 1 to 40, j is an integer from 29 to 30, and k is an integer from 1 to 20, | wherein Z = i + 40(j − 29) + 80 (k − 1) + 2,946,400, |
| Compound 2,948,001 to Compound 2,948,800 having the structure | (structure with Ar¹, Ar², Ar³ attached to central ring fused to benzene) | wherein Ar¹ = Di, Ar² = Aj, and Ar³ = Dk, wherein i is an integer from 21 to 40, j is an integer from 29 to 30, and k is an integer from 21 to 40, | wherein Z = (i − 20) + 2(j − 29) + 40(k − 21) + 2,948,000, |
| Compound 2,948,801 to Compound 2,966,800 having the structure | (structure with Ar¹, Ar², Ar³ attached to central ring fused to benzene) | wherein Ar¹ = Ai, Ar² = Dj, and Ar³ = Ak, wherein i is an integer from 1 to 30, j is an integer from 1 to 20, and k is an integer from 1 to 30, | wherein Z = i + 30(j − 1) + 600 (k − 1) + 2,948,800, |

-continued

| Compound Z | Structure of Compound Z | Ar¹, Ar², Ar³, Ar⁴ | Z |
|---|---|---|---|
| Compound 2,966,801 to Compound 3,014,800 having the structure | (structure with Ar¹, Ar², Ar³ on cyclic core with $C^y-C^x$ bonds, attached to a benzene ring) | wherein $Ar^1 = Di$, $Ar^2 = Dj$, and $Ar^3 = Ak$, wherein i is an integer from 1 to 40, j is an integer from 1 to 40, and k is an integer from 1 to 30, | wherein $Z = i + 40(j-1) + 1{,}600(k-1) + 2{,}966{,}800$, |
| Compound 3,014,801 to Compound 3,062,800 having the structure | (structure with Ar¹, Ar², Ar³ on cyclic core with $C^y-C^x$ bonds, attached to a benzene ring) | wherein $Ar^1 = Ai$, $Ar^2 = Dj$, and $Ar^3 = Dk$, wherein i is an integer from 1 to 30, j is an integer from 1 to 40, and k is an integer from 1 to 40, | wherein $Z = i + 30(j-1) + 1{,}200(k-1) + 3{,}014{,}800$, |
| Compound 3,062,801 to Compound 3,063,400 having the structure | (structure with Ar¹, Ar³ on cyclic core with $C^y-C^x$ bonds, fused between two benzene rings) | wherein $Ar^1 = Di$ and $Ar^2 = Aj$, wherein i is an integer from 1 to 20 and j is an integer from 1 to 30, | wherein $Z = i + 20(j-1) + 3{,}062{,}800$, |
| Compound 3,063,401 to Compound 3,064,600 having the structure | (structure with Ar¹, Ar² on cyclic core with $C^y-C^x$ bonds, fused to benzene rings) | wherein $Ar^1 = Di$ and $Ar^2 = Aj$, wherein i is an integer from 1 to 40 and j is an integer from 1 to 30, | wherein $Z = i + 40(j-1) + 3{,}063{,}400$; | with the proviso that donor D2 cannot be present in the same compound as any acceptor selected from the group consisting of A7-A10, A13, A14, A24-A26, and A28-A29;

with the proviso that at least one of the following moieties is present: D2-D5, D7, D10-D20, D23-D25, D27, D30, D32-D40, A2-10, A12-15, and A18-A30;

with the proviso that if the donor substituent is DI or D11, then the acceptor substituent is not A1, A11, or A17;

wherein D1 to D40 have the following structures:

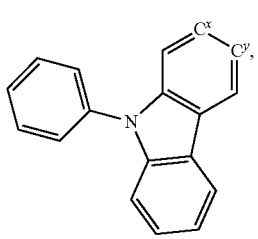

D1

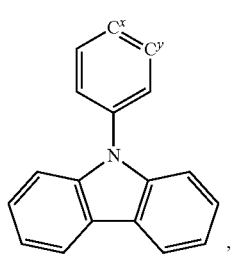

D2

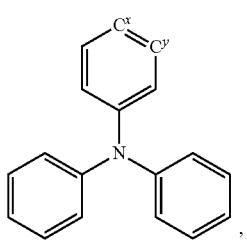

D3

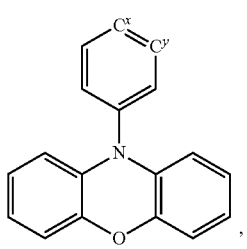

D4

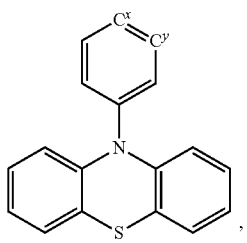

D5

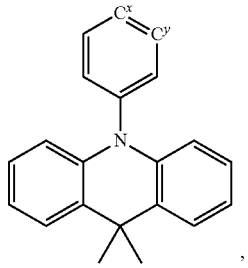

D6

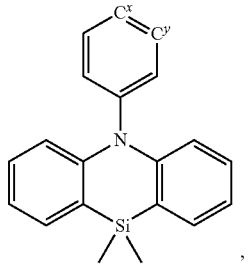

D7

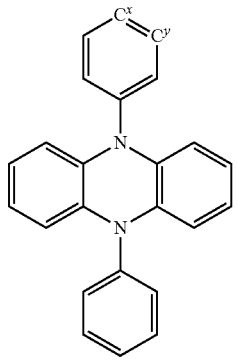

D8

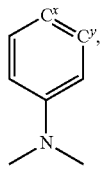

D9

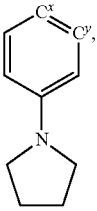

D10

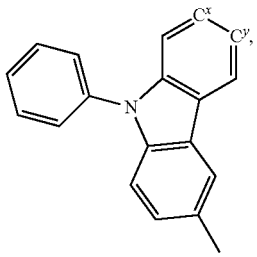

D11

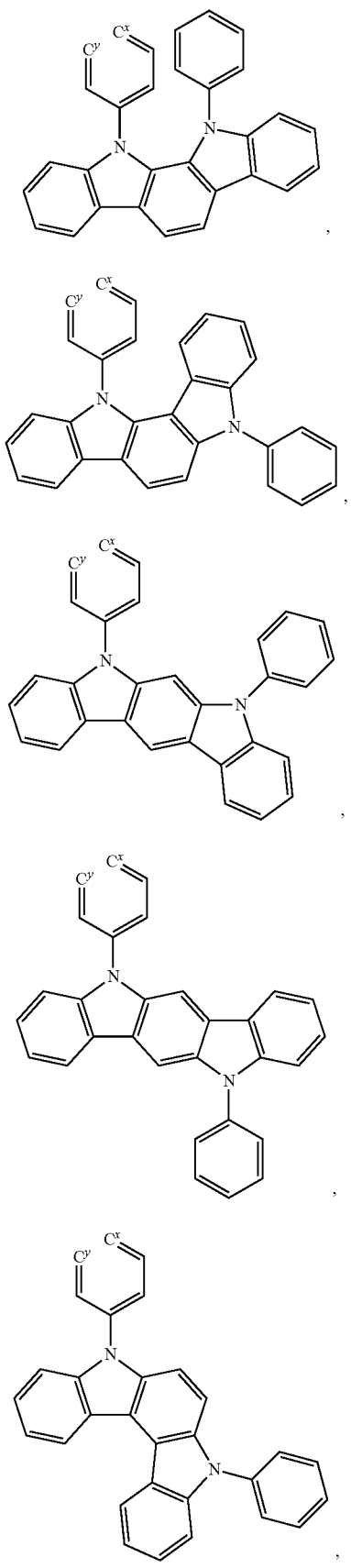
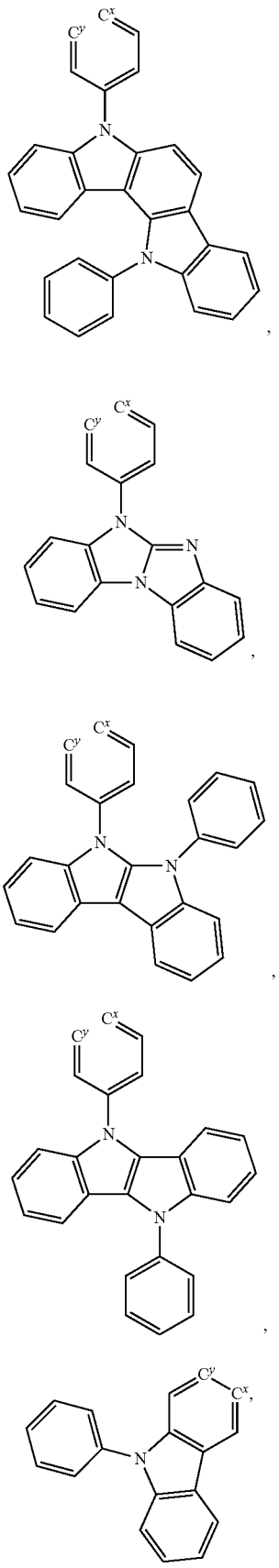

-continued
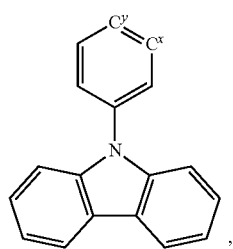 D22
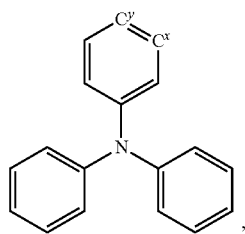 D23
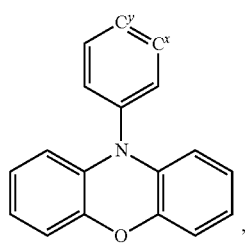 D24
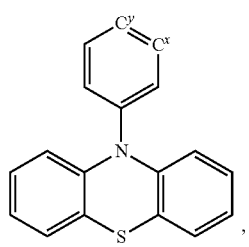 D25
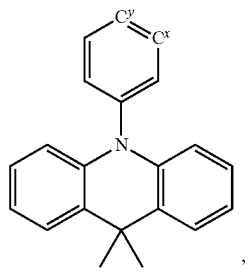 D26
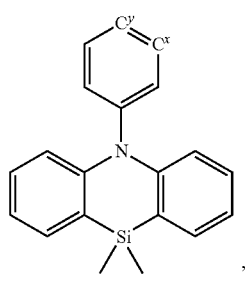 D27
-continued
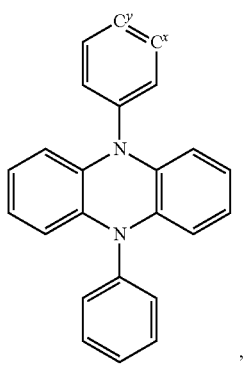 D28
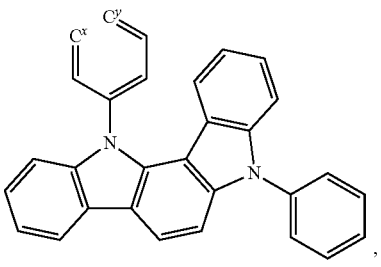 D29

-continued
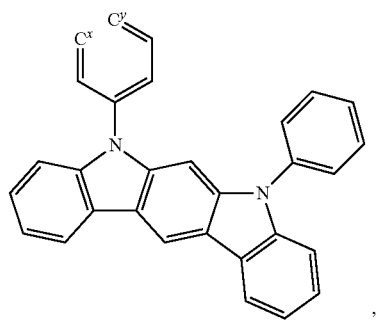
D34
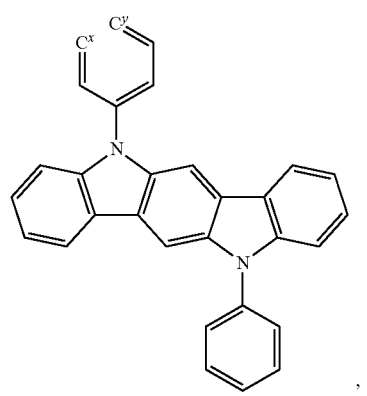
D35
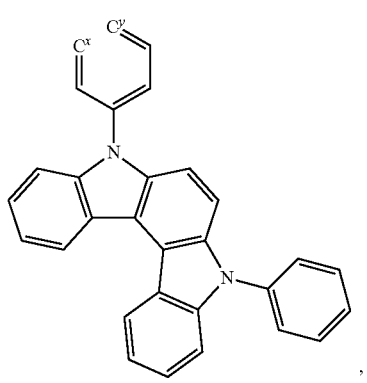
D36
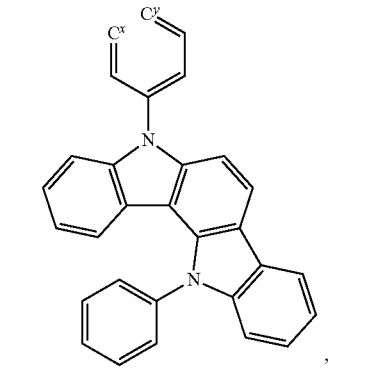
D37
-continued
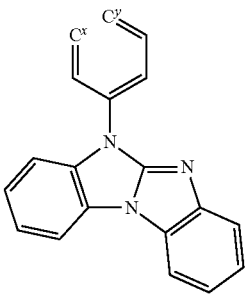
D38
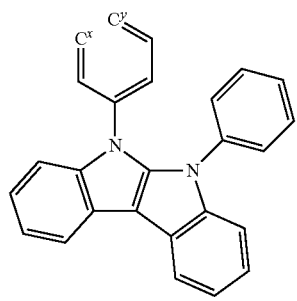
D39
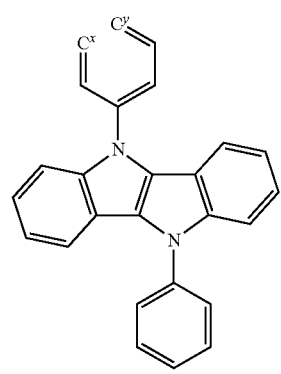
D40
;
and
wherein A1 to A30 have the following structures:
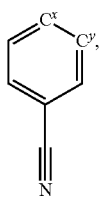
A1
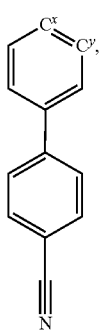
A2

-continued
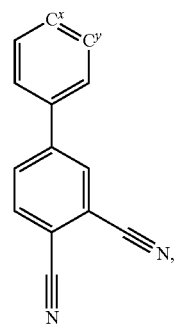
A3
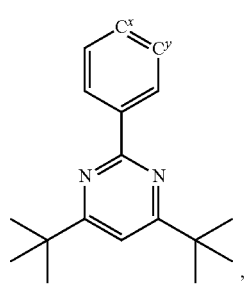
A4
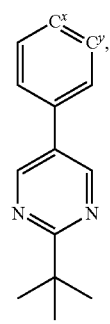
A5
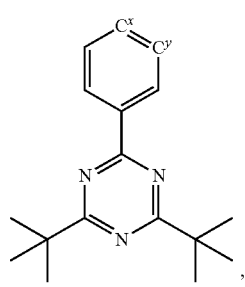
A6
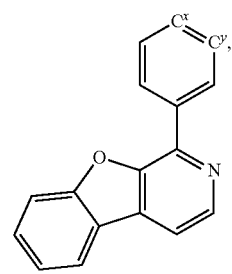
A7
-continued
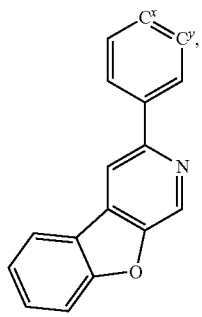
A8
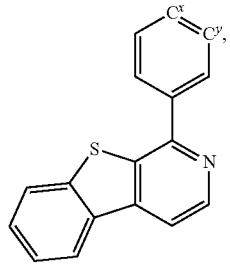
A9
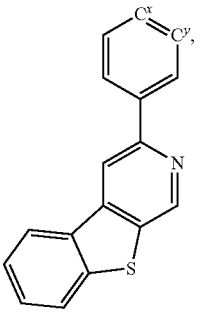
A10
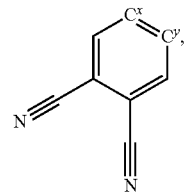
A11
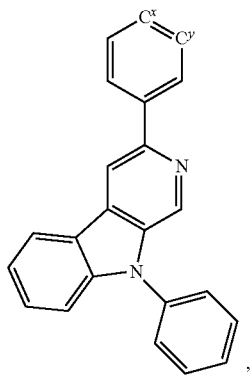
A12

A13 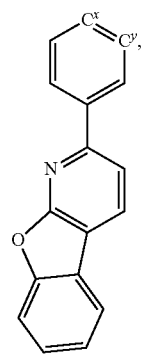
A14 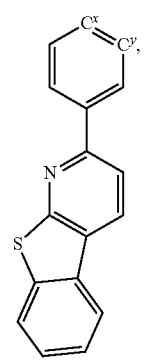
A15 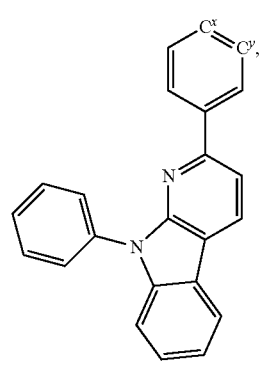
A16 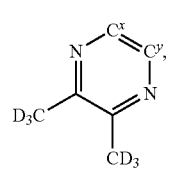
A17 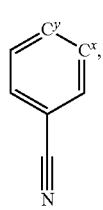
A18 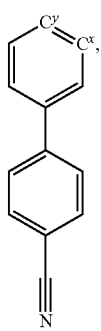
A19 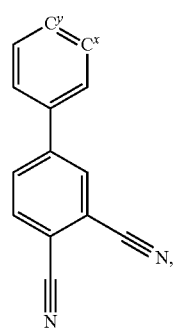
A20 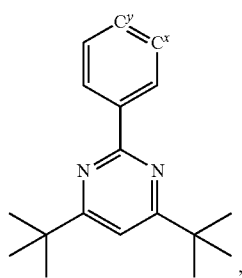
A21 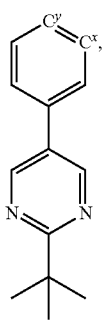
A22 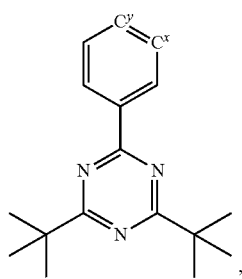

A23 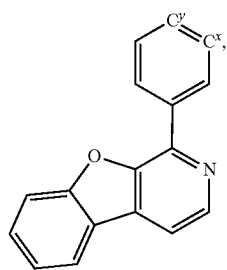
A24 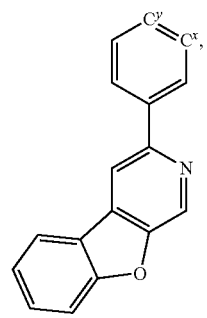
A25 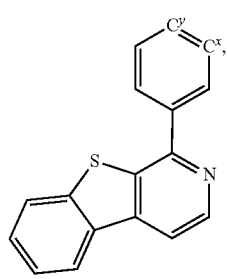
A26 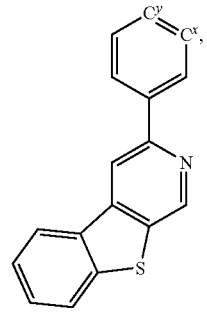
A27 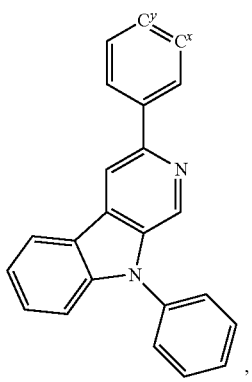
A28 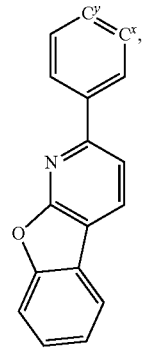
A29 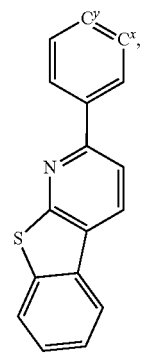
A30 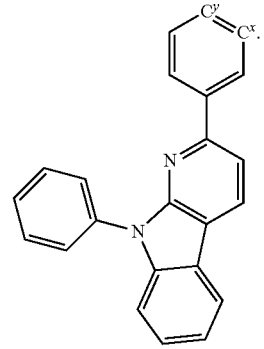
14. An organic light emitting device (OLED) comprising:
an anode;
a cathode; and
an emissive layer, disposed between the anode and cathode, wherein the emissive layer comprises a compound that is an emitter having a structure of Formula I:
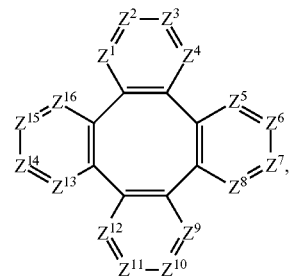
wherein $Z^1$ to $Z^{16}$ are each CR or N;
wherein three consecutive ones of $Z^1$ to $Z^{16}$ within the same ring cannot be N;

wherein each R is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

wherein at least one R comprises a donor substituent selected from the group consisting of carbazole, indolocarbazole, indoloindole, phenothiazine, 5H-benzo[d]benzo[4,5]imidazo[1,2-a]imidazole, diphenylamino, phenoxazine, phenothiazine, dibenzoazasiline, pyrrolidine, piperidine, phenoxide, and methoxide;

wherein at least one R comprises an acceptor substituent selected from the group consisting of a halogen, a nitrile group, a 5-membered aromatic ring containing at least two heteroatoms, and a 6-membered heteroaromatic ring;

wherein the at least one R comprising a donor substituent and the at least one R comprising an acceptor substituent are different;

wherein at least one of the following is true: (i) wherein at least one R comprises a donor substituent selected from the group consisting of indolocarbazole, indoloindole, phenothiazine, diphenylamino, phenoxazine, 5H-benzo[d]benzo[4,5]imidazo[1,2-a]imidazole, dibenzoazasiline, pyrrolidine, piperidine, and phenoxide, or (ii) at least one acceptor substituent comprises aryl or heteroaryl, and each of $Z^1$ to $Z^{16}$ is CR;

if the donor substituents is diphenylamino and the acceptor substituent is nitrile, then two Rs on the same 6-membered ring cannot be joined to form a 5-membered ring; and wherein any two Rs on the same 6-membered ring can be joined or fused together to form a ring, and Rs from different 6-membered rings cannot be joined, with the proviso that if the acceptor is selected from the group consisting of aza-carbazole, aza-dibenzofuran and aza-dibenzothiophene, then the donor is not carbazole.

15. A consumer product comprising an organic light-emitting device (OLED) of claim 14.

16. The consumer product of claim 15, wherein the consumer product is selected from the group consisting of a flat panel display, a curved display, a computer monitor, a medical monitors television, a billboard, a light for interior or exterior illumination and/or signaling, a heads-up display, a fully or partially transparent display, a flexible display, a rollable display, a foldable display, a stretchable display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

17. An organic light emitting device (OLED) comprising:

an anode;

a cathode; and an organic layer, disposed between the anode and cathode, comprising a compound having a structure of Formula I:

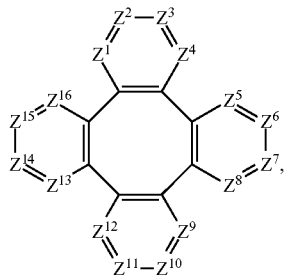

wherein $Z^1$ to $Z^{16}$ are each CR or N;

wherein three consecutive ones of $Z^1$ to $Z^{16}$ within the same ring cannot be N;

wherein each R is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

wherein at least one R comprises a donor substituent selected from the group consisting of carbazole, indolocarbazole, indoloindole, phenothiazine, 5H-benzo[d]benzo[4,5]imidazo[1,2-a]imidazole, diphenylamino, phenoxazine, phenothiazine, dibenzoazasiline, pyrrolidine, piperidine, phenoxide, and methoxide;

wherein at least one R comprises an acceptor substituent selected from the group consisting of a halogen, a nitrile group, a 5-membered aromatic ring containing at least two heteroatoms, and a 6-membered heteroaromatic ring;

wherein the at least one R comprising a donor substituent and the at least one R comprising an acceptor substituent are different;

wherein at least one of the following is true: (i) each of $Z^1$ to $Z^{16}$ is CR, (ii) wherein at least one R comprises a donor substituent selected from the group consisting of indolocarbazole, indoloindole, phenothiazine, diphenylamino, phenoxazine, 5H-benzo[d]benzo[4,5]imidazo[1,2-a]imidazole, dibenzoazasiline, pyrrolidine, piperidine, and phenoxide, (iii) at least one donor substituent comprises aryl or heteroaryl, or (iv) at least one acceptor substituent comprises aryl or heteroaryl; and wherein any two Rs on the same 6-membered ring can be joined or fused together to form a ring, and Rs from different 6-membered rings cannot be joined, with the proviso that if the acceptor is selected from the group consisting of aza-carbazole, aza-dibenzofuran and aza-dibenzothiophene, then the donor is not carbazole, wherein the OLED emits a luminescent radiation at room temperature when a voltage is applied across the first organic light emitting device; wherein the luminescent radiation comprises a delayed fluorescent process.

18. The OLED of claim 17, wherein the organic layer further comprises a sensitizer; and wherein the sensitizer is a phosphorescent emitting material.

19. The OLED of claim 14, wherein the organic layer further comprises a phosphorescent emitting material comprising a metal atom selected from the group consisting of Os, Ir, Pd, Pt, Cu, and Au.

20. The OLED of claim 19, wherein the phosphorescent emitting material further comprises at least one ligand selected from the group consisting of:
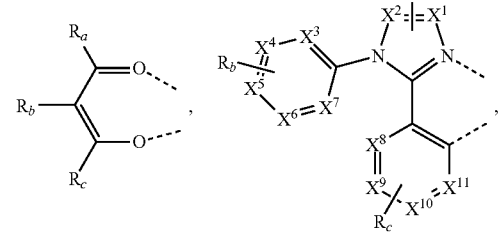
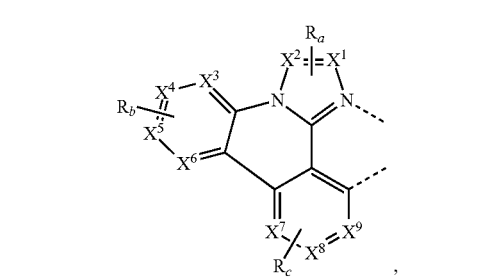
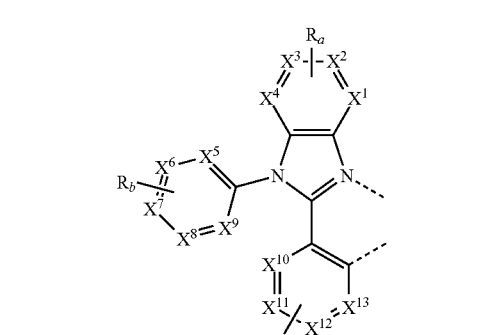
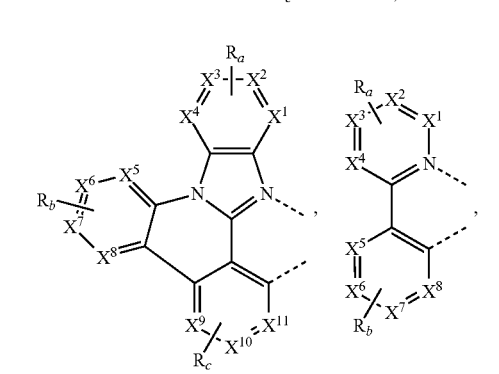
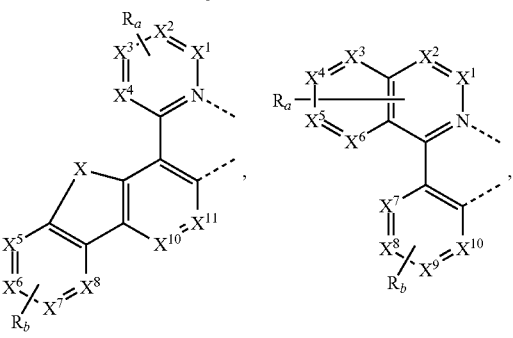
-continued
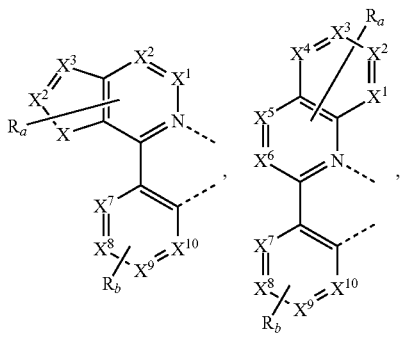
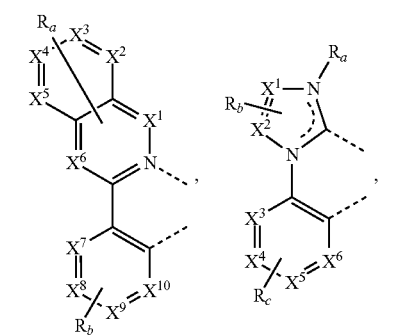
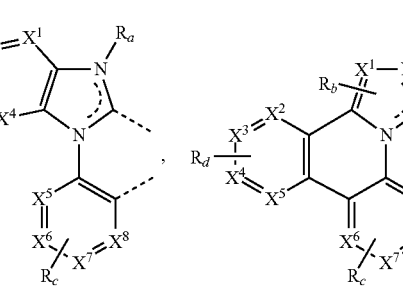
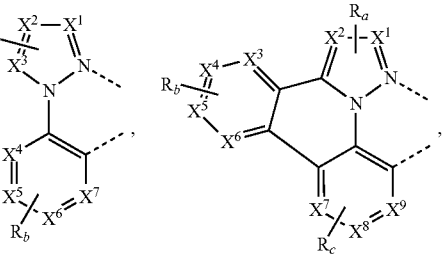
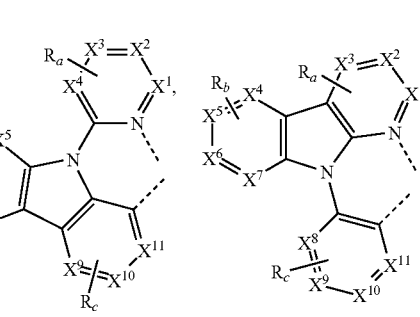
and -continued

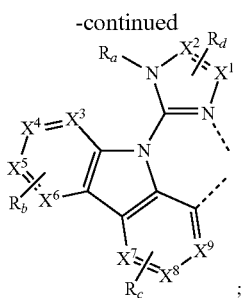

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" can be fused or joined to form a ring;

wherein each $R_a$, $R_b$, $R_c$, and $R_d$ represents from a mono substitution to a maximum possible number of substitutions, or no substitution;

wherein R', R", $R_a$, $R_b$, $R_c$, and $R_d$ are each independently selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and wherein any two adjacent substituents of $R_a$, $R_b$, $R_c$, and $R_d$ can be fused or joined to form a ring or form a multidentate ligand.

* * * * *